(12) United States Patent
Kahne et al.

(10) Patent No.: US 8,957,075 B2
(45) Date of Patent: Feb. 17, 2015

(54) O-GLCNAC TRANSFERASE INHIBITORS AND USES THEREOF

(75) Inventors: Suzanne Walker Kahne, Brookline, MA (US); Michael Block Lazarus, W. Newton, MA (US); Benjamin J. Gross, Philadelphia, PA (US)

(73) Assignee: President and Fellows of Harvard College, Cambridge, MA (US)

( * ) Notice: Subject to any disclaimer, the term of this patent is extended or adjusted under 35 U.S.C. 154(b) by 265 days.

(21) Appl. No.: 13/375,036

(22) PCT Filed: Jun. 1, 2010

(86) PCT No.: PCT/US2010/001596
§ 371 (c)(1),
(2), (4) Date: Jan. 9, 2012

(87) PCT Pub. No.: WO2010/141074
PCT Pub. Date: Dec. 9, 2010

(65) Prior Publication Data
US 2012/0108605 A1    May 3, 2012

Related U.S. Application Data

(60) Provisional application No. 61/217,514, filed on Jun. 1, 2009.

(51) Int. Cl.
| | | |
|---|---|---|
| *A61K 31/496* | (2006.01) | |
| *A61K 31/4709* | (2006.01) | |
| *A61K 31/4725* | (2006.01) | |
| *C07D 401/12* | (2006.01) | |
| *C07D 401/14* | (2006.01) | |
| *C07D 409/14* | (2006.01) | |
| *C07D 215/36* | (2006.01) | |
| *C07D 417/12* | (2006.01) | |
| *C07D 405/12* | (2006.01) | |

(52) U.S. Cl.
CPC ............ *C07D 417/12* (2013.01); *C07D 215/36* (2013.01); *C07D 409/14* (2013.01); *C07D 405/12* (2013.01); *C07D 401/12* (2013.01)
USPC ...... 514/253.07; 514/310; 514/312; 544/363; 546/141; 546/143; 546/157; 546/158

(58) Field of Classification Search
CPC ............ A61K 31/496; A61K 31/4709; A61K 31/4725; C07D 401/12; C07D 401/14; C07D 409/14; C07D 215/36; C07D 417/12; C07D 405/12
USPC ................ 514/310, 312, 253.07; 435/375; 544/363; 546/141, 143, 157, 158
See application file for complete search history.

(56) References Cited

U.S. PATENT DOCUMENTS

| | | |
|---|---|---|
| 3,854,480 A | 12/1974 | Zaffaroni |
| 4,270,537 A | 6/1981 | Romaine |
| 4,420,486 A | 12/1983 | Ohyama et al. |
| 4,452,775 A | 6/1984 | Kent |
| 4,596,556 A | 6/1986 | Morrow et al. |
| 4,675,189 A | 6/1987 | Kent et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,133,974 A | 7/1992 | Paradissis et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,407,686 A | 4/1995 | Patel et al. |
| 5,417,662 A | 5/1995 | Hjertman et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,649,912 A | 7/1997 | Peterson |

(Continued)

FOREIGN PATENT DOCUMENTS

| | | |
|---|---|---|
| CH | 570990 A | 12/1975 |
| CH | 572305 A | 2/1976 |

(Continued)

OTHER PUBLICATIONS

U.S. Appl. No. 61/504,958, filed Jul. 6, 2011, Jiang et al.
U.S. Appl. No. 61/584,443, filed Jan. 9, 2012, Jiang et al.
International Search Report and Written Opinion for PCT/US2010/001596, mailed Jan. 31, 2011.
International Preliminary Report on Patentability for PCT/US2010/001596, mailed Dec. 15, 2011.
International Search Report and Written Opinion for PCT/US2007/008806 mailed Jun. 6, 2008.

(Continued)

*Primary Examiner* — Kamal Saeed
*Assistant Examiner* — Ebenezer O Sackey
(74) *Attorney, Agent, or Firm* — Wolf, Greenfield & Sacks, P.C.; C. Hunter Baker

(57) ABSTRACT

The present invention provides inhibitors of O-GlcNAc transferase. Typically, the inhibitors are quinolinone-6-sulfonamides. The invention also provides pharmaceutical compositions thereof and methods for using the same in diabetes and complications thereof, neurodegenerative diseases, cancers, autoimmune diseases, and inflammatory diseases.

37 Claims, 1 Drawing Sheet

(56) References Cited

U.S. PATENT DOCUMENTS

| | | | |
|---|---|---|---|
| 5,704,911 | A | 1/1998 | Parsons |
| 5,736,152 | A | 4/1998 | Dunn |
| 5,893,397 | A | 4/1999 | Peterson et al. |
| 5,993,412 | A | 11/1999 | Deily et al. |
| 6,388,063 | B1 | 5/2002 | Plowman et al. |
| 6,476,187 | B1 | 11/2002 | Cone et al. |
| 6,852,838 | B2 | 2/2005 | Valenzuela et al. |
| 6,905,681 | B1 | 6/2005 | June et al. |
| 6,916,636 | B2 | 7/2005 | Marx et al. |
| 6,924,356 | B2 | 8/2005 | Ruben et al. |
| 6,955,894 | B1 | 10/2005 | Gatanaga et al. |
| 6,969,758 | B2 | 11/2005 | Ferrara et al. |
| 2002/0128235 | A1 | 9/2002 | Konrad et al. |
| 2003/0032054 | A1 | 2/2003 | Colyer et al. |
| 2003/0087328 | A1 | 5/2003 | Pollok et al. |
| 2003/0186948 | A1 | 10/2003 | Kudlow et al. |
| 2004/0191811 | A1 | 9/2004 | Burghardt et al. |
| 2004/0259910 | A1 | 12/2004 | Bolin et al. |
| 2005/0026266 | A1 | 2/2005 | Clausen et al. |
| 2005/0032145 | A1 | 2/2005 | Burghardt et al. |
| 2005/0113407 | A1 | 5/2005 | Bolin et al. |
| 2005/0113436 | A1 | 5/2005 | Elokdah et al. |
| 2005/0250678 | A1 | 11/2005 | DeFrees et al. |
| 2006/0099150 | A1 | 5/2006 | Houston et al. |
| 2006/0099688 | A1 | 5/2006 | Clausen et al. |
| 2007/0027068 | A1 | 2/2007 | DeFrees et al. |
| 2009/0163545 | A1 | 6/2009 | Goldfarb |
| 2009/0325944 | A1 | 12/2009 | Kahne et al. |
| 2010/0290987 | A1 | 11/2010 | Gross et al. |

FOREIGN PATENT DOCUMENTS

| | | |
|---|---|---|
| FR | 2179293 A5 | 11/1973 |
| GB | 1330611 A | 9/1973 |
| WO | WO 95/24929 A2 | 9/1995 |
| WO | WO 97/13537 A1 | 4/1997 |
| WO | WO 97/37705 A1 | 10/1997 |
| WO | WO 99/34850 A1 | 7/1999 |
| WO | 2007/120638 * | 10/2007 |
| WO | WO 2007/120638 A2 | 10/2007 |
| WO | WO 2008/156676 A1 | 12/2008 |
| WO | WO 2009/036341 A2 | 3/2009 |
| WO | WO 2009/086952 A2 | 7/2009 |
| WO | WO 2010/141074 A2 | 12/2010 |
| WO | WO 2013/006758 A1 | 1/2013 |

(56) References Cited

OTHER PUBLICATIONS

International Preliminary Report on Patentability for PCT/US2007/008806 mailed Oct. 23, 2008.
International Search Report and Written Opinion for PCT/US2008/007410, mailed Sep. 16, 2008.
International Preliminary Report on Patentability for PCT/US2008/007410, mailed Dec. 30, 2009.
International Search Report and Written Opinion for PCT/US2011/051431, mailed Feb. 29, 2012.
PubChem Compound submission: NIH/NCBI; Accession No. 1352610; Jul. 11, 2005.
PubChem Compound submission: NIH/NCBI; Accession No. 2816723; Jul. 19, 2005.
PubChem Compound submission: NIH/NCBI; Accession No. 3531968; Sep. 9, 2005.
PubChem Compound submission: NIH/NCBI; Accession No. 3655724; Sep. 10, 2005.
PubChem Compound submission: NIH/NCBI; Accession No. 4048808; Sep. 13, 2005.
PubChem Compound submission: NIH/NCBI; Accession No. 4247320; Sep. 14, 2005.
PubChem Compound submission: NIH/NCBI; Accession No. 5309478; Dec. 9, 2005.
PubChem Compound submission: NIH/NCBI; Accession No. 6619624; Jun. 5, 2006.
PubChem Compound submission: NIH/NCBI; Accession No. 6619906; Jun. 5, 2006.
PubChem Compound submission: NIH/NCBI; Accession No. 6619938; Jun. 5, 2006.
PubChem Compound submission: NIH/NCBI; Accession No. 6619971; Jun. 5, 2006.
PubChem Compound submission: NIH/NCBI; Accession No. 6620110; Jun. 5, 2006.
PubChem Compound submission: NIH/NCBI; Accession No. 6624064; Jun. 5, 2006.
PubChem Compound submission: NIH/NCBI; Accession No. 6624183; Jun. 5, 2006.
[No Author Listed] The CCP4 suite: programs for protein crystallography. Acta Crystallogr D Biol Crystallogr. Collaborative Computational Project, No. 4. Sep. 1, 1994;50(Pt 5):760-3.
Adams et al., Phenix: a comprehensive Python-based system for macromolecular structure solution. Acta Crystallogr D Biol Crystallogr. Feb. 2010;66(Pt 2):213-21. Epub Jan. 22, 2010.
Akimoto et al., Elevated expression of O-GlcNAc-modified proteins and O-GlcNAc transferase in corneas of diabetic Goto-Kakizaki rats. Invest Ophthalmol Vis Sci. Sep. 2003;44(9):3802-9.
Akimoto et al., Hyperglycemia and the O-GlcNAc transferase in rat aortic smooth muscle cells: elevated expression and altered patterns of O-GlcNAcylation. Arch Biochem Biophys. May 15, 2001;389(2):166-75.
Akimoto et al., Increased O-GlcNAc transferase in pancreas of rats with streptozotocin-induced diabetes. Diabetologia. Oct. 2000;43(10):1239-47.
Alexander et al., Mechanism of carbamate inactivation of FAAH: implications for the design of covalent inhibitors and in vivo functional probes for enzymes. Chem Biol. Nov. 2005;12(11):1179-87.
Almerico et al., In-silico screening of new potential Bcl-2/Bcl-xl inhibitors as apoptosis modulators. J Mol Model. Apr. 2009;15(4):349-55. Epub Dec. 6, 2008.
Andres et al, 4-Thiazolidinones: novel inhibitors of the bacterial enzyme MurB. Bioorg Med Chem Lett. Apr. 17, 2000;10(8):715-7.
Arias et al., Prolonged incubation in PUGNAc results in increased protein O-Linked glycosylation and insulin resistance in rat skeletal muscle. Diabetes. Apr. 2004;53(4):921-30.
Arnold et al., The microtubule-associated protein tau is extensively modified with O-linked N-acetylglucosamine. J Biol Chem. Nov. 15, 1996;271(46):28741-4.
Arnold et al., The Swiss-Model workspace: a web-based environment for protein structure homology modelling. Bioinformatics. Jan. 15, 2006;22(2):195-201. Epub Nov. 13, 2005.
Bartlett et al., CAVEAT: A Program to Facilitate the Structure-derived Design of Biologically Active Molecules. Molecular Recognition in Chemical and Biological Problems. Special Pub. Royal Chem Soc. 1989;78:182-196.
Beasley et al., Miniaturized, ultra-high throughput screening of tyrosine kinases using homogeneous, competitive fluorescence immunoassays. Assay Drug Dev Technol. Apr. 2004;2(2): 141-51.
Berge et al, Pharmaceutical salts. J Pharm Sci. Jan. 1977;66(1):1-19.
Boehmelt et al., Decreased UDP-GlcNAc levels abrogate proliferation control in EMeg32-deficient cells. EMBO J. Oct. 2, 2000;19(19):5092-104.
Boggon et al., Screening for phasing atoms in protein crystallography. Structure. Jul. 15, 2000;8(7):R143-9.
Bohm, The computer program LUDI: a new method for the de novo design of enzyme inhibitors. J Comput Aided Mol Des. Feb. 1992;6(1):61-78.
Bowman et al., Small molecule inhibitors of the MDM2-p53 interaction discovered by ensemble-based receptor models. J Am Chem Soc. Oct. 24, 2007;129(42):12809-14. Epub Sep. 29, 2007.
Brown et al., Glycan antagonists and inhibitors: a fount for drug discovery. Crit Rev Biochem Mol Biol. Nov.-Dec. 2007;42(6):481-515.
Brownlee, Biochemistry and molecular cell biology of diabetic complications. Nature. Dec. 13, 2001;414(6865):813-20.
Brünger et al., Crystallography & NMR system: A new software suite for macromolecular structure determination. Acta Crystallogr D Biol Crystallogr. Sep. 1, 1998;54(Pt 5):905-21.

(56) References Cited

OTHER PUBLICATIONS

Buchan et al., tRNA properties help shape codon pair preferences in open reading frames. Nucleic Acids Res. Feb. 9, 2006;34(3):1015-27. Print 2006.

Burns et al., Silencing of the novel p53 target gene Snk/Plk2 leads to mitotic catastrophe in paclitaxel (taxol)-exposed cells. Mol Cell Biol. Aug. 2003;23(16);5556-71.

Caldwell et al., Nutrient sensor O-GlcNAc transferase regulates breast cancer tumorigenesis through targeting of the oncogenic transcription factor FoxM1. Oncogene. May 13, 2010;29(19):2831-42. Epub Mar. 1, 2010.

Campbell et al., A homogeneous immunoassay for cyclic nucleotides based on chemiluminescence energy transfer. Biochem J. Oct. 15, 1983;216(1):185-94.

Chen et al., Alternative O-GlcNAcylation/O-phosphorylation of Ser16 induce different conformational disturbances to the N terminus of murine estrogen receptor beta. Chem Biol. Sep. 2006;13(9):937-44.

Chen et al., Identification of secret agent as the O-GlcNAc transferase that participates in Plum pox virus infection. J Virol. Aug. 2005;79(15):9381-7.

Cheng et al., Alternative O-glycosylation/O-phosphorylation of the murine estrogen receptor beta. Biochemistry. Sep. 26, 2000;39(38):11609-20.

Chou et al., Characterization and dynamics of O-linked glycosylation of human cytokeratin 8 and 18. J Biol Chem. Feb. 25, 1992;267(6):3901-6.

Chou et al., c-Myc is glycosylated at threonine 58, a known phosphorylation site and a mutational hot spot in lymphomas. J Biol Chem. Aug. 11, 1995;270(32):18961-5.

Chou et al., Glycosylation of the c-Myc transactivation domain. Proc Natl Acad Sci U S A. May 9, 1995;92(10):4417-21.

Cieniewski-Bernard et al., Identification of O-linked N-acetylglucosamine proteins in rat skeletal muscle using two-dimensional gel electrophoresis and mass spectrometry. Mol Cell Proteomics. Jun. 2004;3(6):577-85. Epub Feb. 24, 2004.

Clark et al., Diabetes and the accompanying hyperglycemia impairs cardiomyocyte calcium cycling through increased nuclear O-GlcNAcylation. J Biol Chem. Nov. 7, 2003;278(45):44230-7. Epub Aug. 26, 2003.

Clarke et al., Structural insights into mechanism and specificity of O-GlcNAc transferase. EMBO J. Oct. 22, 2007;27(20):2780-8. Epub Sep. 25, 2008.

Cohen et al., Molecular modeling software and methods for medicinal chemistry. J Med Chem. Mar. 1990;33(3):883-94.

Cole et al., Cytosolic O-glycosylation is abundant in nerve terminals. J Neurochem. Dec. 2001;79(5):1080-9.

Cole et al., Glycosylation sites flank phosphorylation sites on synapsin I: O-linked N-acetylglucosamine residues are localized within domains mediating synapsin I interactions. J Neurochem. Jul. 1999;73(1):418-28.

Comer et al., Characterization of a mouse monoclonal antibody specific for O-linked N-acetylglucosamine. Anal Biochem. Jun. 15, 2001;293(2):169-77.

Comer et al., O-Glycosylation of nuclear and cytosolic proteins. Dynamic interplay between O-GlcNAc and O-phosphate. J Biol Chem. Sep. 22, 2000;275(38):29179-82.

Comer et al., Reciprocity between O-GlcNAc and O-phosphate on the carboxyl terminal domain of RNA polymerase II. Biochemistry. Jul. 3, 2001;40(26):7845-52.

Comess et al., Affinity-based screening techniques for enhancing lead discovery. Curr Opin Drug Discov Devel. Jul. 2004;7(4):411-6.

Compain et al., Carbohydrate mimetics-based glycosyltransferase inhibitors. Bioorg Med Chem. Dec. 2001;9(12):3077-92.

Compain et al., Design, synthesis and biological evaluation of iminosugar-based glycosyltransferase inhibitors. Curr Top Med Chem. 2003;3(5):541-60.

Copeland et al., Cross-talk between GlcNAcylation and phosphorylation: roles in insulin resistance and glucose toxicity. Am J Physiol Endocrinol Metab. Jul. 2008;295(1):E17-28. Epub Apr. 29, 2008.

De La Fortelle et al., SHARP: A Maximum-Likelihood Heavy-Atom Parameter Refinement Program for the MIR and MAD Mehtods. Methods Enzymol. 1997;276:472-94.

Defronzo, Insulin resistance, hyperinsulinemia, and coronary artery disease: a complex metabolic web. J Cardiovasc Pharmacol. 1992;20 Suppl 11:S1-16.

Dentin et al., Hepatic glucose sensing via the CREB coactivator CRTC2. Science. Mar. 7, 2008;319(5868):1402-5.

Dias et al., Regulation of calcium/calmodulin-dependent kinase IV by O-GlcNAc modification. J Biol Chem. Aug. 7, 2009;284(32):21327-37. Epub Jun. 8, 2009.

Dong et al., Cytoplasmic O-GlcNAc modification of the head domain and the KSP repeat motif of the neurofilament protein neurofilament-H. J Biol Chem. Aug. 23, 1996;271(34):20845-52.

Dong et al., Glycosylation of mammalian neurofilaments. Localization of multiple O-linked N-acetylglucosamine moieties on neurofilament polypeptides L and M. J Biol Chem. Aug. 5, 1993;268(22):16679-87.

Dong et al., Purification and characterization of an O-GlcNAc selective N-acetyl-beta-D-glucosaminidase from rat spleen cytosol. J Biol Chem. Jul. 29, 1994;269(30):19321-30.

Donovan et al., A solid-phase glycosyltransferase assay for high-throughput screening in drug discovery research. Glycoconj J. 1999;16(10):607-15.

Dorfmueller et al., Cell-penetrant, nanomolar O-GlcNAcase inhibitors selective against lysosomal hexosaminidases. Chem Biol. Nov. 24, 2010;17(11):1250-5.

Dorfmueller et al., GlcNAcstatin: a picomolar, selective O-GlcNAcase inhibitor that modulates intracellular O-glcNAcylation levels. J Am Chem Soc. Dec. 27, 2006;128(51):16484-5.

Dorfmueller et al., Substrate and product analogues as human O-GlcNAc transferase inhibitors. Amino Acids. Mar. 2011;40(3):781-92. Epub Jul. 17, 2010.

Du et al., Hyperglycemia inhibits endothelial nitric oxide synthase activity by posttranslational modification at the Akt site. J Clin Invest. Nov. 2001;108(9):1341-8.

Emsley et al., Coot: model-building tools for molecular graphics. Acta Crystallogr D Biol Crystallogr. Dec. 2004;60(Pt 12 Pt 1):2126-32. Epub Nov. 26, 2004.

Emsley et al., Features and development of Coot. Acta Crystallogr D Biol Crystallogr. Apr. 2010;66(Pt 4):486-501. Epub Mar. 24, 2010.

Evans, Scaling and assessment of data quality. Acta Crystallogr D Biol Crystallogr. Jan. 2006;62(Pt 1):72-82. Epub Dec. 14, 2005.

Fan et al., Apoptosis induction with polo-like kinase-1 antisense phosphorothioate oligodeoxynucleotide of colon cancer cell line SW480. World J Gastroenterol. Aug. 7, 2005;11(29):4596-9.

Feng et al., A detergent-based assay for the detection of promiscuous inhibitors. Nat Protoc. 2006;1(2):550-3.

Feng et al., High-throughput assays for promiscuous inhibitors. Nat Chem Biol. Aug. 2005;1(3):146-8. Epub Jul. 3, 2005.

Frantom et al., UDP-(5F)-GlcNAc acts as a slow-binding inhibitor of MshA, a retaining glycosyltransferase. J Am Chem Soc. May 19, 2010;132(19):6626-7.

Friesner et al., Extra precision glide: docking and scoring incorporating a model of hydrophobic enclosure for protein-ligand complexes. J Med Chem. Oct. 19, 2006;49(21):6177-96.

Friesner et al., Glide: a new approach for rapid, accurate docking and scoring. 1. Method and assessment of docking accuracy. J Med Chem. Mar. 25, 2004;47(7):1739-49.

Fujiki et al., GlcNAcylation of a histone methyltransferase in retinoic-acid-induced granulopoiesis. Nature. May 21, 2009;459(7245):455-9. Epub Apr. 19, 2009.

Gambetta et al., Essential role of the glycosyltransferase sxc/Ogt in polycomb repression. Science. Jul. 3, 2009;325(5936):93-6. Epub May 28, 2009.

Gao et al., Dynamic O-glycosylation of nuclear and cytosolic proteins: cloning and characterization of a neutral, cytosolic beta-N-acetylglucosaminidase from human brain. J Biol Chem. Mar. 30, 2001;276(13):9838-45. Epub Jan. 8, 2001.

(56) References Cited

OTHER PUBLICATIONS

Gloster et al., Glycosidase inhibition: assessing mimicry of the transition state. Org Biomol Chem. Jan. 21, 2010;8(2):305-20. Epub Nov. 5, 2009.
Gloster et al., Hijacking a biosynthetic pathway yields a glycosyltransferase inhibitor within cells. Nat Chem Biol. Mar. 2011;7(3):174-81. Epub Jan. 23, 2011.
Goldberg et al., Posttranslational, reversible O-glycosylation is stimulated by high glucose and mediates plasminogen activator inhibitor-1 gene expression and Sp1 transcriptional activity in glomerular mesangial cells. Endocrinology. Jan. 2006;147(1):222-31.
Golks et al., Requirement for O-linked N-acetylglucosaminyltransferase in lymphocytes activation. EMBO J. Oct. 17, 2007;26(20):4368-79. Epub Sep. 20, 2007.
Golks et al., The O-linked N-acetylglucosamine modification in cellular signalling and the immune system. 'Protein modifications: beyond the usual suspects' review series. EMBO Rep. Aug. 2008;9(8):748-53. Epub Jul. 11, 2008.
Good et al., Hydrogen ion buffers for biological research. Biochemistry. Feb. 1966;5(2):467-77.
Goodford, A computational procedure for determining energetically favorable binding sites on biologically important macromolecules. J Med Chem. Jul. 1985;28(7):849-57.
Goodsell et al., Automated docking of substrates to proteins by simulated annealing. Proteins. 1990;8(3):195-202.
Gorodkin et al., Displaying the information contents of structural RNA alignments: the structure logos. Comput Appl Biosci. Dec. 1997;13(6):583-6.
Gosselin et al., A continuous spectrophotometric assay for glycosyltransferases. Anal Biochem. Jul. 1994;220(1):92-7.
Griffith et al., O-linked N-acetylglucosamine levels in cerebellar neurons respond reciprocally to pertubations of phosphorylation. Eur J Biochem. Jun. 1999;262(3):824-31.
Gross et al., A strategy to discover inhibitors of O-linked glycosylation. J Am Chem Soc. Jan. 16, 2008;130(2):440-1. Epub Dec. 20, 2007.
Gross et al., Discovery of O-GlcNAc transferase inhibitors. J Am Chem Soc. Oct. 26, 2005;127(42):14588-9.
Guan et al., Small interfering RNA-mediated Polo-like kinase 1 depletion preferentially reduces the survival of p53-defective, oncogenic transformed cells and inhibits tumor growth in animals. Cancer Res. Apr. 1, 2005;65(7):2698-704.
Ha et al., The 1.9 Å crystal structure of *Escherichia coli* MurG, a membrane-associated glycosyltransferase involved in peptidoglycan biosynthesis. Protein Sci. Jun. 2000;9(6):1045-52.
Hadjuch et al., A convenient synthesis of the C-1-phosphonate analogue of UDP-GlcNAc and its evaluation as an inhibitor of O-linked GlcNAc transferase (OGT). Carbohydr Res. Feb. 4, 2008;343(2):189-95. Epub Nov. 1, 2007.
Hagen et al., All in the family: the UDP-GalNAc:polypeptide N-acetylgalactosaminyltransferases. Glycobiology. 2003;13(1):1R-16R.
Halgren et al., Glide: a new approach for rapid, accurate docking and scoring. 2. Enrichment factors in database screening. J Med Chem. Mar. 25, 2004;47(7):1750-9.
Haltiwanger et al., Enzymatic addition of O-GlcNAc to nuclear and cytoplasmic proteins. Identification of a uridine diphospho-N-acetylglucosamine:peptide beta-N-acetylglucosaminyltransferase. J Biol Chem. Feb. 15, 1990;265(5):2563-8.
Haltiwanger et al., Glycosylation of nuclear and cytoplasmic proteins. Purification and characterization of a uridine diphospho-N-acetylglucosamine:polypeptide beta-N-acetylglucosaminyltransferase. J Biol Chem. May 5, 1992;267(13):9005-13.
Haltiwanger et al., Modulation of O-linked N-acetylglucosamine levels on nuclear and cytoplasmic proteins in vivo using the peptide O-GlcNAc-beta-N-acetylglucosaminidase inhibitor O-(2-acetamido-2-deoxy-D-glucopyranosylidene)amino-N-phenylcarbamate. J Biol Chem. Feb. 6, 1998;273(6):3611-7.
Hamanaka et al., Polo-like kinase is a cell cycle-regulated kinase activated during mitosis. J Biol Chem. Sep. 8, 1995;270(36):21086-91.
Hang et al., Small molecule inhibitors of mucin-type O-linked glycosylation from a uridine-based library. Chem Biol. Mar. 2004;11(3):337-45.
Hanover et al., A *Caenorhabditis elegans* model of insulin resistance: altered macronutrient storage and dauer formation in an OGT-1 knockout. Proc Natl Acad Sci U S A. Aug. 9, 2005;102(32):11266-71. Epub Jul. 28, 2005.
Hanover, Glycan-dependent signaling: O-linked N-acetylglucosamine. FASEB J. Sep 2001;15(11):1865-76.
Hanover et al., Mitochondrial and nucleocytoplasmic isoforms of O-linked GlcNAc transferase encoded by a single mammalian gene. Arch Biochem Biophys. Jan. 15, 2003;409(2):287-97.
Hart et al., Chapter 18. The O-GlcNAc modification. In: Essentials of glycobiology. Varki et al., eds. Cold Spring Harbor Laboratory Press, Cold Spring Harbor, NY. 2009. 21 pages.
Hart et al., Cycling of O-linked beta-N-acetylglucosamine on nucleocytoplasmic proteins. Nature. Apr. 26, 2007;446(7139):1017-22.
Hart et al., O-GlcNAcylation of key nuclear and cytoskeletal proteins: reciprocity with O-phosphorylation and putative roles in protein multimerization. Glycobiology. Oct. 1996;6(7):711-6.
Hart et al., O-linked N-acetylglucosamine: the "yin-yang" of Ser/Thr phosphorylation? Nuclear and cytoplasmic glycosylation. Glycoimmunology. 1995:115-23.
Hartweck et al., Two O-linked N-acetylglucosamine transferase genes of *Arabidopsis thaliana* L. Heynh. have overlapping functions necessary for gamete and seed development. Genetics. Jul. 2002;161(3):1279-91.
Helm et al., Identification of active-site inhibitors of MurG using a generalizable, high-throughput glycosyltransferase screen. J Am Chem Soc, Sep. 17, 2003;125(37):11168-9.
Hinou et al., Systematic syntheses and inhibitory activities of bisubstrate-type inhibitors of sialyltransferases. J Org Chem. Jul. 11, 2003;68(14):5602-13.
Holt et al., Erythrocytes contain cytoplasmic glycoproteins. O-linked GlcNAc on Band 4.1. J Biol Chem. Nov. 5, 1987;262(31):14847-50.
Housley et al., A PGC-1 alpha-O-GlcNAc transferase complex regulates FoxO transcription factor activity in response to glucose. J Biol Chem. Feb. 20, 2009;284(8):5148-57. Epub Dec. 22, 2008.
Housley et al., O-GlcNAc regulates FoxO activation in response to glucose. J Biol Chem. Jun. 13, 2008;283(24):16283-92. Epub Apr. 17, 2008.
Hu et al., Adenovirus-mediated overexpression of O-GlcNAcase improves contractile function in the diabetic heart. Circ Res. May 13, 2005;96(9):1006-13. Epub Apr. 7, 2005.
Hu et al., Crystal structure of the MurG:UDP-GlcNAc complex reveals common structural principles of a superfamily of glycosyltransferases. Proc Natl Acad Sci U S A. Feb. 4, 2003;100(3):845-9. Epub Jan. 21, 2003.
Hu et al., Identification of selective inhibitors for the glycosyltransferase MurG via high-throughput screening. Chem Biol. May 2004;11(5):703-11.
Huang et al., A Continuous Method for Enzymatic Assay of Sucrose Synthase in the Synthetic Direction. J Agric Food Chem. 1999;47:2746-50.
Hudson et al., Late mitotic failure in mice lacking Sak, a polo-like kinase. Curr Biol. Mar. 20, 2001;11(6):441-6.
Hurtado-Guerrero et al., Molecular mechanisms of O-GlcNAcylation. Curr Opin Struct Biol. Oct. 2008;18(5):551-7. Epub Oct. 6, 2008.
Izumi et al., Bisubstrate analogues as glycosyltransferase inhibitors. Curr Top Med Chem. 2009;9(1):87-105.
Izumi et al., Neutral beta-N-acetylhexosaminidases of rat brain. Purification and enzymatic and immunological characterization. J Biol Chem. Jun. 10, 1983;258(11):6991-9.
Jackson et al., O-glycosylation of eukaryotic transcription factors: implications for mechanisms of transcriptional regulation. Cell. Oct. 7, 1988;55(1):125-33.

(56) References Cited

OTHER PUBLICATIONS

James et al., Flux through the hexosamine pathway is a determinant of nuclear factor kappaB-dependent promoter activation. Diabetes. Apr. 2002;51(4):1146-56.

Jiang et al., A neutral diphosphate mimic crosslinks the active site of human O-GlcNAc transferase. Nat Chem Biol. Nov. 13, 2011;8(1):72-7. doi: 10.1038/nchembio.711.

Jiang et al., A subpopulation of estrogen receptors are modified by O-linked N-acetylglucosamine. J Biol Chem. Jan. 24, 1997;272(4):2421-8.

Jinek et al., The superhelical TPR-repeat domain of O-linked GlcNAc transferase exhibits structural similarities to importin alpha. Nat Struct Mol Biol. Oct. 2004;11(10):1001-7. Epub Sep. 12, 2004.

Jones, A bittersweet modification: O-GlcNAc and cardiac dysfunction. Circ Res. May 13, 2005;96(9):925-6.

Juang et al., Phosphorylation and O-linked glycosylation of Elf-1 leads to its translocation to the nucleus and binding to the promoter of the TCR zeta-chain. J Immunol. Mar. 15, 2002;168(6):2865-71.

Kamemura et al., Dynamic interplay between O-glycosylation and O-phosphorylation of nucleocytoplasmic proteins: alternative glycosylation/phosphorylation of THR-58, a known mutational hot spot of c-Myc in lymphomas, is regulated by mitogens. J Biol Chem. May 24, 2002;277(21):19229-35. Epub Mar. 19, 2002.

Kelly et al., RNA polymerase II is a glycoprotein. Modification of the COOH-terminal domain by O-GlcNAc. J Biol Chem. May 15, 1993;268(14):10416-24.

Khidekel et al., Probing the dynamics of O-GlcNAc glycosylation in the brain using quantitative proteomics. Nat Chem Biol. Jun. 2007;3(6):339-48. Epub May 13, 2007.

Khraltsova et al., An enzyme-linked lectin assay for alpha1,3-galactosyltransferase. Anal Biochem. May 1, 2000;280(2):250-7.

Kiefer et al., The Swiss-Model Repository and associated resources. Nucleic Acids Res. Jan. 2009;37(Database issue):D387-92. Epub Oct. 18, 2008.

Kiessling et al., Chemical approaches to glycobiology. Annu Rev Biochem. 2010;79:619-53.

Kim et al., An O-GlcNAcase-specific inhibitor and substrate engineered by the extension of the N-acetyl moiety. J Am Chem Soc. Apr. 5, 2006;128(13):4234-5.

King et al., Cytokeratin 13 contains O-glycosidically linked N-acetylglucosamine residues. J Biol Chem. Aug. 25, 1989;264(24):14022-8.

Klein et al., O-linked N-acetylglucosamine modification of insulin receptor substrate-1 occurs in close proximity to multiple SH2 domain binding motifs. Mol Cell Proteomics. Dec. 2009;8(12):2733-45. Epub Aug. 11, 2009.

Konrad et al., Alloxan is an inhibitor of the enzyme O-linked N-acetylglucosamine transferase. Biochem Biophys Res Commun. Apr. 26, 2002;293(1):207-12.

Konrad et al., The role of O-linked protein glycosylation in beta-cell dysfunction. Int J Mol Med. Nov. 2002;10(5):535-9.

Koresawa et al., High-throughput screening with quantitation of ATP consumption: a universal non-radioisotope, homogeneous assay for protein kinase. Assay Drug Dev Technol. Apr. 2004;2(2):153-60.

Kreppel et al., Dynamic glycosylation of nuclear and cytosolic proteins. Cloning and characterization of a unique O-GlcNAc transferase with multiple tetratricopeptide repeats. J Biol Chem. Apr. 4, 1997;272(14):9308-15.

Kreppel et al., Regulation of a cytosolic and nuclear O-GlcNAc transferase. Role of the tetratricopeptide repeats. J Biol Chem. Nov. 5, 1999;274(45):32015-22.

Kuntz et al., A geometric approach to macromolecule-ligand interactions. J Mol Biol. Oct. 25, 1982;161(2):269-88.

Lairson et al., Glycosyltransferases: structures, functions, and mechanisms. Annu Rev Biochem. 2008;77:521-55.

Lamarre-Vincent et al., Dynamic glycosylation of the transcription factor CREB: a potential role in gene regulation. J Am Chem Soc. Jun. 4, 2003;125(22):6612-3.

Lane et al., Antibody microinjection reveals an essential role for human polo-like kinase 1 (Plk 1) in the functional maturation of mitotic centrosomes. J Cell Biol. Dec. 1996;135(6 Pt 2):1701-13.

Lazarus et al., Mutational analysis of the catalytic domain of O-linked N-acetylglucosaminyl transferase. J Biol Chem. Oct. 21, 2005;280(42):35537-44. Epub Aug. 16, 2005.

Lazarus et al., Structure of human O-GlcNAc transferase and its complex with a peptide substrate. Nature. Jan. 27, 2011;469(7331):564-7. Epub Jan. 16, 2011.

Leavy et al., A high-throughput assay for O-GlcNAc transferase detects primary sequence preferences in peptide substrates. Bioorg Med Chem Lett. Jul. 15, 2007;17(14):3851-4. Epub May 10, 2007.

Lee et al., A potent and highly selective inhibitor of human alpha-1,3-fucosyltransferase via click chemistry. J Am Chem Soc. Aug. 13, 2003;125(32):9588-9.

Lee et al., Alloxan is an inhibitor of O-GlcNAc-selective N-acetyl-beta-D-glucosaminidase. Biochem Biophys Res Commun. Dec. 1, 2006;350(4):1038-43. Epub Oct. 6, 2006.

Lefebvre et al., Effect of okadaic acid on O-linked N-acetylglucosamine levels in a neuroblastoma cell line. Biochim Biophys Acta. Oct. 18, 1999;1472(1-2):71-81.

Lefebvre et al., Evidence of a balance between phosphorylation and O-GlcNAc glycosylation of Tau proteins—a role in nuclear localization. Biochim Biophys Acta. Jan. 20, 2003;1619(2):167-76.

Lefebvre et al., Identification of N-acetyl-d-glucosamine-specific lectins from rat liver cytosolic and nuclear compartments as heat-shock proteins. Biochem J. Nov. 15, 2001;360(Pt 1):179-88.

Lefebvre et al., The tumor suppressor HIC1 (hypermethylated in cancer I) is O-GlcNAc glycosylated. Eur J Biochem. Oct. 2004;271(19):3843-54.

Lehman et al., A single nucleotide polymorphism in MGEA5 encoding O-GlcNAc-selective N-acetyl-beta-D glucosaminidase is associated with type 2 diabetes in Mexican Americans. Diabetes. Apr. 2005;54(4):1214-21.

Li et al., Function of polo-like kinase 3 in NF-kappaB-mediated proapoptotic response. J Biol Chem. Apr. 29, 2005;280(17):16843-50. Epub Jan. 25, 2005.

Li et al., SAK, a new polo-like kinase, is transcriptionally repressed by p53 and induces apoptosis upon RNAi silencing. Neoplasia. Apr. 2005;7(4):312-23.

Liu et al., Glucose stimulates protein modification by O-linked GlcNAc in pancreatic beta cells: linkage of O-linked GlcNAc to beta cell death. Proc Natl Acad Sci U S A. Mar. 14, 2000;97(6):2820-5.

Liu et al., O-GlcNAcylation regulates phosphorylation of tau: a mechanism involved in Alzheimer's disease. Proc Natl Acad Sci U S A. Jul. 20, 2004;101(29):10804-9. Epub Jul. 12, 2004.

Liu et al., Polo-like kinase (Plk)1 depletion induces apoptosis in cancer cells. Proc Natl Acad Sci U S A. May 13, 2003;100(10):5789-94. Epub May 5, 2003.

Liu et al., The Synthesis and Characterization of a Helical Miniature Protein Mimicking the OGT Active Domain. Int J Pept Res Ther. 2006;12(3):237-41.

Love et al., Dynamic O-GlcNAc cycling at promoters of *Caenorhabditis elegans* genes regulating longevity, stress, and immunity. Proc Natl Acad Sci U S A. Apr. 20, 2010;107(16):7413-8. Epub Apr. 5, 2010.

Love et al., Mitochondrial and nucleocytoplasmic targeting of O-linked GlcNAc transferase. J Cell Sci. Feb. 15, 2003;116(Pt 4):647-54.

Love et al., The hexosamine signaling pathway: deciphering the "O-GlcNAc code".Sci STKE. Nov. 29, 2005;2005(312):re13.

Lowery et al., Structure and function of Polo-like kinases. Oncogene. Jan. 10, 2005;24(2):248-59.

Lowery et al., Transcreener: screening enzymes involved in covalent regulation. Expert Opin Ther Targets. Feb. 2006;10(1):179-90.

Lubas et al., Analysis of nuclear pore protein p62 glycosylation. Biochemistry. Feb. 7, 1995;34(5):1686-94.

Lubas et al., Functional expression of O-linked GlcNAc transferase. Domain structure and substrate specificity. J Biol Chem. Apr. 14, 2000;275(15):10983-8.

Lubas et al., O-Linked GlcNAc transferase is a conserved nucleocytoplasmic protein containing tetratricopeptide repeats. J Biol Chem. Apr. 4, 1997;272(14):9316-24.

(56) References Cited

OTHER PUBLICATIONS

Ma et al., Drug targeting *Mycobacterium tuberculosis* cell wall synthesis: genetics of dTDP-rhamnose synthetic enzymes and development of a microtiter plate-based screen for inhibitors of conversion of dTDP-glucose to dTDP-rhamnose. Antimicrob Agents Chemother. May 2001;45(5):1407-16.

Ma et al., Role of Plk2 (Snk) in mouse development and cell proliferation. Mol Cell Biol. Oct. 2003;23(19):6936-43.

Macauley et al., Increasing O-GlcNAc levels: An overview of small-molecule inhibitors of O-GlcNAcase. Biochim Biophys Acta. Feb. 2010;1800(2):107-21. Epub Aug. 4, 2009.

Macauley et al., O-GlcNAcase uses substrate-assisted catalysis: kinetic analysis and development of highly selective mechanism-inspired inhibitors. J Biol Chem. Jul. 8, 2005;280(27):25313-22. Epub Mar. 28, 2005.

MacMillan et al., Comparative expression of the mitotic regulators SAK and PLK in colorectal cancer. Ann Surg Oncol. Oct. 2001;8(9):729-40.

Majumdar et al., Insulin stimulates and diabetes inhibits O-linked N-acetylglucosamine transferase and O-glycosylation of Sp1. Diabetes. Dec. 2004;53(12):3184-92.

Malinka et al., 2-Substituted-3-oxoisothiazolo[5,4-b]pyridines as potential central nervous system and antimycobacterial agents. Farmaco. Jul. 30, 1998;53(7):504-12.

Marshall et al., Discovery of a metabolic pathway mediating glucose-induced desensitization of the glucose transport system. Role of hexosamine biosynthesis in the induction of insulin resistance. J Biol Chem. Mar. 15, 1991;266(8):4706-12.

Marshall et al., Enhanced expression of uridine diphosphate-N-acetylglucosaminyl transferase (OGT) in a stable, tetracycline-inducible HeLa cell line using histone deacetylase inhibitors: kinetics of cytosolic OGT accumulation and nuclear translocation. Anal Biochem. Aug. 15, 2003;319(2):304-13.

Marshall et al., Measurement of UDP-N-acetylglucosaminyl transferase (OGT) in brain cytosol and characterization of anti-OGT antibodies. Anal Biochem. Mar. 15, 2003;314(2):169-79.

Martin et al., 3D database searching in drug design. J Med Chem. Jun. 12, 1992;35(12):2145-54.

Martinez-Fleites et al., Structural analyses of enzymes involved in the O-GlcNAc modification. Biochim Biophys Acta. Feb. 2010;1800(2):122-33. Epub Jul. 30, 2009.

Martinez-Fleites et al., Structure of an O-GlcNAc transferase homolog provides insight into intracellular glycosylation. Nat Struct Mol Biol. Jul. 2008;15(7):764-5. Epub Jun. 8, 2008.

Martinez-Fleites et al., Structure of an O-GlcNAc transferase homolog provides insight into intracellular glycosylation. Nat Struct Mol Biol. Jul. 2008;15(7):764-5. Epub Jun. 8, 2008. Supplementary Information.

Mathis, Probing molecular interactions with homogeneous techniques based on rare earth cryptates and fluorescence energy transfer. Clin Chem. Sep. 1995;41(9):1391-7.

McCoy et al., Phaser crystallographic software. J Appl Crystallogr. Aug. 1, 2007;40(Pt 4):658-674. Epub Jul. 13, 2007.

McCoy, Solving structures of protein complexes by molecular replacement with Phaser. Acta Crystallogr D Biol Crystallogr. Jan. 2007;63(Pt 1):32-41. Epub Dec. 13, 2006.

Medina et al., SV40 large T antigen is modified with O-linked N-acetylglucosamine but not with other forms of glycosylation. Glycobiology. Apr. 1998;8(4):383-91.

Meikrantz et al., Nuclear localization of an O-glycosylated protein phosphotyrosine phosphatase from human cells. J Cell Sci. Mar. 1991;98 ( Pt 3):303-7.

Miranker et al., Functionality maps of binding sites: a multiple copy simultaneous search method. Proteins. 1991;11(1):29-34.

Mizanur et al., One-step synthesis of labeled sugar nucleotides for protein O-GlcNAc modification studies by chemical function analysis of an archaeal protein. J Am Chem Soc. Jan. 26, 2005;127(3):836-7.

Moura et al., Large scale comparative codon-pair context analysis unveils general rules that fine-tune evolution of mRNA primary structure. PLoS One. Sep. 5, 2007;2(9):e847.

Navaza et al., AmoRE: an Automated Package for Molecular Replacement. Acta Cryst. 1994;A50:157-63.

Navia et al., Use of structural information in drug design. Curr Opin Struct Biol. 1992;2:202-10.

Nishibata et al., Automatic Creation of Drug Candidate Structures Based on Receptor Structure. Starting Point for Artificial Lead Generation. Tetrahedron. 1991;47(43):8985-90.

Nishikata et al., A phosphotyrosine-containing quenched fluorogenic peptide as a novel substrate for protein tyrosine phosphatases. Biochem J. 1999;343:385-91.

Nishikata et al., Continuous assay of protein tyrosine phosphatases based on fluorescence resonance energy transfer. Biochimie. Jul. 2006;88(7):879-86. Epub Feb. 28, 2006.

Nolte et al., Human O-GlcNAc transferase (OGT): genomic structure, analysis of splice variants, fine mapping in Xq13.1. Mamm Genome. Jan. 2002;13(1):62-4.

O'Donnell et al., Ogt-dependent X-chromosome-linked protein glycosylation is a requisite modification in somatic cell function and embryo viability. Mol Cell Biol. Feb. 2004;24(4):1680-90.

Ogawa et al., Profiling terminal N-acetyllactosamines of glycans on mammalian cells by an immuno-enzymatic assay. Glycoconj J. Dec. 2006;23(9):663-74. Epub Nov. 18, 2006.

Ohn et al., A functional RNAi screen links O-GlcNAc modification of ribosomal proteins to stress granule and processing body assembly. Nat Cell Biol. Oct. 2008;10(10):1224-31. Epub Sep. 14, 2008.

Olah et al., Strategies for compound selection. Curr Drug Discov Technol. Oct. 2004;1(3):211-20.

Painter et al., Optimal description of a protein structure in terms of multiple groups undergoing TLS motion. Acta Crystallogr D Biol Crystallogr. Apr. 2006;62(Pt 4):439-50. Epub Mar. 18, 2006.

Painter et al., *TLSMD* web server for the generation of multi-group TLS models. J Appl Cryst. 2006;39:109-11.

Palcic et al., Assays for Glycosyltransferases. Trends in Glycosci and Glycotechnol. 2001;13(72):361-70.

Pape et al., HKL2MAP: a graphical user interface for macromolecular phasing with SHELX programs. J Appl Cryst. 2004;37:843-44.

Parker et al., Insulin resistance of glycogen synthase mediated by o-linked N-acetylglucosamine. J Biol Chem. Mar. 21, 2003;278(12):10022-7. Epub Jan. 1, 2003.

Patti et al., Activation of the Hexosamine Pathway by Glucosamine in Vivo Induces Insulin Resistance of Early Postreceptor Insulin Signaling Events in Skeletal Muscle. Diabetes 1999 v48 p. 1562-71.

Peitsch, Protein modeling by E-mail. Bio/Technol. 1995;13:658-60.

Pesnot et al., Structural and mechanistic basis for a new mode of glycosyltransferase inhibition. Nat Chem Biol. May 2010;6(5):321-3. Epub Apr. 4, 2010.

Potterton et al., Developments in the CCP4 molecular-graphics project. Acta Crystallogr D Biol Crystallogr. Dec. 2004;60(Pt 12 Pt 1):2288-94. Epub Nov. 26, 2004.

Qiu et al., Expressions of polypeptide: N-acetylgalactosaminyltransferase in leukemia cell lines during 1,25-dihydroxyvitamin D3 induced differentiation. Glycoconj J. Nov. 2006;23(7-8):575-84.

Reason et al., Localization of O-GlcNAc modification on the serum response transcription factor. J Biol Chem. Aug. 25, 1992;267(24):16911-21.

Reaven, Pathophysiology of insulin resistance in human disease. Physiol Rev. Jul. 1995;75(3):473-86.

Rempel et al., Covalent inhibitors of glycosidases and their applications in biochemistry and biology. Glycobiology. Aug. 2008;18(8):570-86. Epub May 22, 2008.

Rex-Mathes et al., Immunological detection of O-GlcNAc. Methods Mol Biol. 2002;194:73-87.

Rodems et al., A FRET-based assay platform for ultra-high density drug screening of protein kinases and phosphatases. Assay Drug Dev Technol. Nov. 2002;1(1 Pt 1):9-19.

Rogawski et al., The neuropharmacological basis for the use of memantine in the treatment of Alzheimer's disease. CNS Drug Rev. 2003 Fall;9(3):275-308.

(56) References Cited

OTHER PUBLICATIONS

Roquemore et al., Detection of O-linked N-acetylglucosamine (O-GlcNAc) on cytoplasmic and nuclear proteins. Methods Enzymol. 1994;230:443-60.
Roquemore et al., Dynamic O-GlcNAcylation of the small heat shock protein alpha B-crystallin. Biochemistry. Mar. 19, 1996;35(11):3578-86.
Saotome et al., Combinatorial library of five-membered iminocyclitol and the inhibitory activities against glyco-enzymes. Chem Biol. Nov. 2001;8(11):1061-70.
Sawhney et al., Bioerodible Hydrogels Based on Photopolymerized Poly(ethylene glycol)-co-poly(α-hydroxy acid) Diacrylate Macromers. Macromolecules. 1993;26:581-587.
Schneider et al., Sequence logos: a new way to display consensus sequences. Nucleic Acids Res. Oct. 25, 1990;18(20):6097-100.
Schüttelkopf et al., PRODRG: a tool for high-throughput crystallography of protein-ligand complexes. Acta Crystallogr D Biol Crystallogr. Aug. 2004;60(Pt 8):1355-63. Epub Jul. 21, 2004.
Seidler et al., Identification and prediction of promiscuous aggregating inhibitors among known drugs. J Med Chem. Oct. 9, 2003;46(21):4477-86.
Shaw et al., Regulation of specific DNA binding by p53: evidence for a role for O-glycosylation and charged residues at the carboxy-terminus. Oncogene. Feb. 15, 1996;12(4):921-30.
Shi et al., Protein O-fucosyltransferase 1 is an essential component of Notch signaling pathways. Proc Natl Acad Sci U S A. Apr. 29, 2003;100(9):5234-9. Epub Apr. 15, 2003.
Sim et al., Benzylidene rhodanines as novel inhibitors of UDP-N-acetylmuramate/L-alanine ligase. Bioorg Med Chem Lett. Feb. 25, 2002;12(4):697-9.
Sinclair et al., Drosophila O-GlcNAc transferase (OGT) is encoded by the Polycomb group (PcG) gene, super sex combs (sxc). Proc Natl Acad Sci U S A. Aug. 11, 2009;106(32):13427-32. Epub Jul. 28, 2009.
Skropeta et al., Asymmetric synthesis and affinity of potent sialyltransferase inhibitors based on transition-state analogues. Glycoconj J. 2004;21(5):205-19.
Smith et al., Malignant transformation of mammalian cells initiated by constitutive expression of the polo-like kinase. Biochem Biophys Res Commun. May 19, 1997;234(2):397-405.
Soltero-Higgin et al., Identification of inhibitors for UDP-galactopyranose mutase. J Am Chem Soc. Sep. 1, 2004;126(34):10532-3.
Tai et al., Parallel identification of O-GlcNAc-modified proteins from cell lysates. J Am Chem Soc. Sep. 1, 2004;126(34):10500-1.
Tats et al., Preferred and avoided codon pairs in three domains of life. BMC Genomics. Oct. 8, 2008;9:463.
Tenno et al., Initiation of protein O glycosylation by the polypeptide GalNAcT-1 in vascular biology and humoral immunity. Mol Cell Biol. Dec. 2007;27(24):8783-96. Epub Oct. 8, 2007.
Toleman et al., Characterization of the histone acetyltransferase (HAT) domain of a bifunctional protein with activable O-GlcNAcase and HAT activities. J Biol Chem. Dec. 17, 2004;279(51):53665-73. Epub Oct. 12, 2004.
Topaz et al., Absence of intraepidermal glycosyltransferase ppGalNac-T3 expression in familial tumoral calcinosis. Am J Dermatopathol. Jun. 2005;27(3):211-5.
Torres et al., Topography and polypeptide distribution of terminal N-acetylglucosamine residues on the surfaces of intact lymphocytes. Evidence for O-linked GlcNAc. J Biol Chem. Mar. 10, 1984;259(5):3308-17.
Trunkfield et al., Inhibition of Escherichia coli glycosyltransferase MurG and Mycobacterium tuberculosis Gal transferase by uridine-linked transition state mimics. Bioorg Med Chem. Apr. 1, 2010;18(7):2651-63. Epub Feb. 19, 2010.
Tsokos et al., Activation of the Ets transcription factor Elf-1 requires phosphorylation and glycosylation: defective expression of activated Elf-1 is involved in the decreased TCR zeta chain gene expression in patients with systemic lupus erythematosus. Ann N Y Acad Sci. Apr. 2003;987:240-5.
Turner et al., Cytologic assessment of nuclear and cytoplasmic O-linked N-acetylglucosamine distribution by using anti-streptococcal monoclonal antibodies. Proc Natl Acad Sci U S A. Aug. 1990;87(15):5608-12.
Vocadlo et al., A chemical approach for identifying O-GlcNAc-modified proteins in cells. Proc Natl Acad Sci U S A. Aug. 5, 2003;100(16):9116-21. Epub Jul. 21, 2003.
Vocadlo et al., Mechanistic insights into glycosidase chemistry. Curr Opin Chem Biol. Oct. 2008;12(5):539-55.
Von Ahsen et al., High-throughput screening for kinase inhibitors. Chembiochem. Mar. 2005;6(3):481-90.
Vosseller et al., Elevated nucleocytoplasmic glycosylation by O-GlcNAc results in insulin resistance associated with defects in Akt activation in 3T3-L1 adipocytes. Proc Natl Acad Sci U S A. Apr. 16, 2002;99(8):5313-8.
Vosseller et al., O-linked N-acetylglucosamine proteomics of postsynaptic density preparations using lectin weak affinity chromatography and mass spectrometry. Mol Cell Proteomics. May 2006;5(5):923-34. Epub Feb. 1, 2006.
Wagner et al., Glycosyltransferases and their assays. Chembiochem. Sep. 24, 2010;11(14):1939-49.
Walgren et al., High glucose and insulin promote O-GlcNAc modification of proteins, including alpha-tubulin. Am J Physiol Endocrinol Metab. Feb. 2003;284(2):E424-34. Epub Oct. 22, 2002.
Wang et al., A search for pyrophosphate mimics for the development of substrates and inhibitors of glycosyltransferases. Bioorg Med Chem. Apr. 1997;5(4):661-72.
Wang et al., Enrichment and site mapping of O-linked N-acetylglucosamine by a combination of chemical/enzymatic tagging, photochemical cleavage, and electron transfer dissociation mass spectrometry. Mol Cell Proteomics. Jan. 2010;9(1):153-60. Epub Aug. 19, 2009.
Wang et al., Extensive crosstalk between O-GlcNAcylation and phosphorylation regulates cytokinesis. Sci Signal. Jan. 12, 2010;3(104):ra2.
Weichert et al., Polo-like kinase isoform expression is a prognostic factor in ovarian carcinoma. Br J Cancer. Feb. 23. 2004;90(4):815-21.
Weichert et al., Polo-like kinase isoforms in breast cancer: expression patterns and prognostic implications. Virchows Arch. Apr. 2005;446(4):442-50. Epub Mar. 23, 2005.
Wells et al., A role for N-acetylglucosamine as a nutrient sensor and mediator of insulin resistance. Cell Mol Life Sci. Feb. 2003;60(2):222-8.
Wells et al., Dynamic O-glycosylation of nuclear and cytosolic proteins: further characterization of the nucleocytoplasmic beta-N-acetylglucosaminidase, O-GlcNAcase. J Biol Chem. Jan. 18, 2002;277(3):1755-61.
Wells et al., Glycosylation of nucleocytoplasmic proteins: signal transduction and O-GlcNAc. Science. Mar. 23, 2001;291(5512):2376-8.
Wells et al., Mapping sites of O-GlcNAc modification using affinity tags for serine and threonine post-translational modifications. Mol Cell Proteomics. Oct. 2002;1(10):791-804.
Wells et al., O-GlcNAc transferase is in a functional complex with protein phosphatase 1 catalytic subunits. J Biol Chem. Sep. 10, 2004;279(37):38466-70. Epub Jul. 7, 2004.
Wesche et al., High throughput screening for protein kinase inhibitors. Comb Chem High Throughput Screen. Mar. 2005;8(2):181-95.
Wilen et al., Strategies in Optical Resolutions. Tetrahedron. 1977;33:2725-36.
Wilen, Tables of Resolving Agents and Optical Resolutions. E.L. Eliel, ed. Universtify of Notre Dame Press, Notre Dame, IN. 1972:268-98.
Wongkongkatep et al., Label-free, real-time glycosyltransferase assay based on a fluorescent artificial chemosensor. Angew Chem Int Ed Engl. Jan. 16, 2006;45(4):665-8.
Wrabl et al., Homology between O-linked GlcNAc transferases and proteins of the glycogen phosphorylase superfamily. J Mol Biol. Nov. 30, 2001;314(3):365-74.
Xu et al., A bioluminescence resonance energy transfer (BRET) system: application to interacting circadian clock proteins. Proc Natl Acad Sci U S A. Jan. 5, 1999;96(1):151-6.

(56) References Cited

OTHER PUBLICATIONS

Yang et al., Modification of p53 with O-linked N-acetylglucosamine regulates p53 activity and stability. Nat Cell Biol. Oct. 2006;8(10):1074-83. Epub Sep. 10, 2006.

Yang et al., O-linkage of N-acetylglucosamine to Sp1 activation domain inhibits its transcriptional capability. Proc Natl Acad Sci U S A. Jun. 5, 2001;98(12):6611-6. Epub May 22, 2001.

Yang et al., Phosphoinositide signalling links O-GlcNAc transferase to insulin resistance. Nature. Feb. 21, 2008;451(7181):964-9.

Yang et al., Recruitment of O-GlcNAc transferase to promoters by corepressor mSin3A: coupling protein O-GlcNAcylation to transcriptional repression. Cell. Jul. 12, 2002;110(1):69-80.

Zachara et al., O-GlcNAc a sensor of cellular state: the role of nucleocytoplasmic glycosylation in modulating cellular function in response to nutrition and stress. Biochim Biophys Acta. Jul. 6, 2004;1673(1-2):13-28.

Zachara et al., The emerging significance of O-GlcNAc in cellular regulation. Chem Rev. Feb. 2002; 102(2):431-8.

Zhang et al., A Modified Coupled Enzyme Method for O-linked GlcNAc Transferase Activity Assay. Biol Proced Online. Dec. 3, 2009;11:170-83.

Zhang et al., O-GlcNAc modification is an endogenous inhibitor of the proteasome. Cell. Dec. 12, 2003;115(6):715-25.

Extended European Search Report for EP 10783701.5, mailed Mar. 20, 2013.

International Preliminary Report on Patentability for PCT/US2011/051431, mailed Mar. 28, 2013.

International Search Report and Written Opinion for PCT/US2012/045675, mailed Nov. 22, 2012.

Office Communication, mailed Aug. 16, 2012, for U.S. Appl. No. 12/226,151.

Office Communication, mailed Dec. 28, 2012, for U.S. Appl. No. 12/664,559.

Notice of Allowance, mailed May 1, 2013, for U.S. Appl. No. 12/664,559.

Database Registry [Online] Chemical Abstracts Service, Columbus, Ohio, US; Database accession No. 1094798-35-2; Jan. 21, 2009.

Botella et al., Aminolyse de carbamates cycliques analogues de la carboxybiotine ; catalyse métallique et modelisation de transfert de carboxyle. Tetrahedron. 1992;48(24):5111-22. French. Retrieved from DB ACS on STN CA: 117:110975, compound with RN 27087-39-4.

Kozarsky et al., Use of a mutant cell line to study the kinetics and function of O-linked glycosylation of low density lipoprotein receptors. Proc Natl Acad Sci U S A. Jun. 1988;85(12):4335-9.

Nishio et al., Acylation and Alkoxycarbonylation of Benzoxazoline-2-thione and Benzothiazoline-2-thione. Heterocycles. 2004;62(1):313-324.

Novak et al., Heterogeneity of O-glycosylation in the hinge region of human IgA1. Mol Immunol. Dec. 2000;37(17):1047-56.

Poznanskaya et al., New derivatives of benzoxazolinones and benzoxazolinethiones. I. Synthesis and acylating activity of N-aryloxycarbony 1-2-benzoxazolinones. Khimiya Geterotsiklicheskikh Soedinenii. 1969;6:965-7. Russian. Retrieved from DB ACS on STN CA: 72:121409, compounds with RN 27087-35-0, 27087-36-1, 27087-37-2, 27087-38-3, 27087-39-4, 27087-40-7, 27087-41-8, 27087-42-9, 27087-43-0.

Pratt et al., Deconvoluting the functions of polypeptide N-alpha-acetylgalactosaminyltransferase family members by glycopeptide substrate profiling. Chem Biol. Jul. 2004;11(7):1009-16.

\* cited by examiner

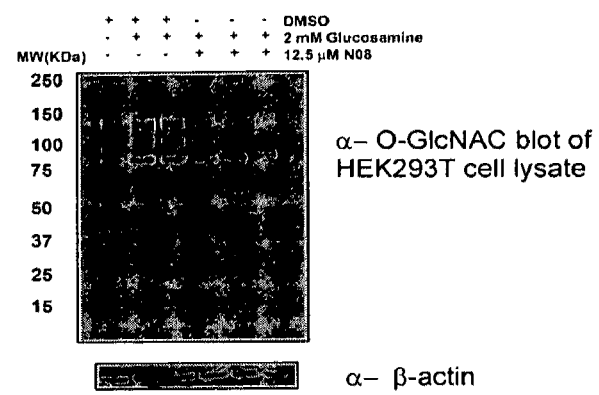

O-GLCNAC TRANSFERASE INHIBITORS AND USES THEREOF

RELATED APPLICATIONS

The present application is a national stage filing under 35 U.S.C. §371 of international PCT application, PCT/US2010/001596, filed Jun. 1, 2010, which claims priority under 35 U.S.C. §119(e) to U.S. provisional patent application, U.S. Ser. No. 61/217,514, filed Jun. 1, 2009, each of which is incorporated herein by reference.

BACKGROUND OF THE INVENTION

The hexosamine biosynthetic pathway (HSP) is a minor branch of the glycolytic pathway, diverting 3-5% of cellular glucose toward the synthesis of UDP-GlcNAc, which is either transported to the Golgi and used in the synthesis of complex glycans or remains in the cytoplasm where it is the substrate for O-GlcNAc transferase (OGT). OGT is the sole known enzyme to catalyze the glycosylation of serine and threonine residues on many nuclear and cytoplasmic proteins (termed O-GlcNAcylation). This post-translational modification is dynamic and is a general mechanism, like protein phosphorylation, of signal transduction.

Excess flux through the HSP has been implicated in both the early (insulin resistance) and late (nephropathy, microvascular damage) stages of diabetes mellitus, both in vivo and in vitro. Diabetes involves a deficiency in the availability and/or utilization of insulin. Insulin is a hormone produced by the pancreas and is necessary for cells to utilize glucose. Insulin resistance is a condition in which muscle, fat, and liver cells do not use insulin properly. As a result, the pancreas produces more insulin, which is also not used properly. Eventually, the pancreas cannot keep up with the body's need for insulin, and excess glucose builds up in the bloodstream. Thus, in insulin resistance, there may be high levels of blood glucose and high levels of insulin circulating in the bloodstream at the same time.

Experiments have shown that insulin resistance due to increased hexosamine flux is caused by hyper O-GlcNAcylation. Diabetics have increased production of two adipokines directly responsible for vascular injury, plasminogen activator inhibitor-1 (PAI-1) and transforming growth factor β1 (TGF-β1). Transcription of both of these proteins is decreased in cell culture when levels of O-GlcNAcylation are decreased. The molecular mechanism for this is known; increased transcription is mediated by the O-GlcNAcylation state of the transcription factor Sp1.

OGT activity and O-GlcNAcylation have also been implicated in other disease states, such as neurodegenerative diseases, cancer, autoimmune diseases, and inflammatory diseases. Accordingly, there is a need to find OGT inhibitors useful as therapeutic agents.

SUMMARY OF THE INVENTION

The invention relates in part to compounds that inhibit O-GlcNAc transferase (OGT) activity. The inventive compounds are based on hits identified in a screen of over 1200 compounds for their ability to inhibit OGT. Compounds of the invention inhibit O-GlcNAcylation by OGT. O-GlcNAcylation is the glycosylation of serine and/or threonine residues on nuclear and cytoplasmic proteins that is catalyzed by OGT. Compounds of the invention are useful for the treatment of diseases and disorders associated with hyper-O-GlcNAcylation (e.g., diabetes and complications thereof, cancers, neurodegenerative diseases, autoimmune diseases, and inflammatory diseases).

In one aspect, inventive compounds are generally of formula (I):

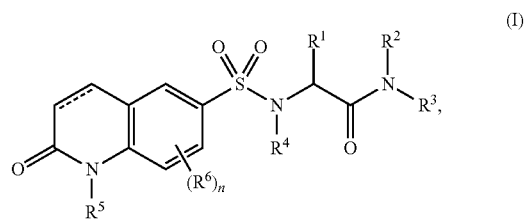

or a pharmaceutically acceptable salt thereof, wherein:

--- denotes a single or double bond;

$R^1$ is cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; substituted or unsubstituted, branched or unbranched arylalkyl; or substituted or unsubstituted, branched or unbranched heteroarylalkyl;

$R^2$ and $R^3$ are independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; substituted or unsubstituted, branched or unbranched arylalkyl; substituted or unsubstituted, branched or unbranched heteroarylalkyl; —C(=O)$R^B$; —SO$R^B$; —SO$_2R^B$; or —C($R^B$)$_3$; wherein each occurrence of $R^B$ is independently hydrogen; halogen; a protecting group; aliphatic; heteroaliphatic; acyl; aryl; heteroaryl; hydroxy; alkoxy; aryloxy; amino; alkylamino; dialkylamino; or heteroaryloxy; or $R^2$ and $R^3$ may optionally be taken together with the intervening nitrogen to form a saturated or unsaturated, substituted or unsubstituted heterocyclic moiety;

$R^4$ is hydrogen, $C_{1-6}$ aliphatic, or a protecting group;

$R^5$ is hydrogen, $C_{1-6}$ aliphatic, or a protecting group;

$R^6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R^F$; —C(=O)$R^F$; —CO$_2R^F$; —C(=O)N($R^F$)$_2$; —CN; —SCN; —S$R^F$; —SO$R^E$; —SO$_2R^F$; —NO$_2$; —N($R^F$)$_2$; —NHC(O)$R^F$; or —C($R^F$)$_3$; wherein each occurrence of $R^F$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy; and n is 0, 1, 2, or 3.

In another aspect, the present invention provides methods of treatment comprising administering an inventive compound to a subject. The compounds of the invention or pharmaceutical compositions thereof may be used to treat any disease including diabetes and complications thereof, insulin resistance, neurodegenerative diseases such as Alzheimer's disease, cancer, autoimmune diseases, and inflammatory diseases. The compounds of the invention may be used to treat disease in humans and other animals including domesticated or experimental animals. The inventive compounds may also be used as probes of biological pathways.

In yet another aspect, the present invention provides pharmaceutical compositions comprising the inventive compounds. The composition typically comprises a therapeutically effective amount of an inventive compound to inhibit OGT and/or treat diabetes and complications thereof, insulin resistance, neurodegenerative diseases such as Alzheimer's disease, cancer, autoimmune diseases, and inflammatory diseases. The pharmaceutical compositions may optionally include a pharmaceutically acceptable excipient. Any mode of administration including oral, parenteral, and topical administration of the inventive compound or pharmaceutical composition thereof may be used.

References cited in this application are incorporated herein by reference.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972).

It will be appreciated that the compounds of the present invention, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The present invention contemplates any and all such combinations in order to arrive at a stable substituent/moiety. Additional examples of generally applicable substitutents are illustrated by the specific embodiments shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety.

As used herein, substituent names which end in the suffix "-ene" refer to a biradical derived from the removal of two hydrogen atoms from the substitutent. Thus, for example, acyl is acylene; alkyl is alkylene; alkeneyl is alkenylene; alkynyl is alkynylene; heteroalkyl is heteroalkylene, heteroalkenyl is heteroalkenylene, heteroalkynyl is heteroalkynylene, aryl is arylene, and heteroaryl is heteroarylene.

The term "acyl," as used herein, refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula (—$OR^i$), wherein $R^i$ is an optionally substituted acyl group, as defined herein, and the oxygen moiety is directly attached to the parent molecule.

The term "aliphatic," as used herein, includes both saturated and unsaturated, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "amino," as used herein, refers to a group of the formula (—$NH_2$). A "substituted amino" refers either to a mono-substituted amine (—$NHR^h$) of a disubstituted amine (—$NR^h_2$), wherein the $R^h$ substituent is any substitutent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the $R^h$ substituents of the di-substituted amino group (—$NR^h{}_2$) form a 5- to 6-membered heterocyclic ring.

The term "alkoxy" refers to a "substituted hydroxyl" of the formula (—$OR^i$), wherein $R^i$ is an optionally substituted alkyl group, as defined herein, and the oxygen moiety is directly attached to the parent molecule.

The term "alkylthioxy" refers to a "substituted thiol" of the formula (—$SR^r$), wherein $R^r$ is an optionally substituted alkyl group, as defined herein, and the sulfur moiety is directly attached to the parent molecule.

The term "alkylamino" refers to a "substituted amino" of the formula (—$NR^h{}_2$), wherein $R^h$ is, independently, a hydrogen or an optionally substituted alkyl group, as defined herein, and the nitrogen moiety is directly attached to the parent molecule.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylalkyl," as used herein, refers to an aryl substituted alkyl group, wherein the terms "aryl" and "alkyl" are defined herein, and wherein the aryl group is attached to the alkyl group, which in turn is attached to the parent molecule. An exemplary arylalkyl group includes benzyl.

The term "aryloxy" refers to a "substituted hydroxyl" of the formula (—$OR^i$), wherein $R^i$ is an optionally substituted aryl group, as defined herein, and the oxygen moiety is directly attached to the parent molecule.

The term "arylamino," refers to a "substituted amino" of the formula (—$NR^h{}_2$), wherein $R^h$ is, independently, a hydrogen or an optionally substituted aryl group, as defined herein, and the nitrogen moiety is directly attached to the parent molecule.

The term "arylthioxy" refers to a "substituted thiol" of the formula (—$SR^r$), wherein $R^r$ is an optionally substituted aryl group, as defined herein, and the sulfur moiety is directly attached to the parent molecule.

The term "azido," as used herein, refers to a group of the formula (—$N_3$).

The term "cyano," as used herein, refers to a group of the formula (—CN).

The terms "halo" and "halogen" as used herein refer to an atom selected from fluorine (fluoro, —F), chlorine (chloro, —Cl), bromine (bromo, —Br), and iodine (iodo, —I).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl," as used herein, refers to an alkyl moiety, as defined herein, which contain one or more oxygen, sulfur, nitrogen, phosphorus, or silicon atoms, e.g., in place of carbon atoms.

The term "heteroalkenyl," as used herein, refers to an alkenyl moiety, as defined herein, which contain one or more oxygen, sulfur, nitrogen, phosphorus, or silicon atoms, e.g., in place of carbon atoms.

The term "heteroalkynyl," as used herein, refers to an alkynyl moiety, as defined herein, which contain one or more oxygen, sulfur, nitrogen, phosphorus, or silicon atoms, e.g., in place of carbon atoms.

The term "heteroalkylamino" refers to a "substituted amino" of the formula (—$NR^h{}_2$), wherein $R^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula (—$OR^i$), wherein $R^i$ is an optionally substituted heteroalkyl group, as defined herein, and the oxygen moiety is directly attached to the parent molecule.

The term "heteroalkylthioxy" refers to a "substituted thiol" of the formula (—$SR^r$), wherein $R^r$ is an optionally substituted heteroalkyl group, as defined herein, and the sulfur moiety is directly attached to the parent molecule.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylamino" refers to a "substituted amino" of the ($-NR^h_2$), wherein $R^h$ is, independently, a hydrogen or an optionally substituted heteroaryl group, as defined herein, and the nitrogen moiety is directly attached to the parent molecule.

The term "heteroaryloxy" refers to a "substituted hydroxyl" of the formula ($-OR^i$), wherein $R^i$ is an optionally substituted heteroaryl group, as defined herein, and the oxygen moiety is directly attached to the parent molecule.

The term "heteroarylthioxy" refers to a "substituted thiol" of the formula ($-SR^r$), wherein $R^r$ is an optionally substituted heteroaryl group, as defined herein, and the sulfur moiety is directly attached to the parent molecule.

The term "hydroxy," or "hydroxyl," as used herein, refers to a group of the formula ($-OH$). A "substituted hydroxyl" refers to a group of the formula ($-OR^i$), wherein $R^i$ can be any substituent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino," as used herein, refers to a group of the formula ($=NR^r$), wherein $R^r$ corresponds to hydrogen or any substitutent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted). In certain embodiments, imino refers to $=NH$ wherein $R^r$ is hydrogen.

The term "isocyano," as used herein, refers to a group of the formula ($-NC$).

The term "nitro," as used herein, refers to a group of the formula ($-NO_2$).

The term "oxo," as used herein, refers to a group of the formula ($=O$).

The term "stable moiety," as used herein, preferably refers to a moiety which possess stability sufficient to allow manufacture, and which maintains its integrity for a sufficient period of time to be useful for the purposes detailed herein.

A "suitable amino protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl) propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable carboxylic acid protecting group," or "protected carboxylic acid," as used herein, are well known in the art and include those described in detail in Greene (1999). Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "suitable hydroxyl protecting group" as used herein, is well known in the art and include those described in detail in Greene (1999). Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

A "suitable thiol protecting group," as used herein, are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected thiol groups further include, but are not limited to, thioesters, carbonates, sulfonates allyl thioethers, thioethers, silyl thioethers, alkyl thioethers, arylalkyl thioethers, and alkyloxyalkyl thioethers. Examples of suitable ester groups include formates, acetates, propionates, pentanoates, crotonates, and benzoates. Specific examples of suitable ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl groups include trimethylsilyl, triethylsilyl, t-butyldimethylsilyl, t-butyldiphenylsilyl, triisopropylsilyl ether, and other trialkylsilyl ethers. Examples of suitable alkyl groups include methyl, benzyl, p-methoxybenzyl, 3,4-dimethoxybenzyl, trityl, t-butyl, and allyl ether, or derivatives thereof. Examples of suitable arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

The term "thio," or "thiol," as used herein, refers to a group of the formula (—SH). A "substituted thiol" refers to a group of the formula (—SR$^r$), wherein R$^r$ can be any substituent that results in the formation of a stable moiety (e.g., a suitable thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "thiooxo," as used herein, refers to a group of the formula (═S).

As used herein, the term "pharmaceutically acceptable salt" refers to those salts which are, within the scope of sound medical judgment, suitable for use in contact with the tissues of humans and lower animals without undue toxicity, irritation, immunological response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "subject," as used herein, refers to any animal. In certain embodiments, the subject is a mammal. In certain embodiments, the term "subject", as used herein, refers to a human (e.g., male, female, adult, or child). The subject may be at any stage of development.

The terms "administer," "administering," or "administration," as used herein refers to implanting, absorbing, ingesting, injecting, or inhaling the inventive compound.

As used herein the term "inhibit" means to reduce the amount of OGT activity and/or O-GlcNAcylation to a level or amount that is statistically significantly less than an initial level, which may be a baseline level of OGT activity and/or O-GlcNAcylation.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The terms "effective amount" and "therapeutically effective amount," as used herein, refer to the amount or concentration of an inventive compound, that, when administered to a subject, is effective to at least partially treat a condition from which the subject is suffering.

As used herein, the terms "O-GlcNAcylation-associated disease or disorder" and "OGT-associated disease or disorder" include, but are not limited to diseases and disorders in which there is abnormal OGT activity and/or abnormal levels of O-GlcNAcylation. As used herein, the term "OGT activity" means OGT-mediated O-GlcNAcylation. An abnormal level of OGT activity and/or O-GlcNAcylation may be a level that is higher than a normal level or may be a level that is lower than a normal level, wherein a "normal" level is the level in a subject who does not have a disease or disorder associated with OGT activity or O-GlcNAcylation. Examples of diseases and disorders associated with OGT activity and/or O-GlcNAcylation levels include, but are not limited to neurodegenerative disorders such as Alzheimer's disease; cancer; diabetes mellitus, insulin resistance, and complications of diabetes or other OGT-associated diseases.

As used herein, the term "complication of diabetes" is used to mean a disorder that is associated with diabetes. Non-limiting examples of complications of diabetes include microvascular damage, insulin resistance, vascular damage, nephropathy, skin ulcers, circulatory damage, diabetic nephropathy, diabetic retinopathy, macro-vascular disease, microvascular disease, cardiac dysfunction, and diabetic neuropathy.

The term "diabetic" as used herein, means a subject who, at the time the sample is taken, has a primary deficiency of insulin. The term diabetic includes, but is not limited to, individuals with juvenile diabetes (Type 1 diabetes), adult-onset diabetes (Type 2 diabetes), gestational diabetes, and any other conditions of insulin deficiency. The terms "diabetic" and "diabetes" are terms of art, known and understood by those practicing in the medical profession, a formal definition of which can be found in *Harrison's Principles of Medicine* (Harrisons, Vol 14, *Principles of Internal Medicine*, Eds. Fauci, A. S., E. Braunwald, K. J. Isselbacher, J. D. Wilson, J. B. Martin, D. L. Kasper, S. L. Hauser, D. L. Longo, McGraw-Hill, New York, 1999).

Subjects with blood glucose levels that are higher than normal but not yet in the range associated with a diagnosis of diabetes may be considered to have "pre-diabetes." Pre-diabetes is also known in the art as "impaired fasting glucose" (IFG) or "impaired glucose tolerance" (IGT). Subjects with pre-diabetes have a higher risk of developing type 2 diabetes, which is also known as adult-onset diabetes or noninsulin-dependent diabetes.

"Insulin resistance," as used herein, is a condition in which the tissues of the body fail to respond normally to insulin. DeFronzo, R. A. *J. Cardiomuscular Pharmacology* 20 (Suppl. 11): S1-S16 (1992). Insulin resistance manifests itself in pathologically elevated endogenous insulin and glucose levels and predisposes one who suffers from said resistance to the development of a cluster of abnormalities, including some degree of impaired glucose tolerance, an increase in plasma triglycerides and low density lipoprotein cholesterol (LDL) levels, a decrease in high-density lipoprotein cholesterol (HDL) levels, high blood pressure, hyperuricemia, a decrease in plasma fibrinolytic activity, an increase in cardiovascular disease and atherosclerosis. Reaven, G. M. *Physiol-Rev.* 75(3): 473-86 (1995).

"Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Carcinomas are malignant cancers that arise from epithelial cells and include adenocarcinoma and squamous cell carcinoma. Sarcomas are cancer of the connective or supportive tissue and include osteosarcoma, chondrosarcoma and gastrointestinal stromal tumor. Hematopoietic cancers, such as leukemia, are able to outcompete the normal hematopoietic compartments in a subject, thereby leading to hematopoietic failure (in the form of anemia, thrombocytopenia and neutropenia) ultimately causing death. A person of ordinary skill in the art can classify a cancer as a sarcoma, carcinoma or hematopoietic cancer.

BRIEF DESCRIPTION OF THE DRAWING

FIG. 1. N-(furan-2-ylmethyl)-2-(2-oxo-1,2-dihydroquinoline-6-sulfonamido)-2-phenyl-N-(thiophen-2-ylmethyl)acetamide (inhibitor N08) reduces glucosamine-induced cellular-wide O-GlcNAcylation changes to normal levels in HEK cells.

DETAILED DESCRIPTION OF CERTAIN EMBODIMENTS OF THE INVENTION

The present invention provides inhibitors of O-GlcNAc transferase. The inventive compounds typically include a quinolinone or dihydroquinolinone core as shown herein. The compounds of the present invention are useful in the treatment of OGT-related diseases or disorders. Specifically, the compounds are useful in the treatment of diabetes and complications thereof, neurological diseases, cancers, and autoimmune diseases, and inflammatory diseases. The present invention also provides pharmaceutical compositions and methods of using the inventive compounds for the treatment of various diseases.

Compounds

Compounds of the present invention include inhibitors of OGT. In certain embodiments, the compounds have an $IC_{50}$ of less than approximately 100 µM, e.g., less than approximately 10 µM, e.g., less than approximately 1 µM, e.g., less than approximately 0.1 µM, or e.g., less than approximately 0.01 µM. The inventive compounds may be useful in the treatment of a variety of diseases. In certain embodiments, the compounds are useful in the treatment of diabetes and complications thereof, and insulin resistance. Certain compounds are also useful in treating neurological diseases, such as neurodegenerative diseases. In certain embodiments, the compounds are useful in the treatment of certain types of cancers. In other embodiments, the compounds are useful in treating autoimmune diseases or inflammatory diseases.

In certain embodiments, the invention provides a compound of formula (I) or a pharmaceutically acceptable salt thereof:

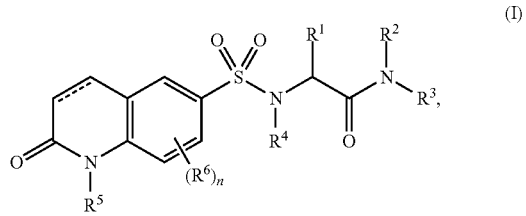

(I)

wherein:

—— denotes a single or double bond;

$R^1$ is cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; substituted or unsubstituted, branched or unbranched arylalkyl; or substituted or unsubstituted, branched or unbranched heteroarylalkyl;

$R^2$ and $R^3$ are independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; substituted or unsubstituted, branched or unbranched arylalkyl; substituted or unsubstituted, branched or unbranched heteroarylalkyl; —C(=O)$R^B$; —SO$R^B$; —SO$_2R^B$; or —C($R^B$)$_3$; wherein each occurrence of $R^B$ is independently hydrogen; halogen; a protecting group; aliphatic; heteroaliphatic; acyl; aryl; heteroaryl; alkoxy; aryloxy; amino; alkylamino; dialkylamino; or heteroaryloxy; or $R^2$ and $R^3$ may optionally be taken together with the intervening nitrogen to form a saturated or unsaturated, substituted or unsubstituted heterocyclic moiety;

$R^4$ is hydrogen, $C_{1-6}$ aliphatic, or a protecting group;

$R^5$ is hydrogen, $C_{1-6}$ aliphatic, or a protecting group;

$R^6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R^F$; —C(=O)$R^F$; —CO$_2R^F$; —C(=O)N($R^F$)$_2$; —CN; —SCN; —S$R^F$; —SO$R^E$; —SO$_2R^F$; —NO$_2$; —N($R^F$)$_2$; —NHC(O)$R^F$; or —C($R^F$)$_3$; wherein each occurrence of $R^F$ is independently hydrogen; halogen; a protecting group; aliphatic; heteroaliphatic; acyl; aryl moiety; heteroaryl; alkoxy; aryloxy; alkylthioxy; arylthioxy; amino; alkylamino; dialkylamino; heteroaryloxy; or heteroarylthioxy; and n is 0, 1, 2, or 3.

In certain embodiments, the compound of formula I is not one of the following compounds:

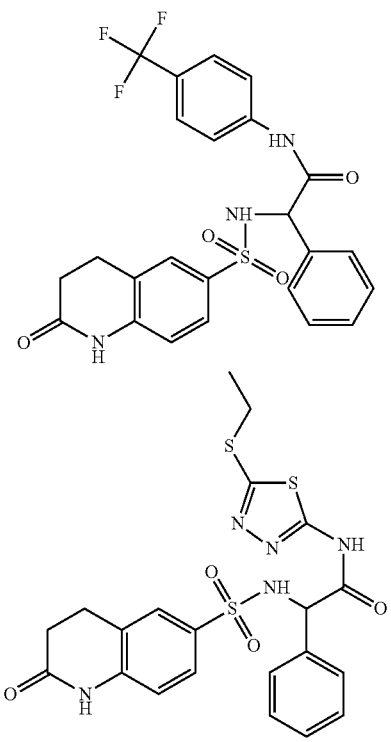

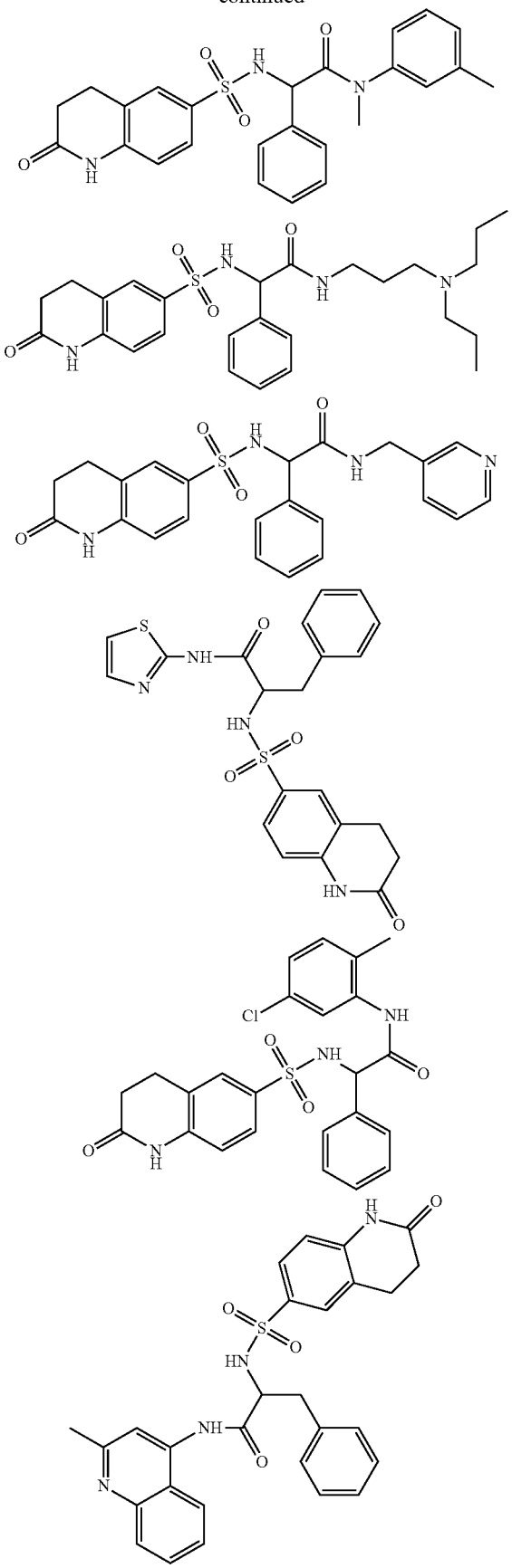
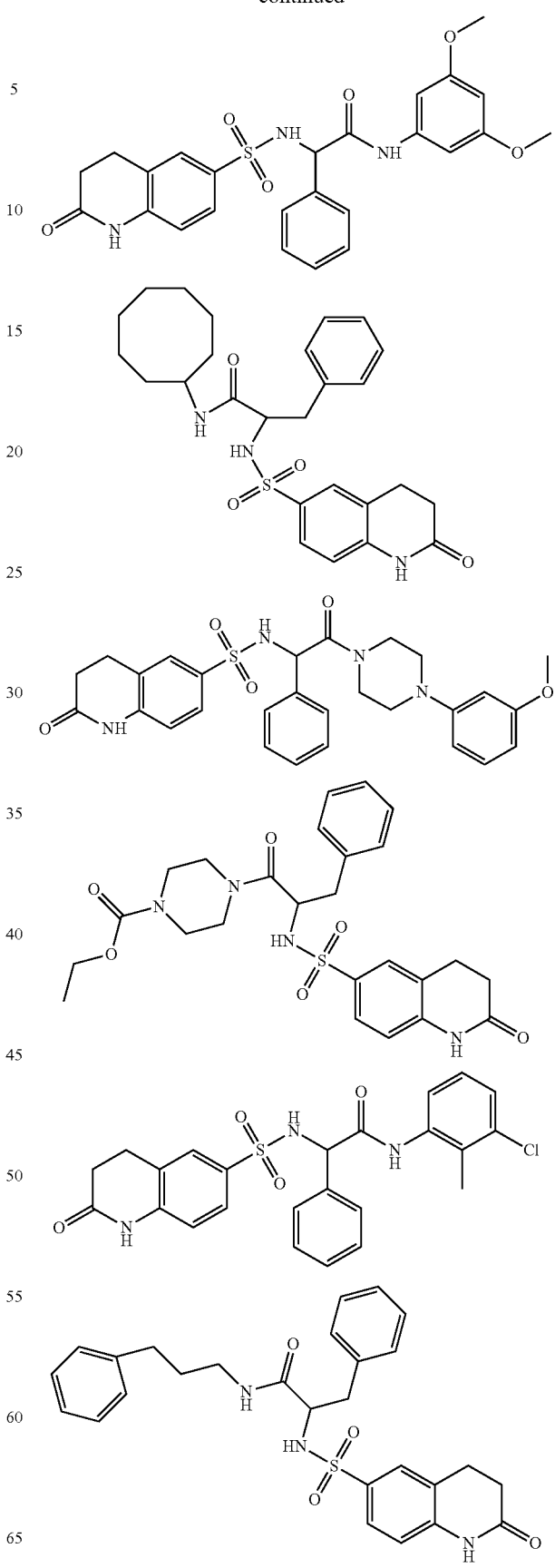

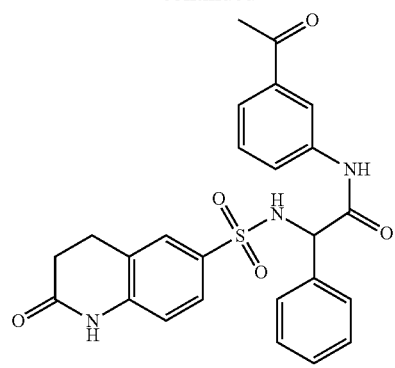
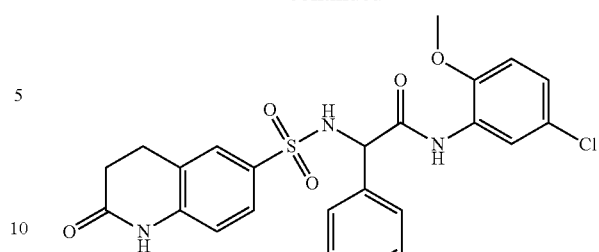
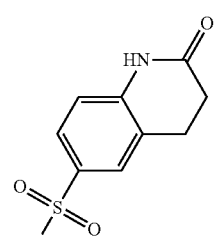
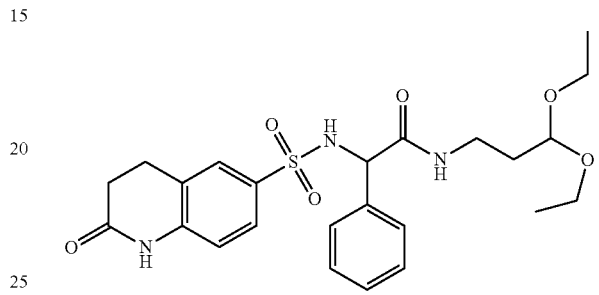
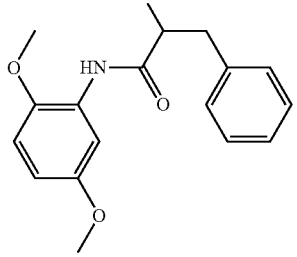
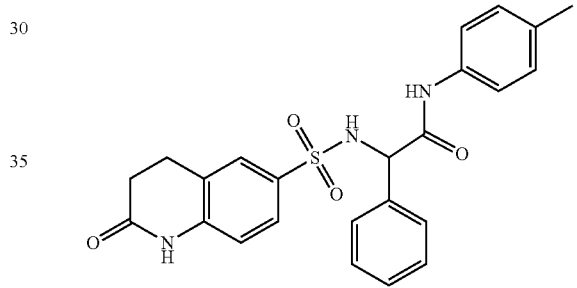
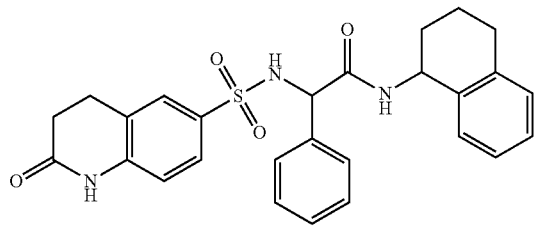
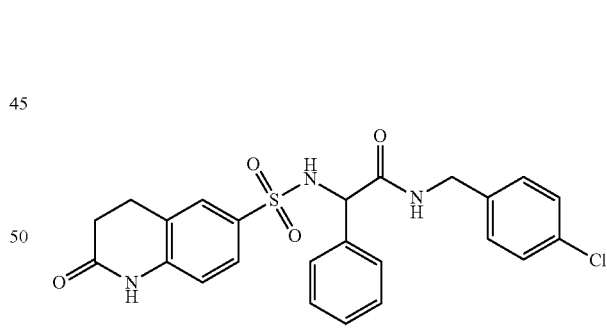
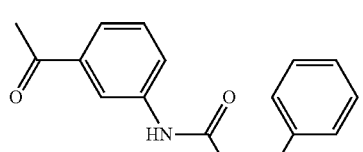
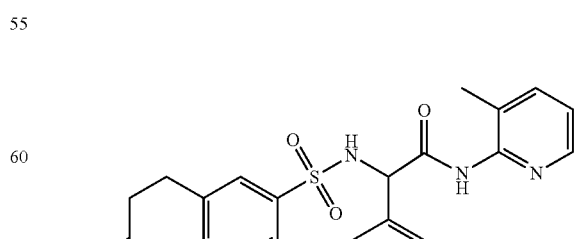
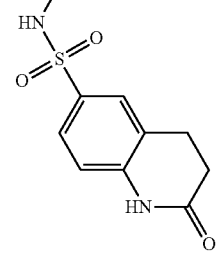

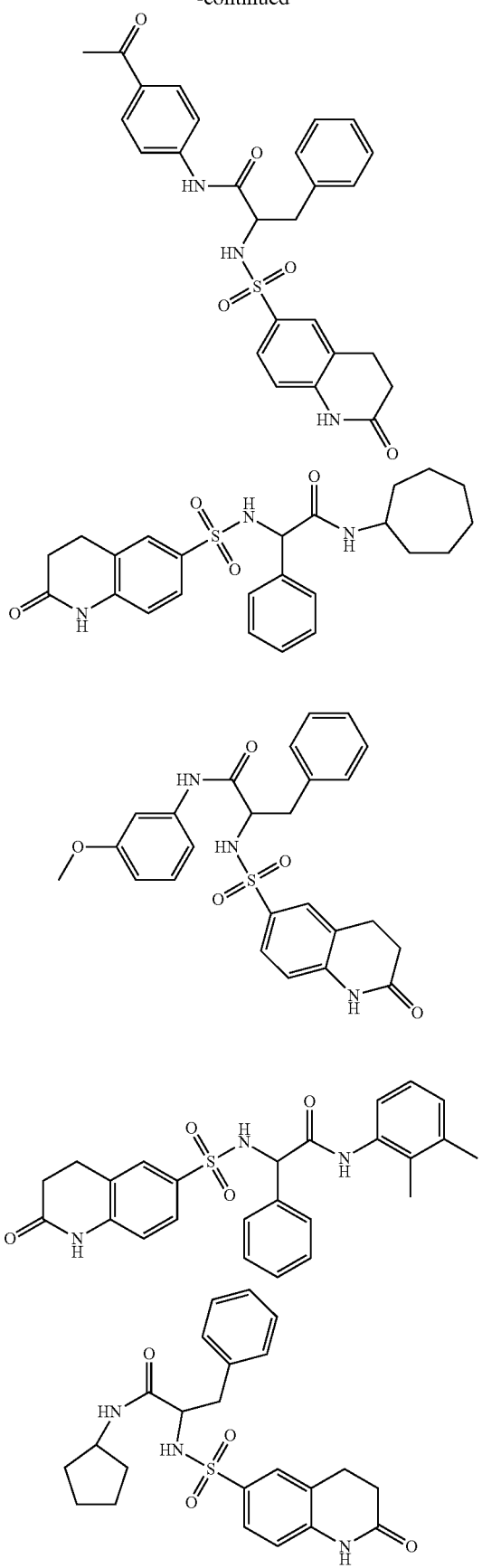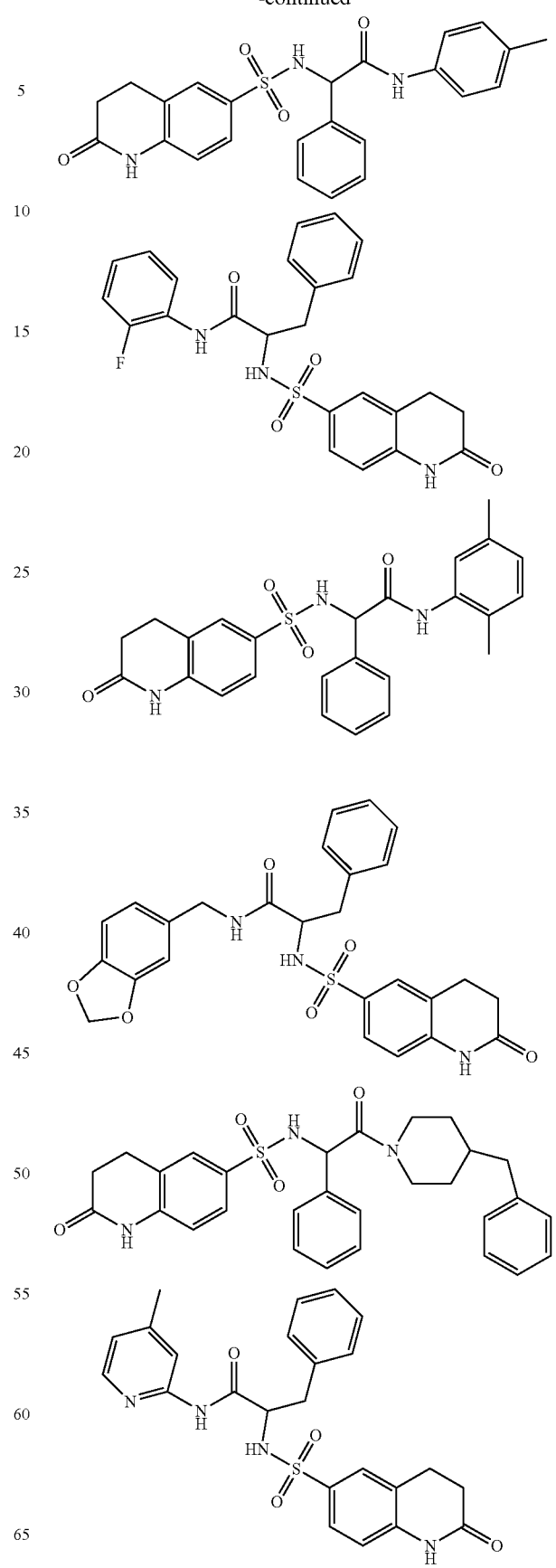

25
-continued
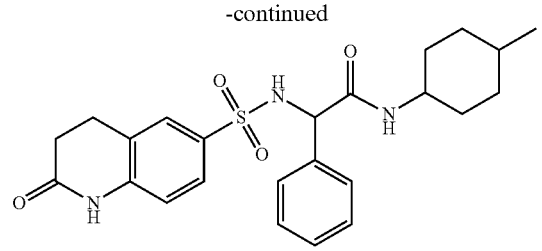
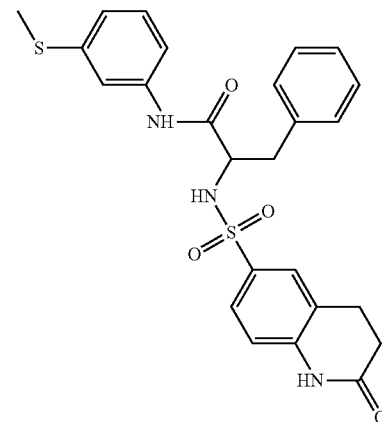
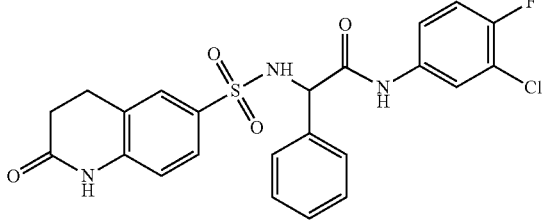
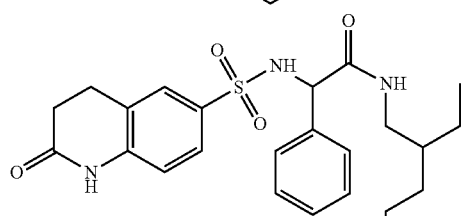
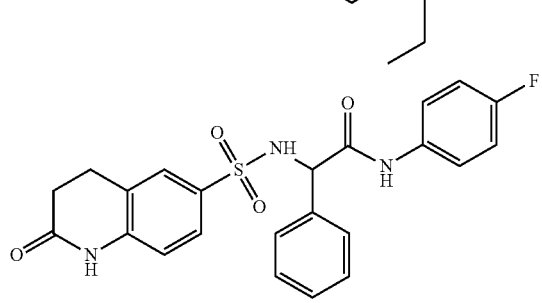
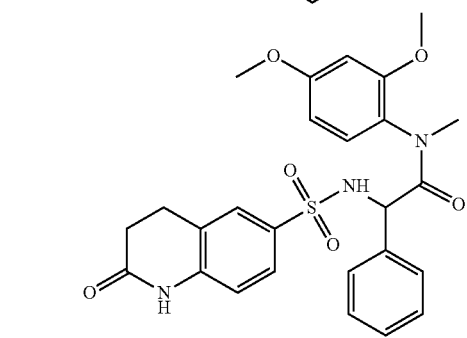
26
-continued
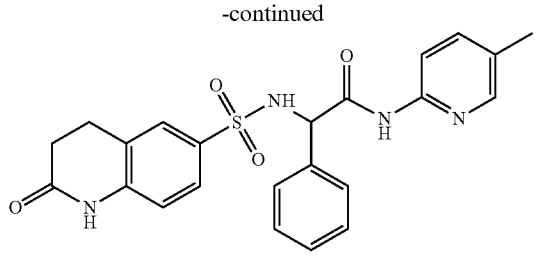
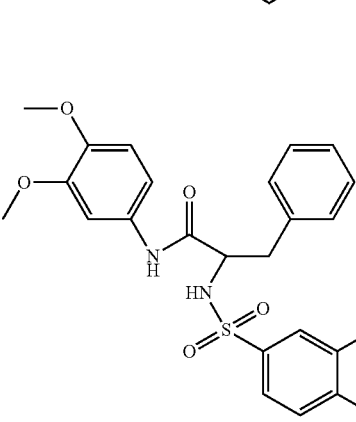
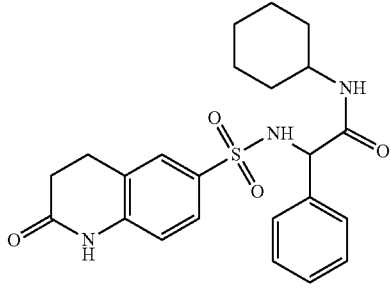
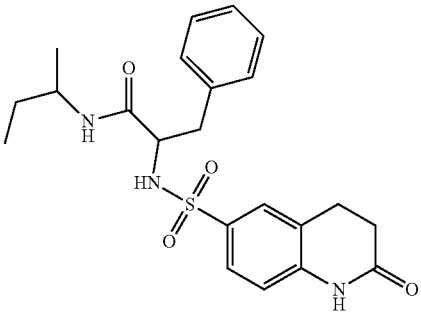
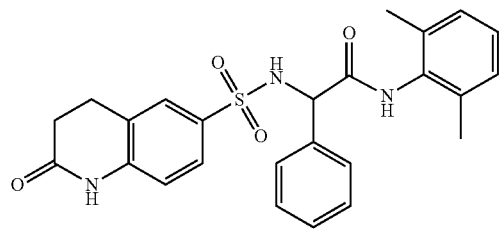

27
-continued
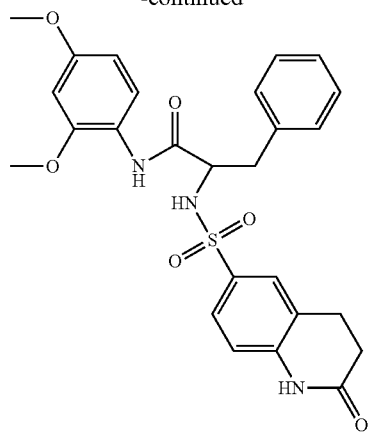
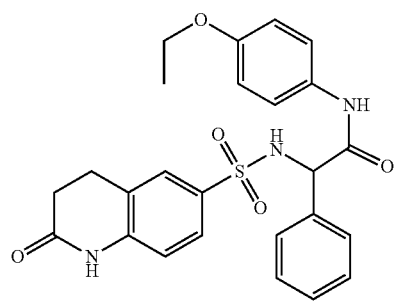
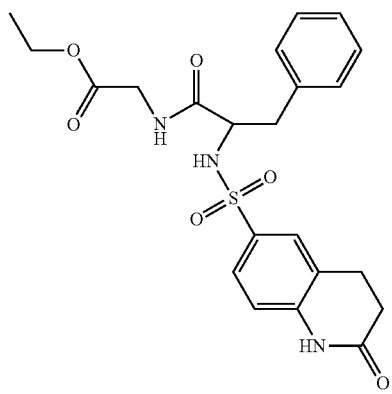
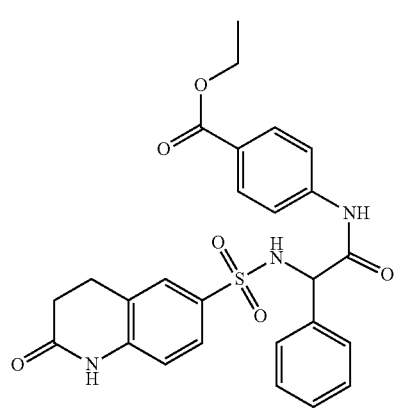
28
-continued
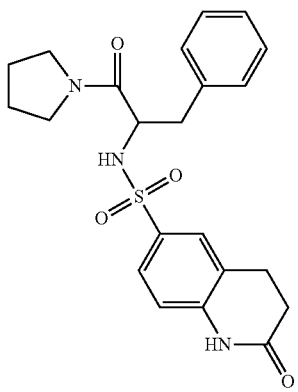
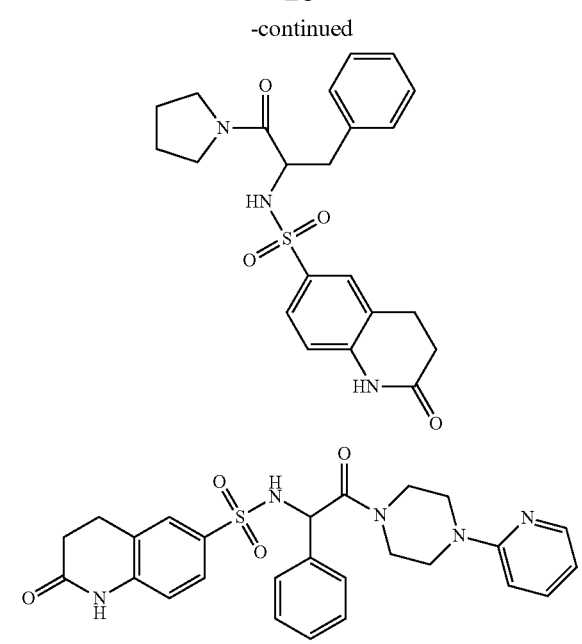
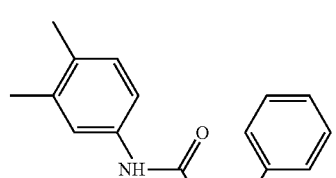
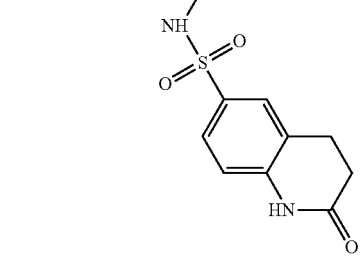
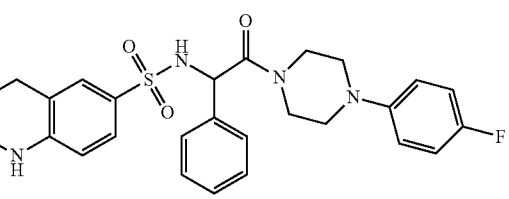
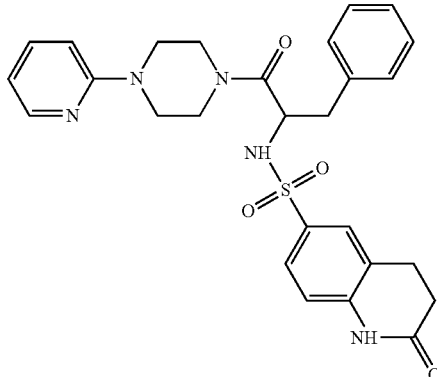

29
-continued
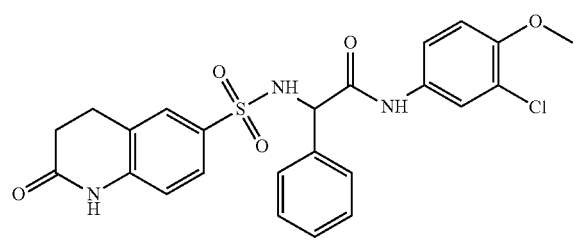
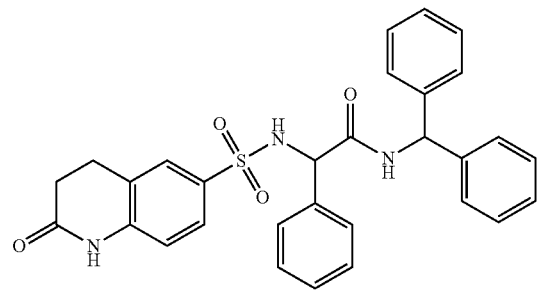
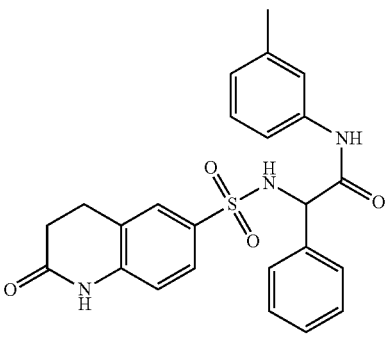
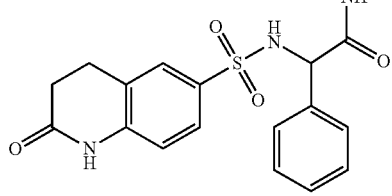
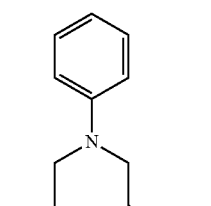
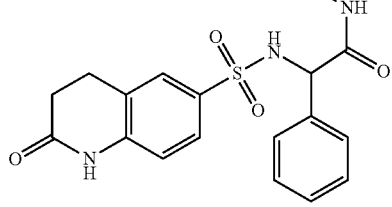
30
-continued
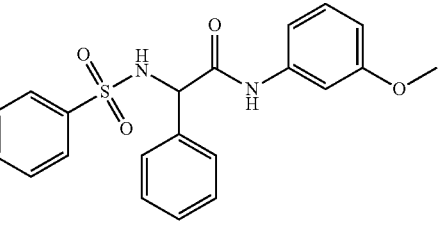
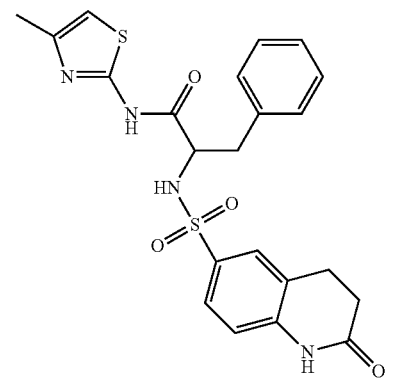
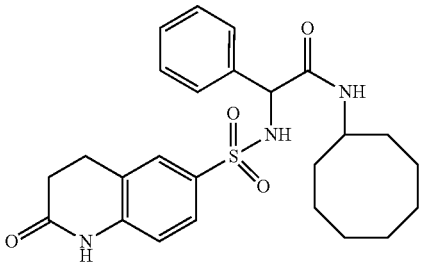
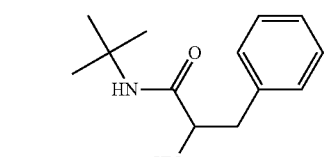
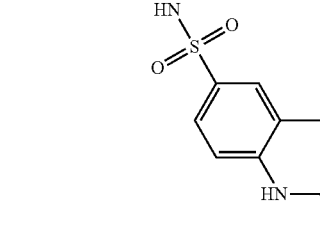
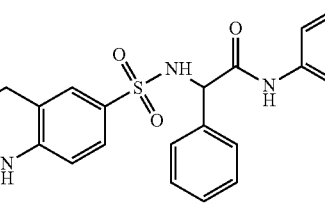

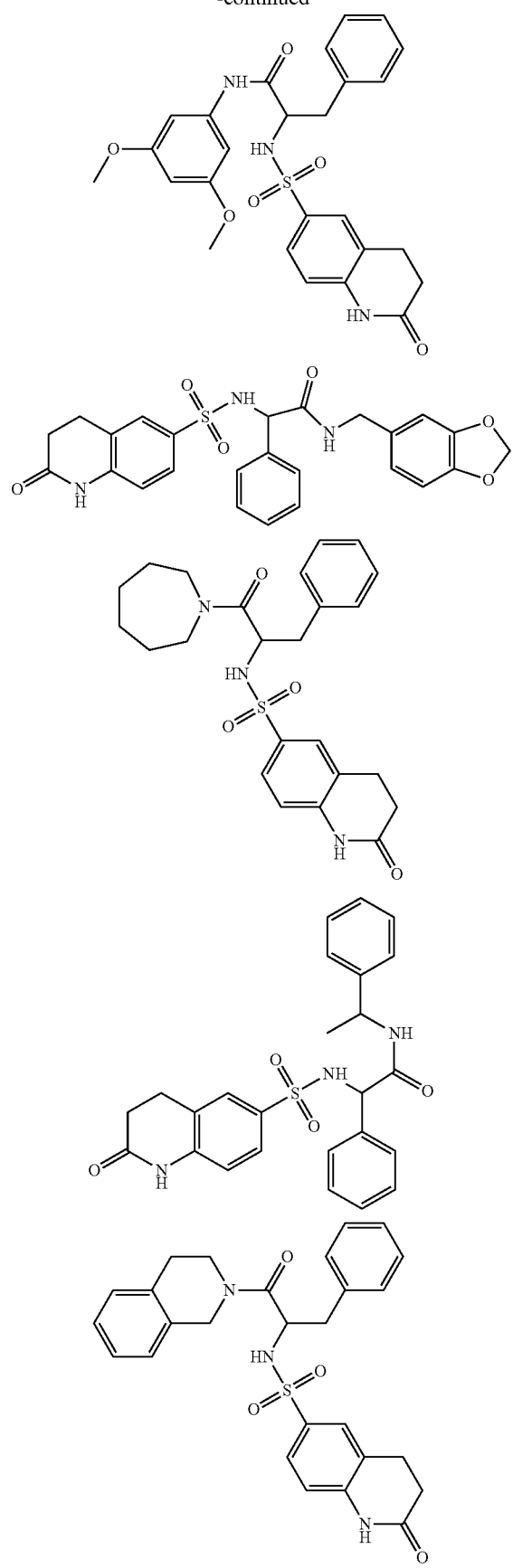
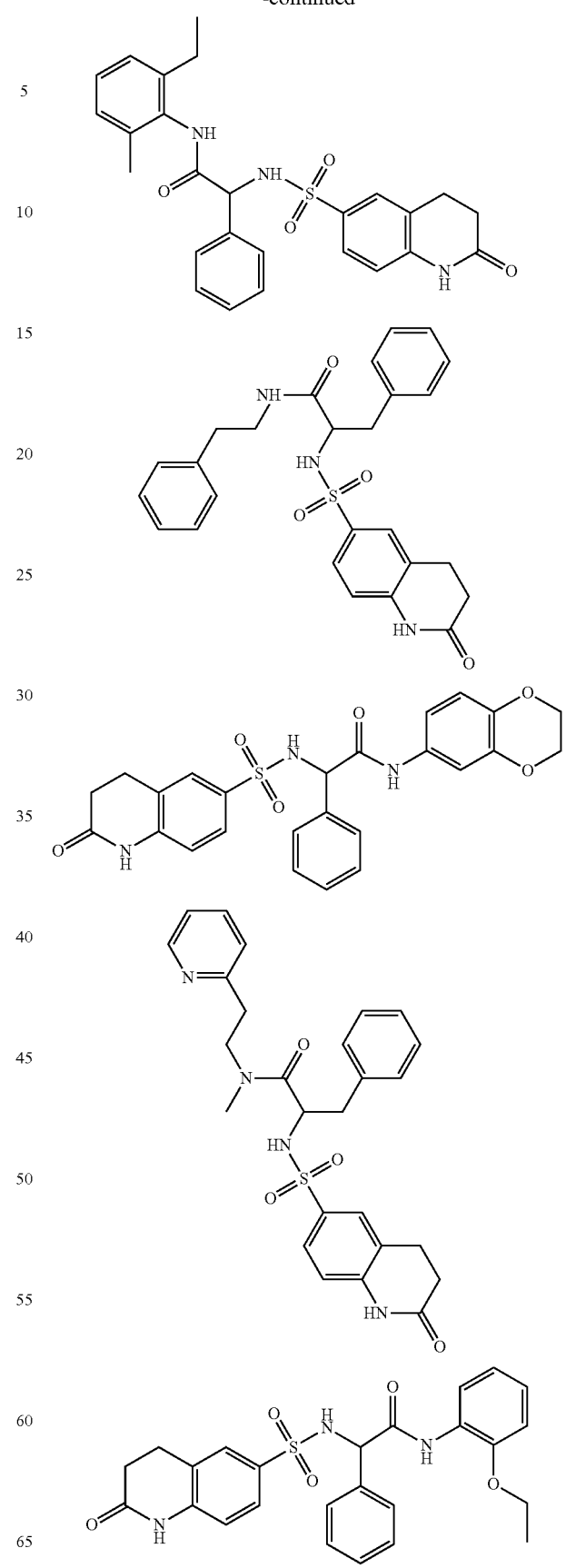

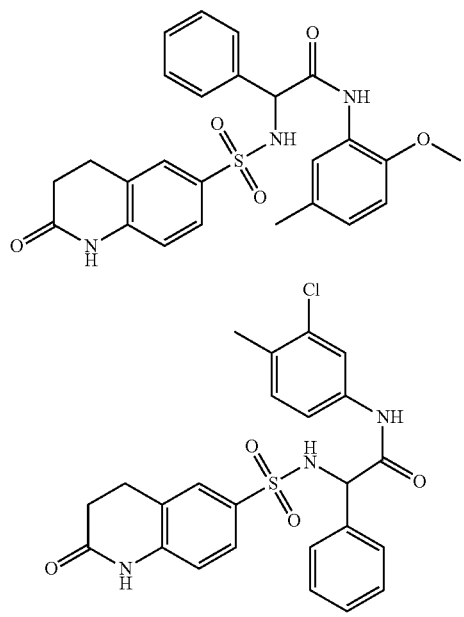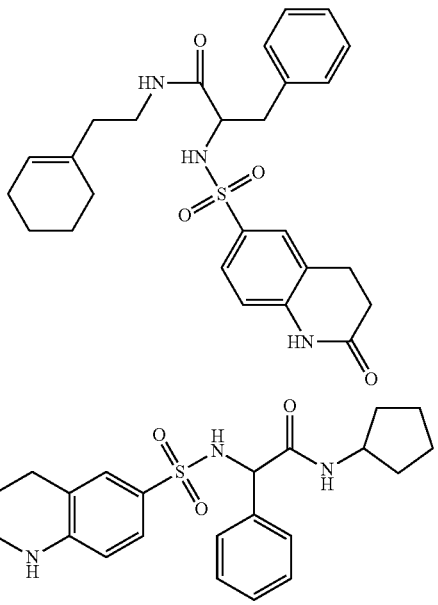

-continued
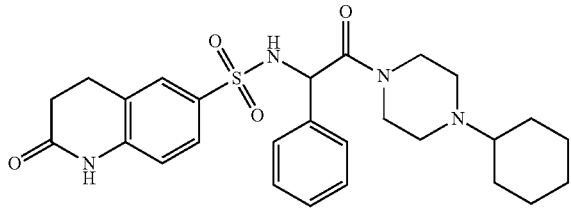
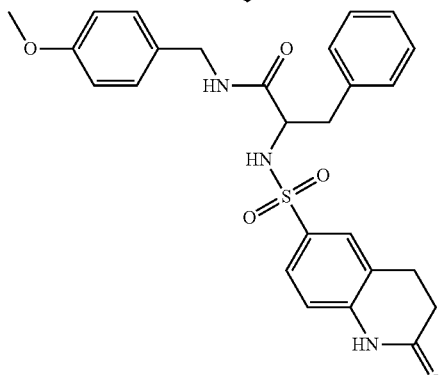
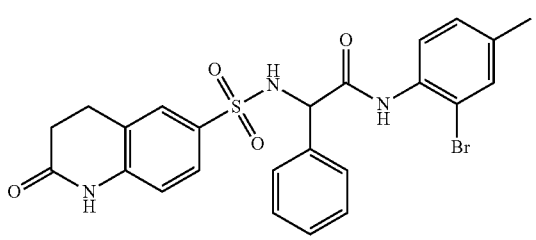
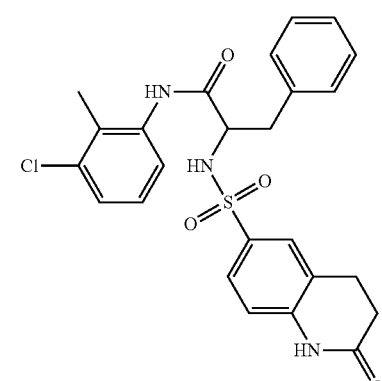
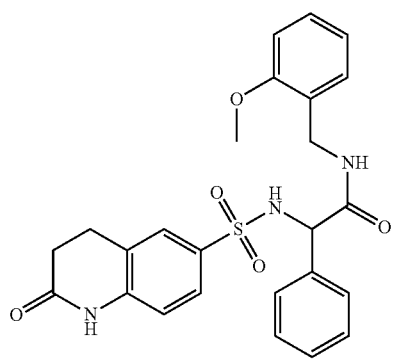
-continued
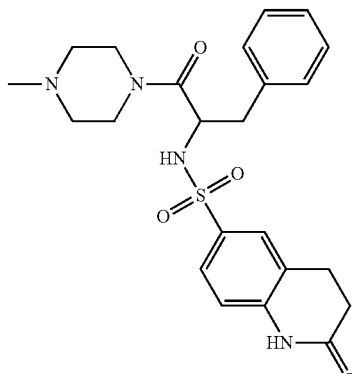
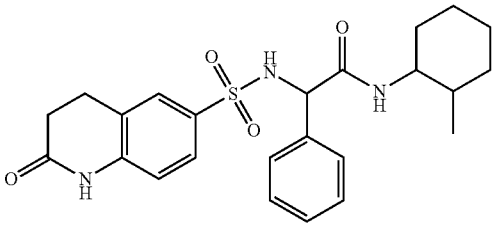
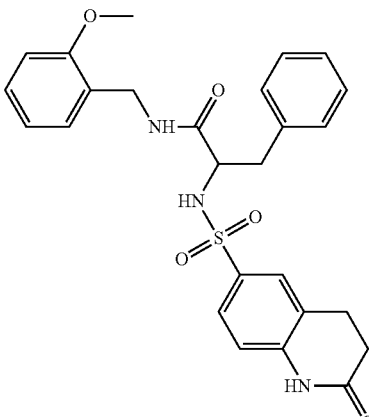
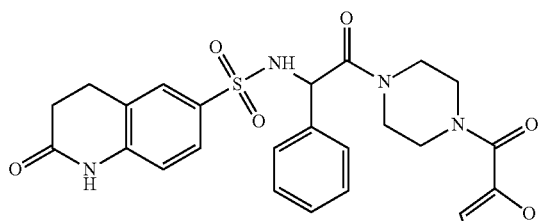
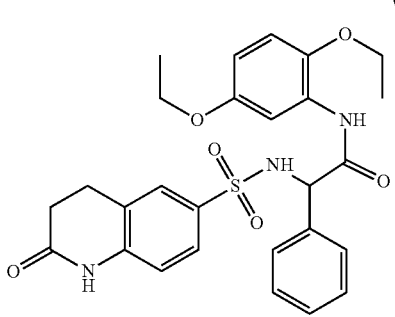

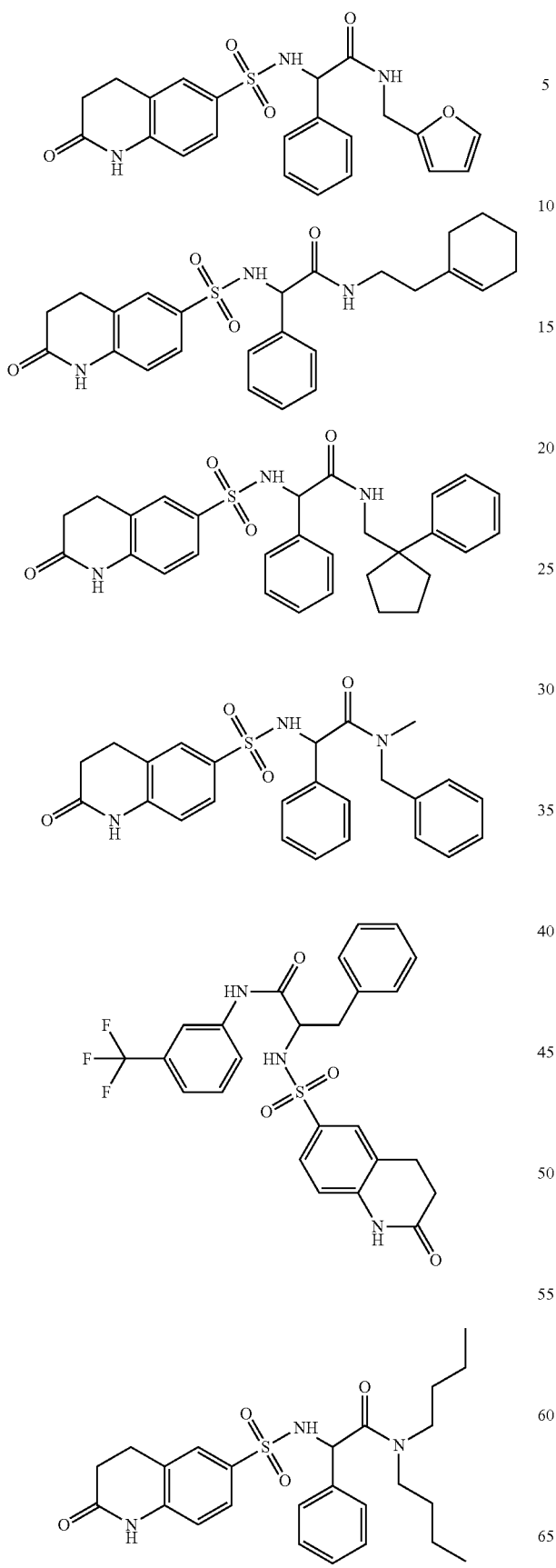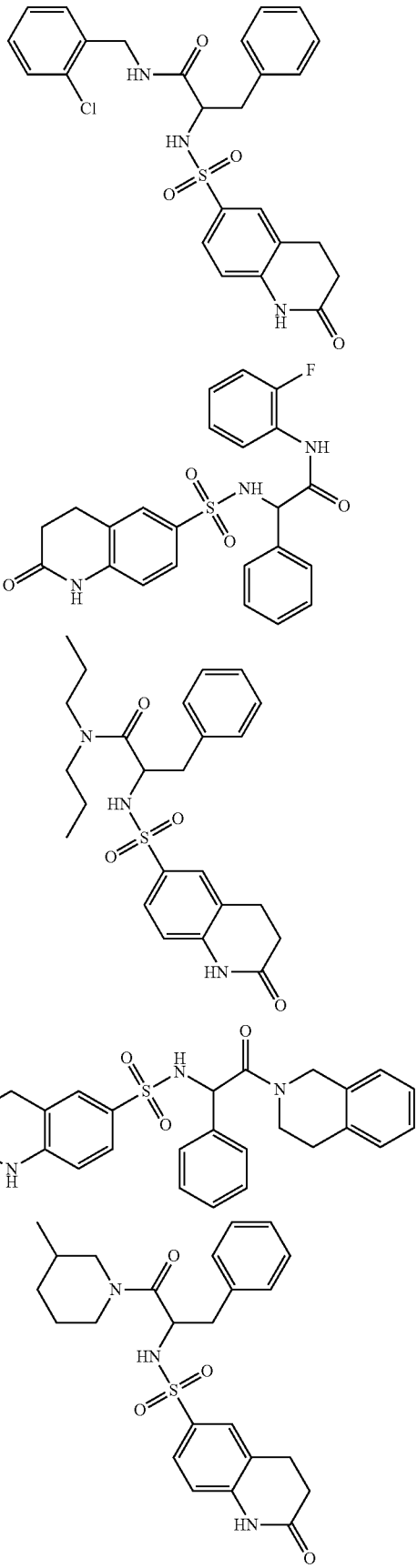

-continued
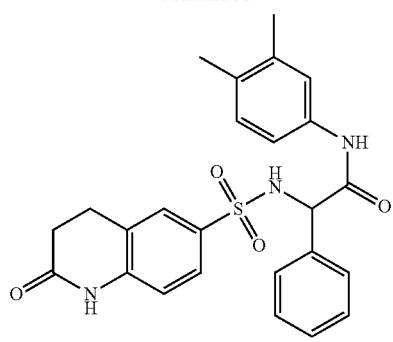
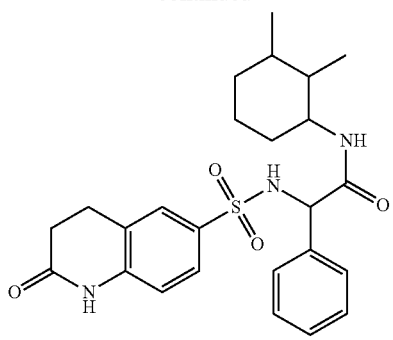
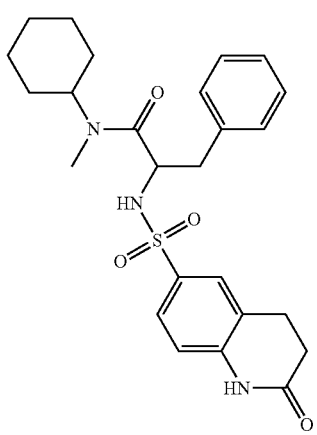
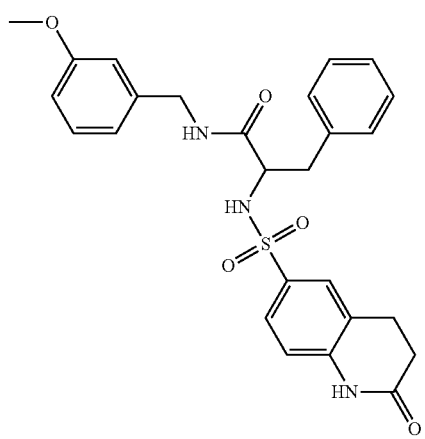
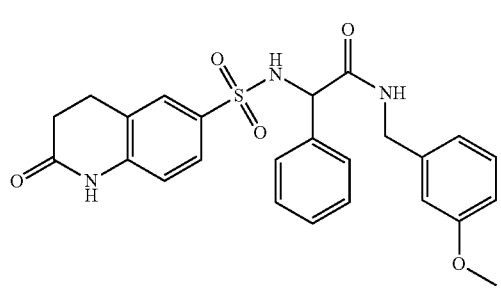
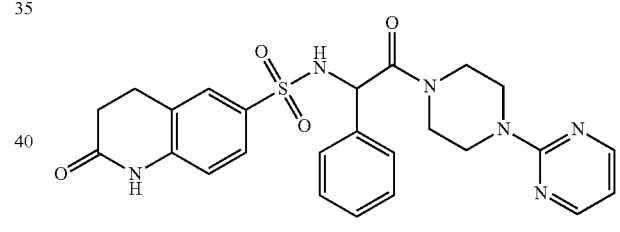
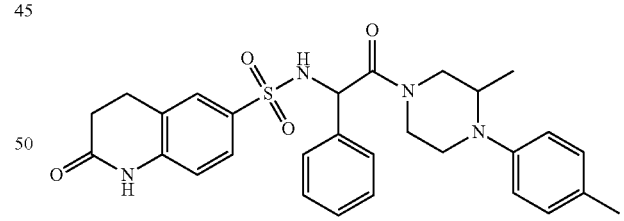
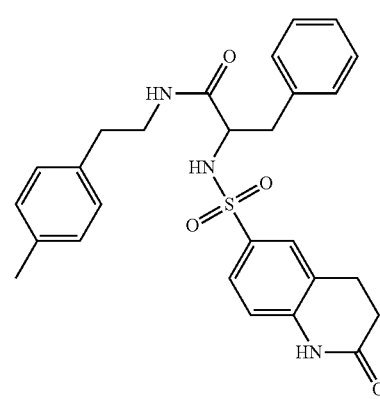
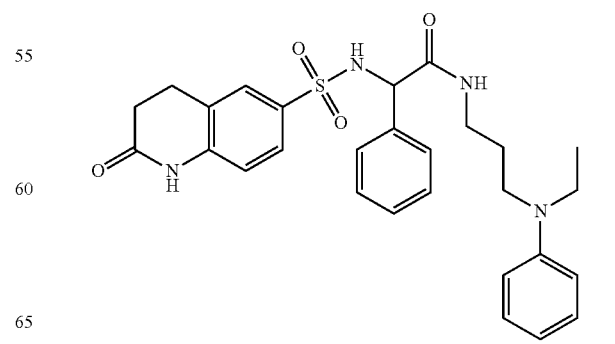

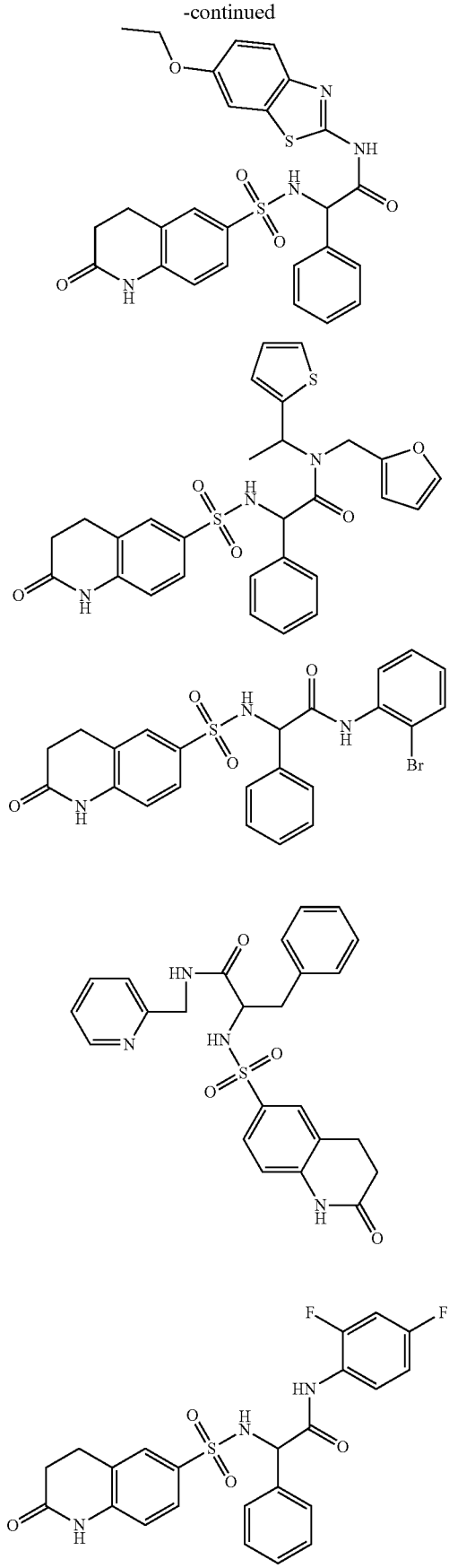
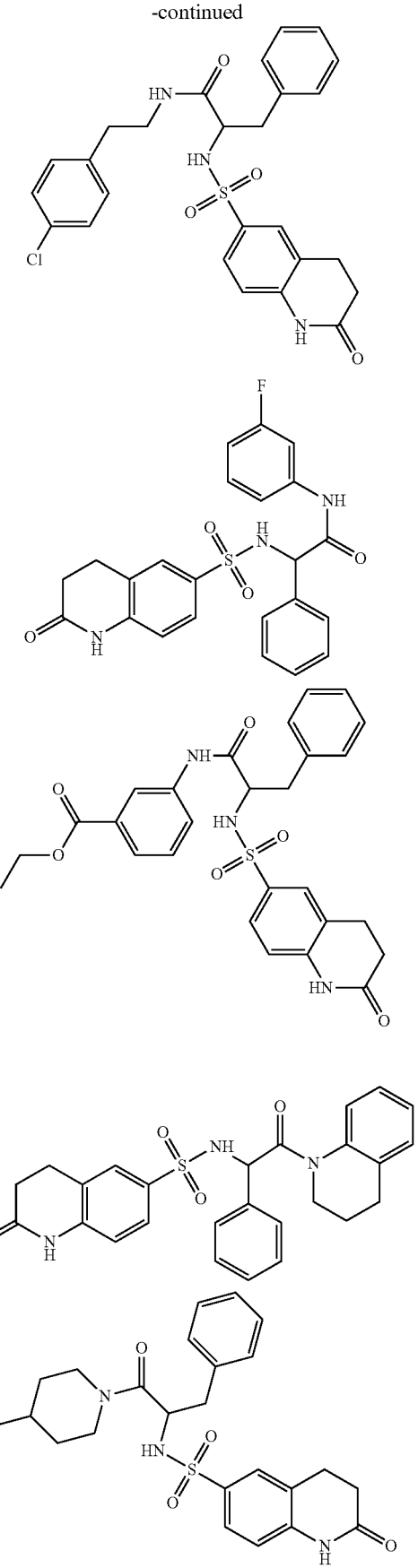

43
-continued
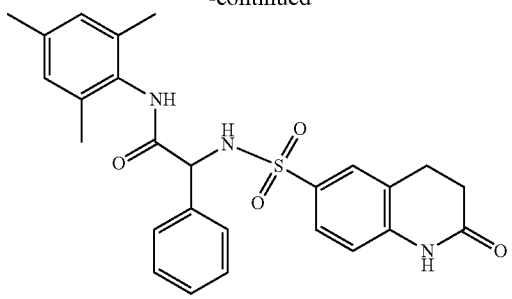
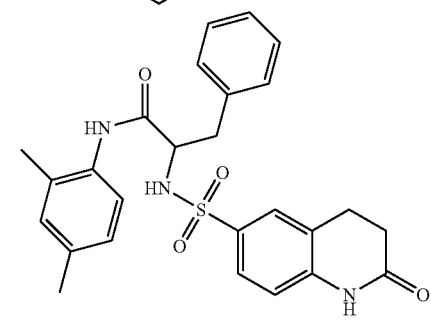
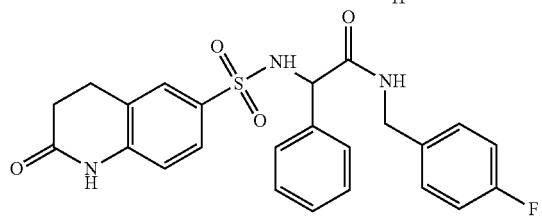
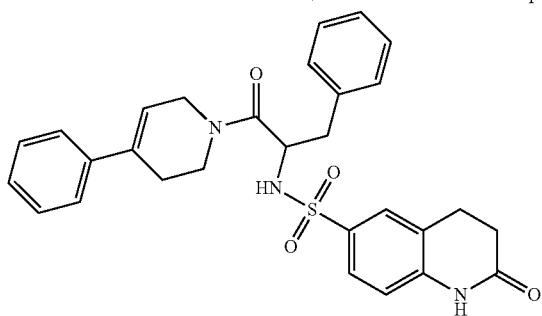
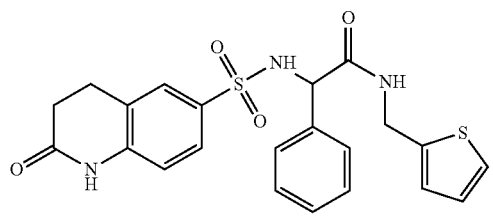
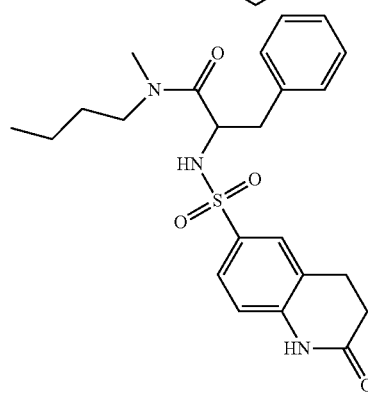
44
-continued
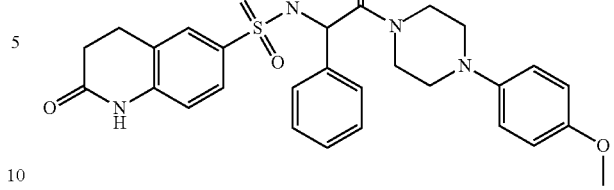
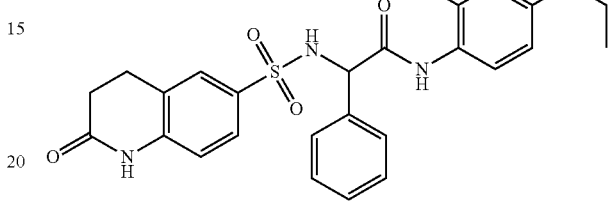
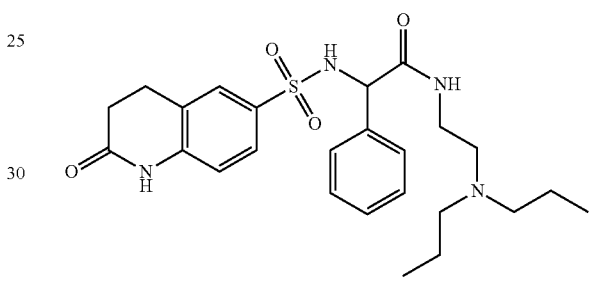
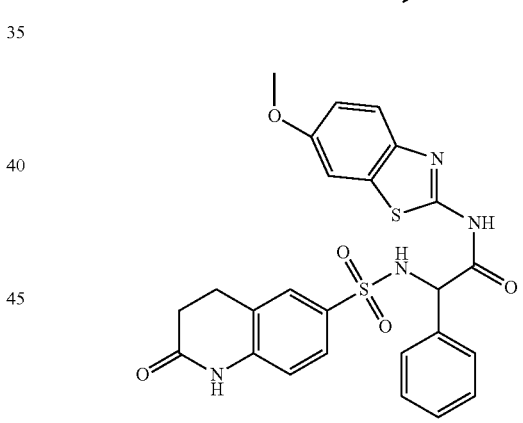
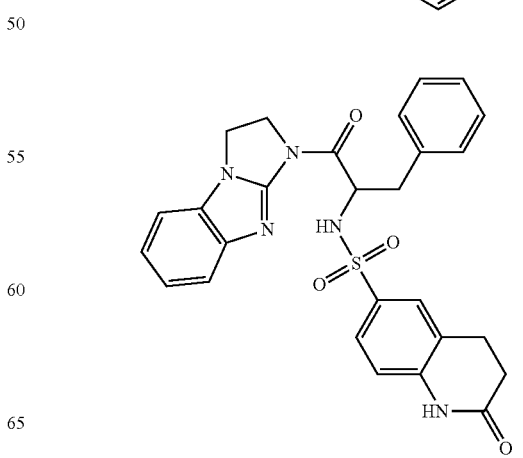

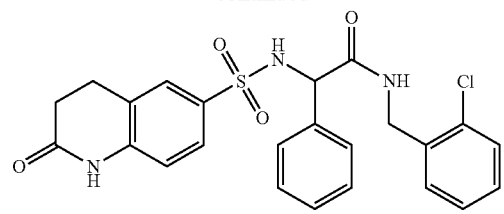
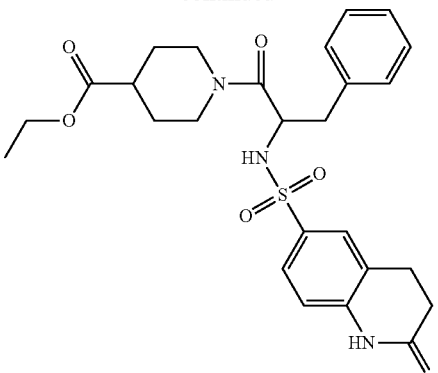
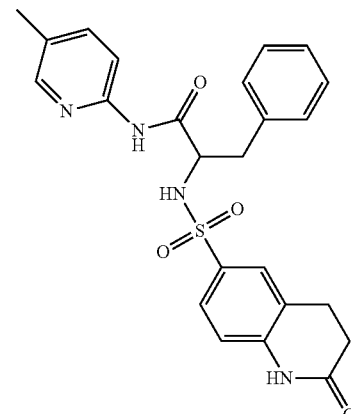
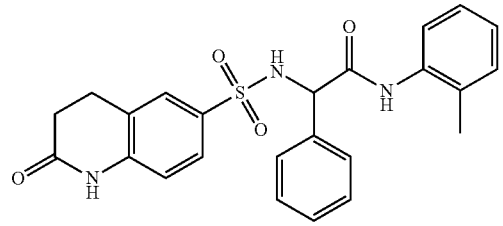
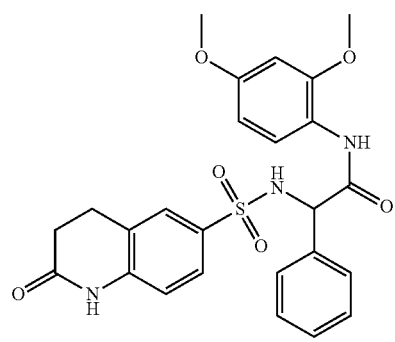
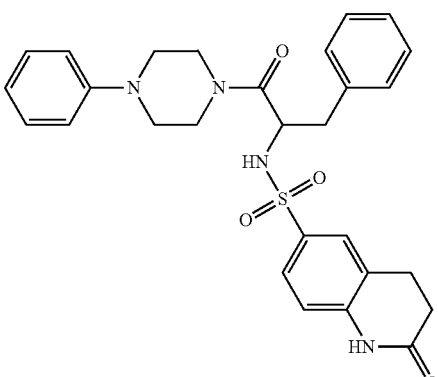
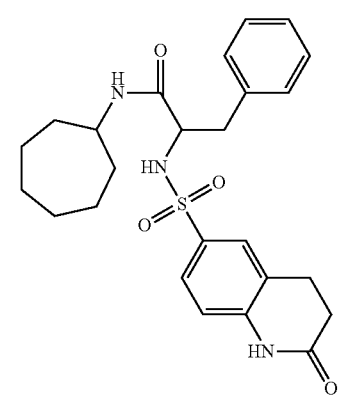
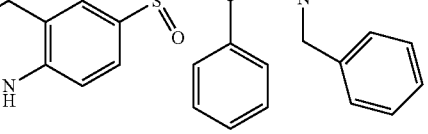
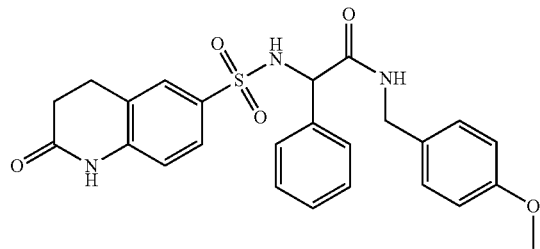
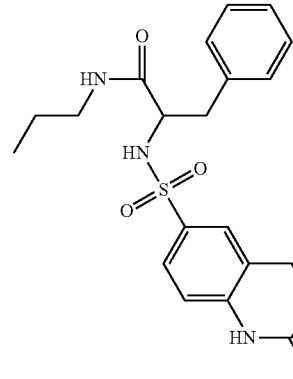

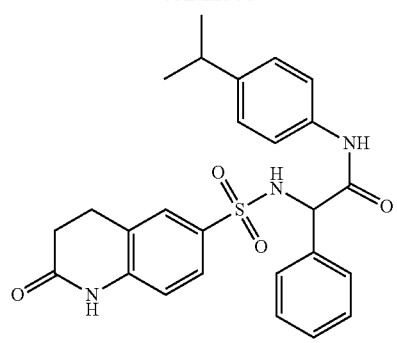
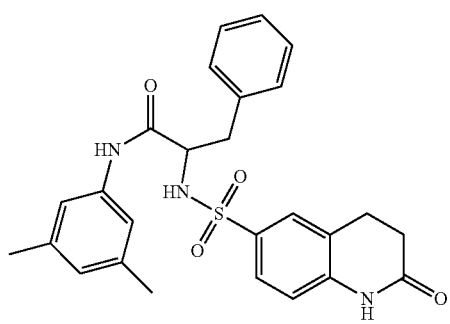
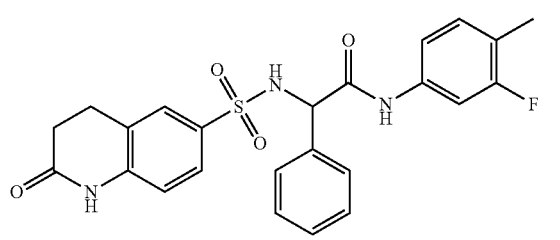
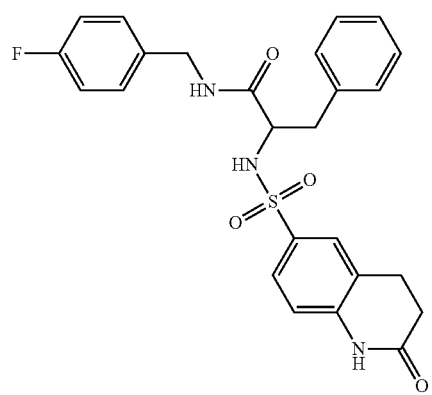
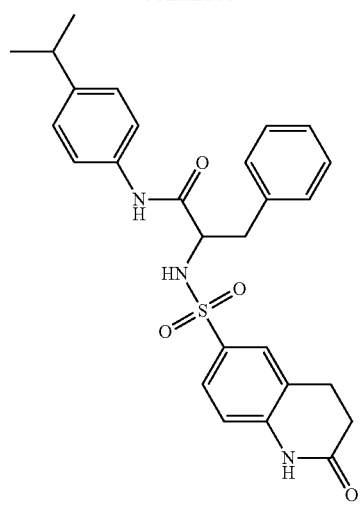
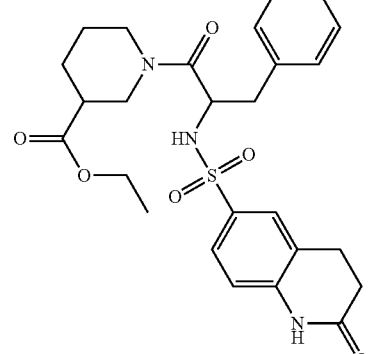
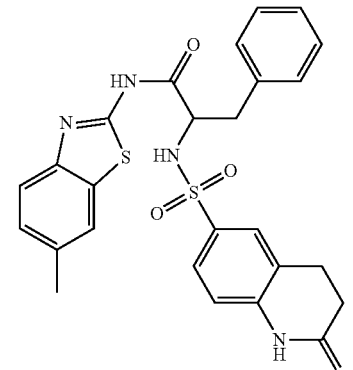
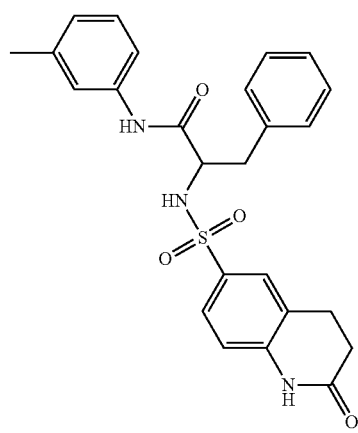

49
-continued
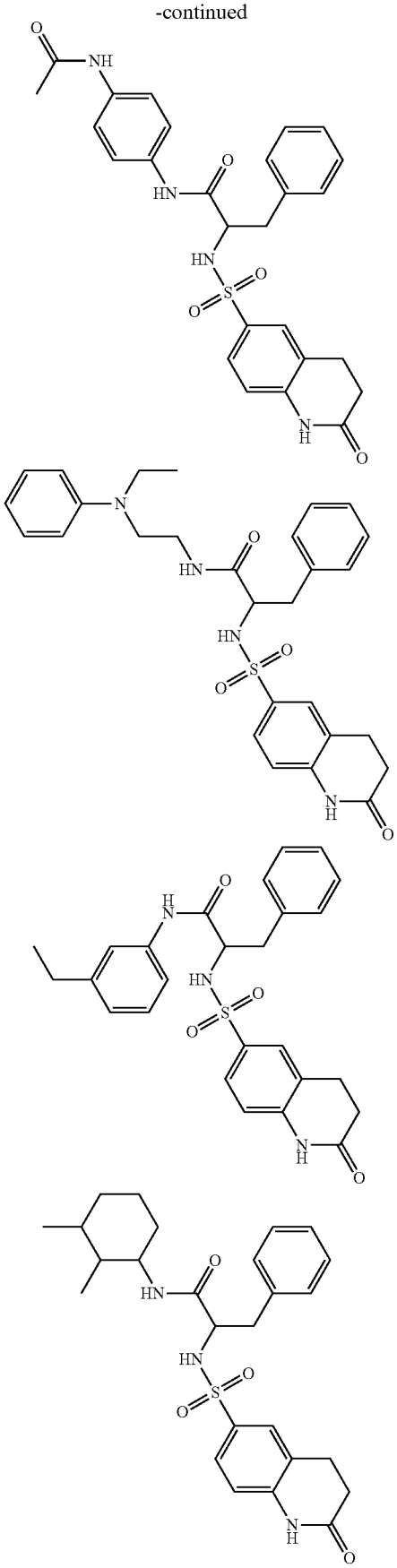
50
-continued
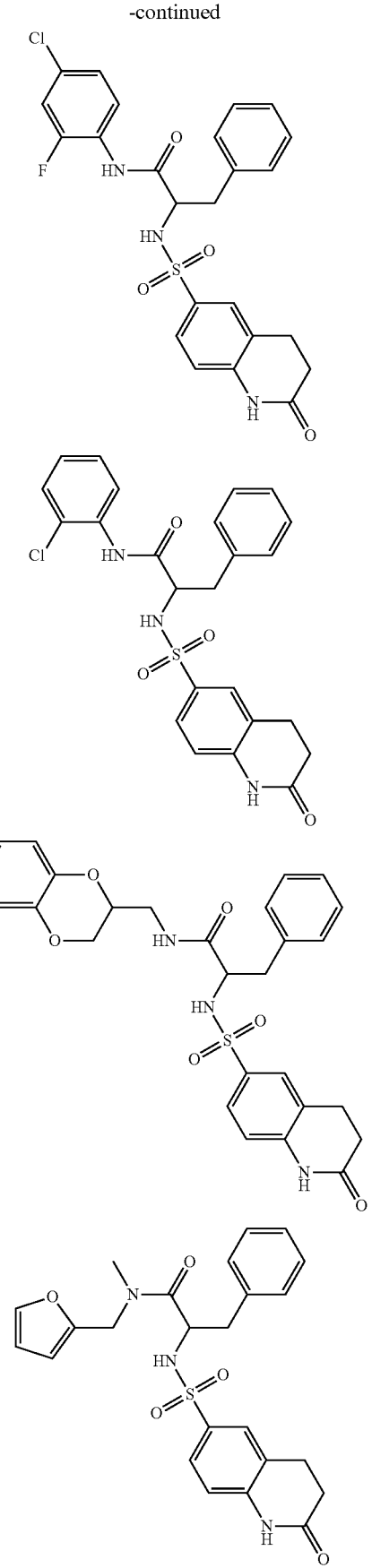

-continued
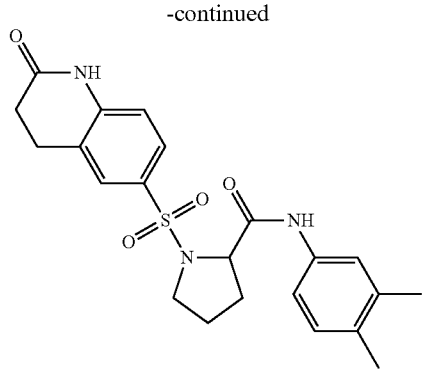
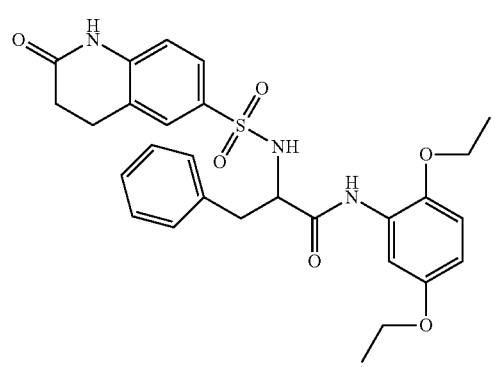
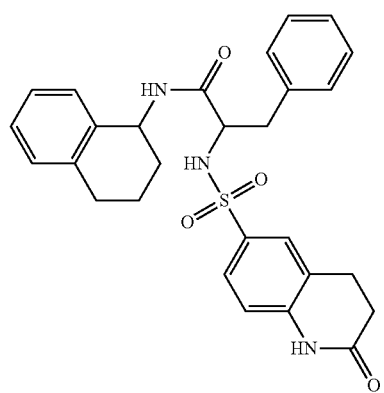
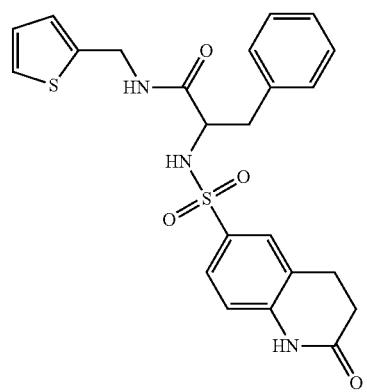
-continued
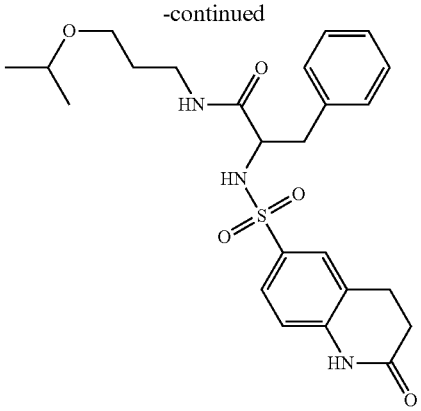
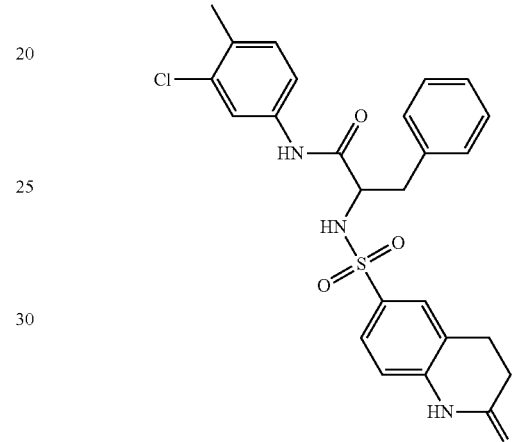
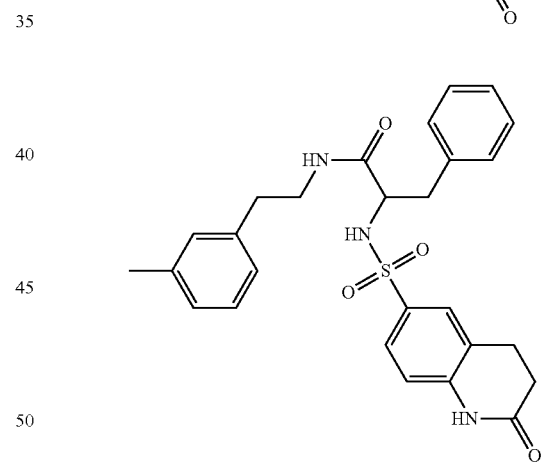
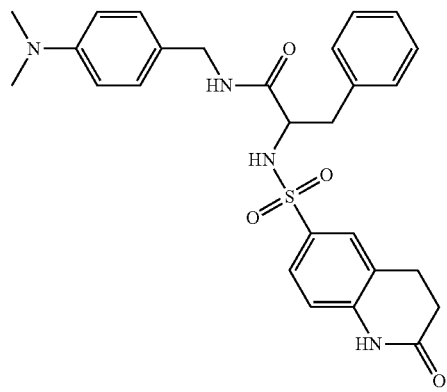

53
-continued
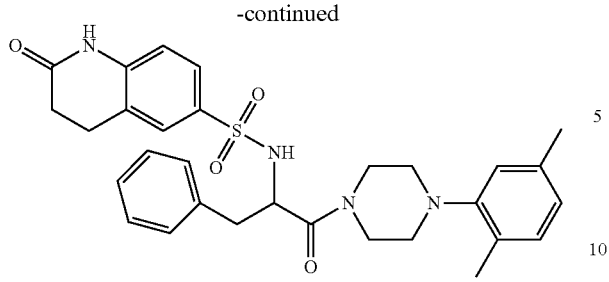
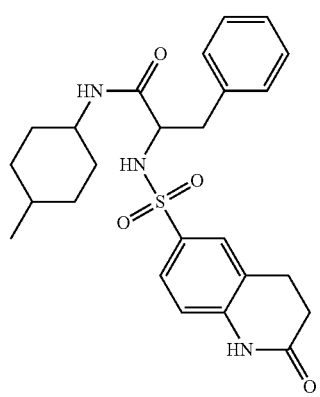
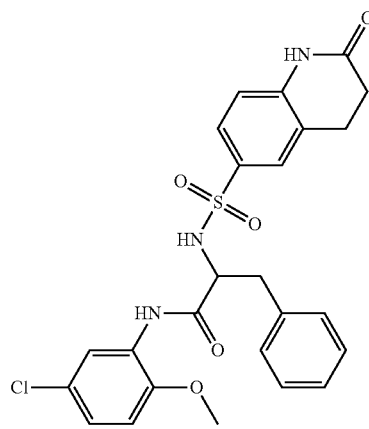
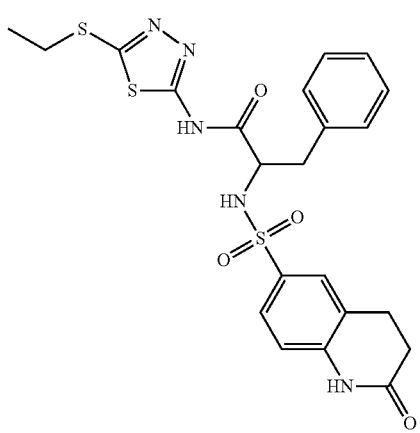
54
-continued
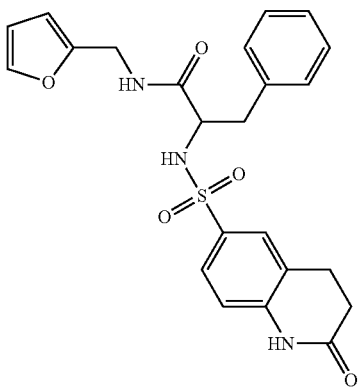
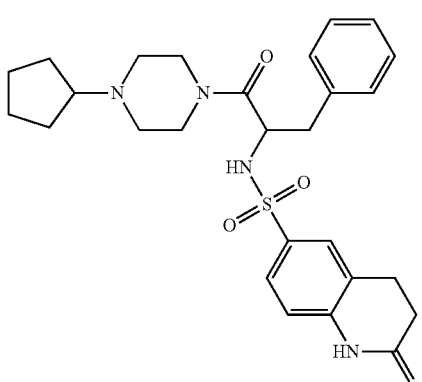
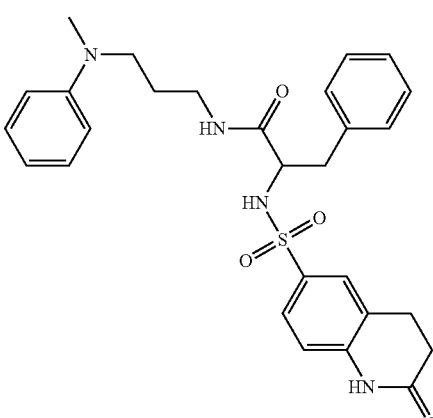
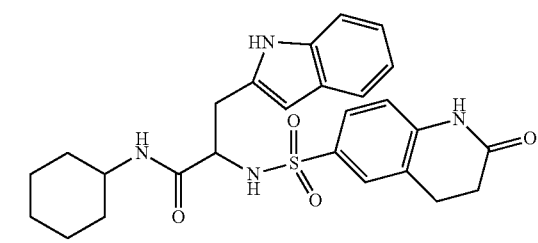

55
-continued
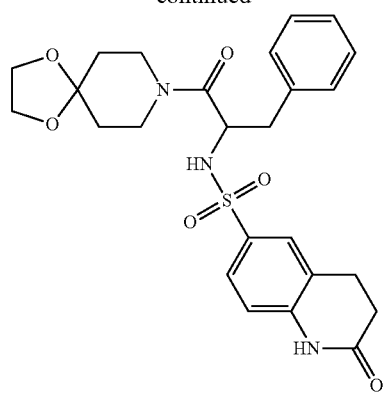
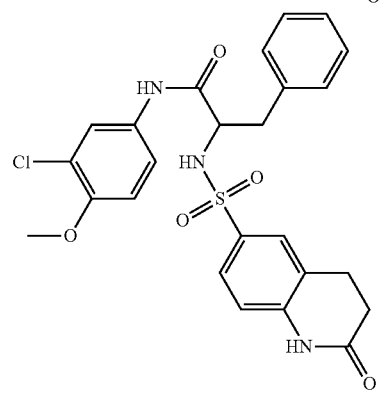
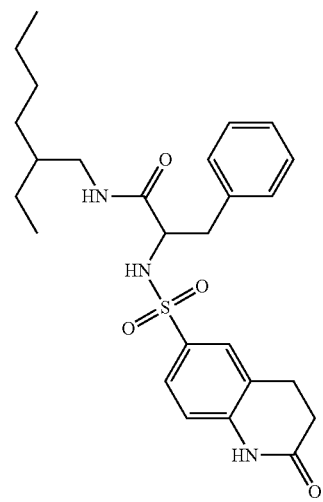
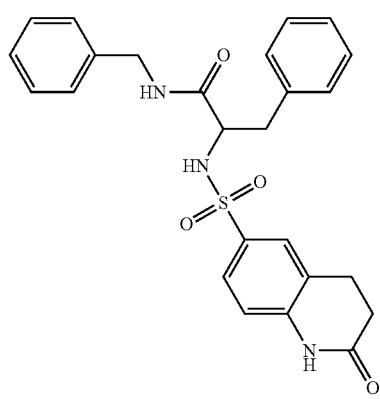
56
-continued
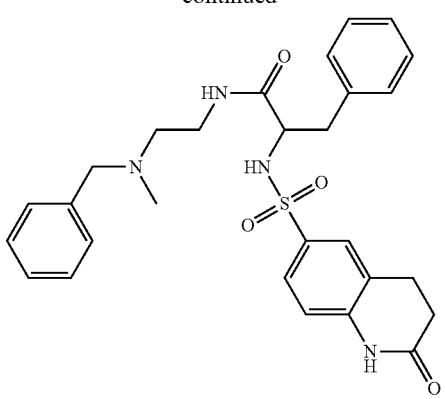
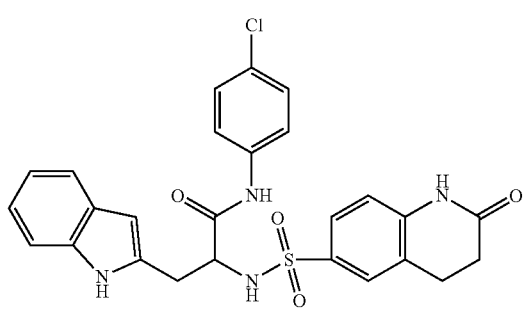
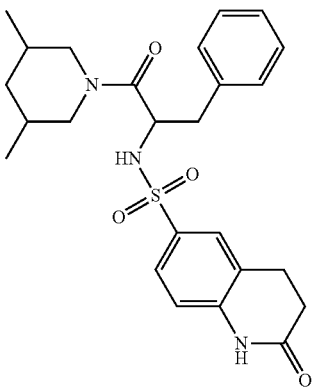
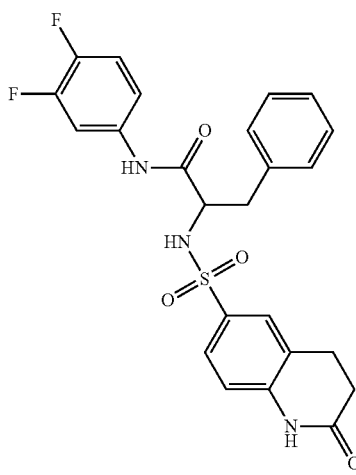

57
-continued
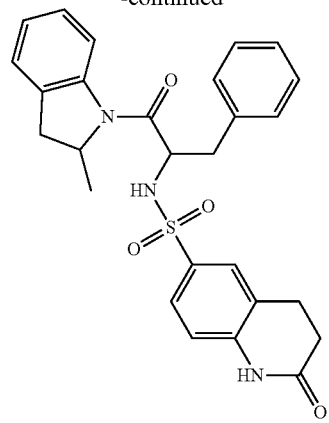
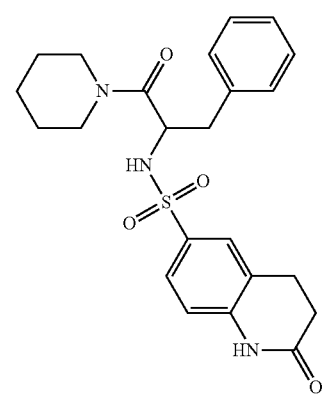
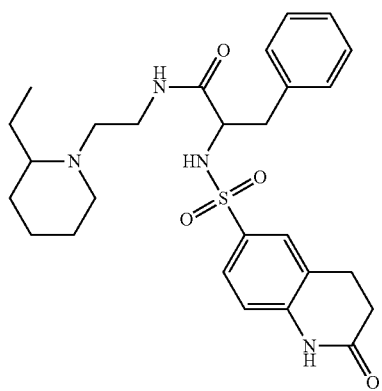
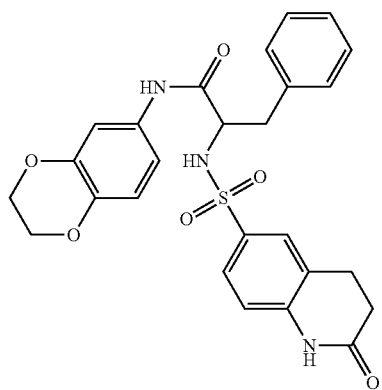
58
-continued
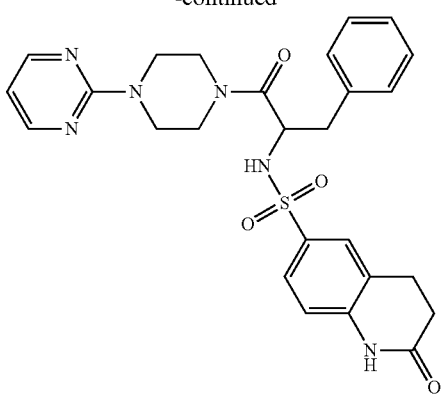
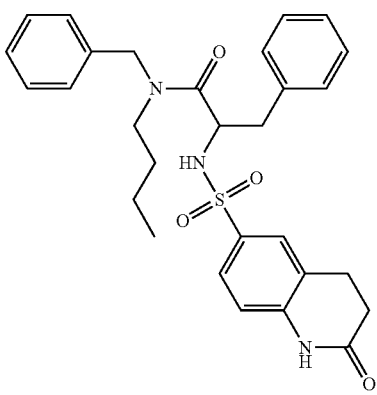
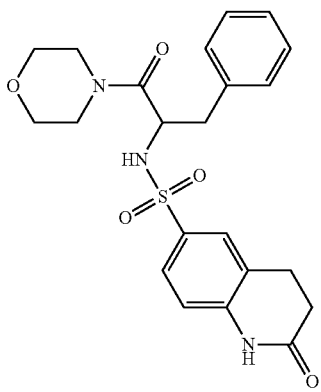
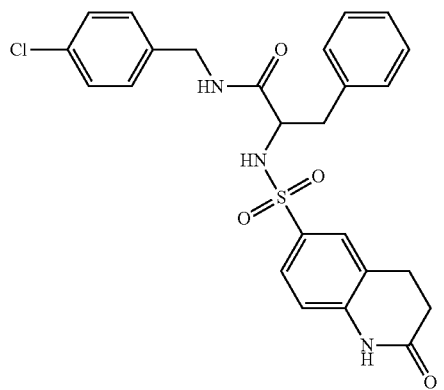

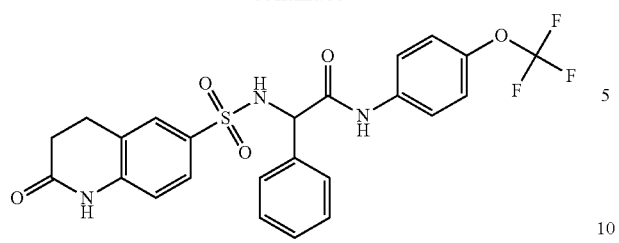
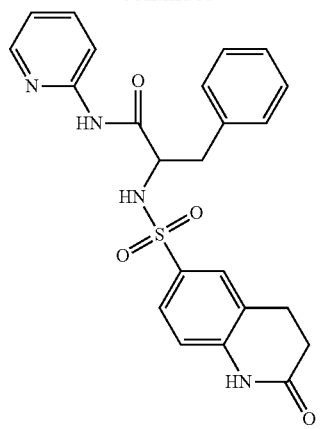
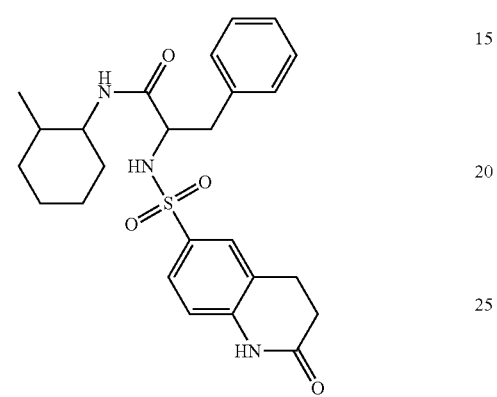
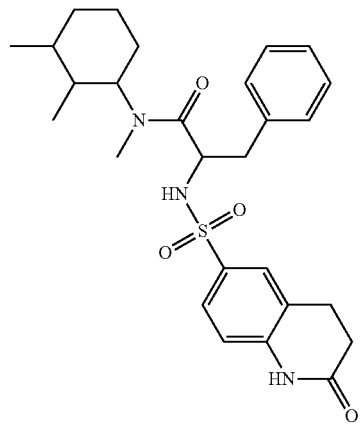
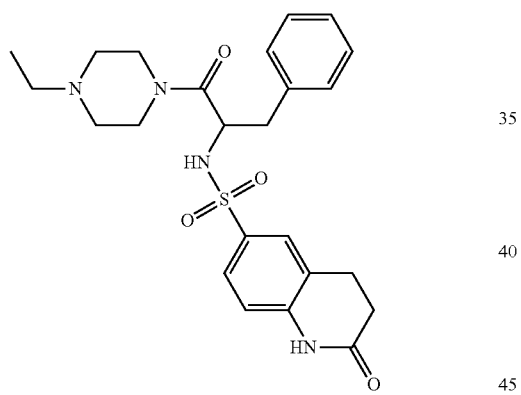
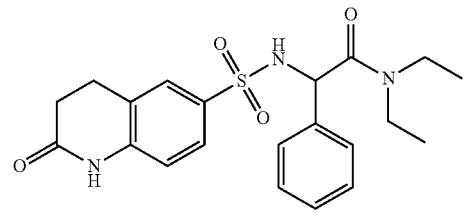
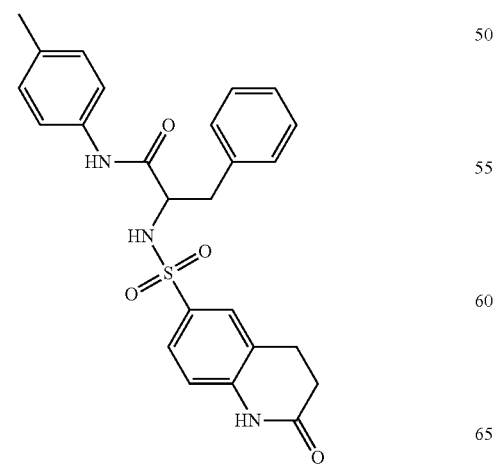
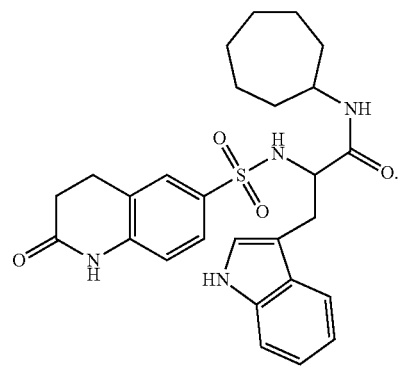

In certain embodiments, the compound of formula I is of formula Ia or Ib:

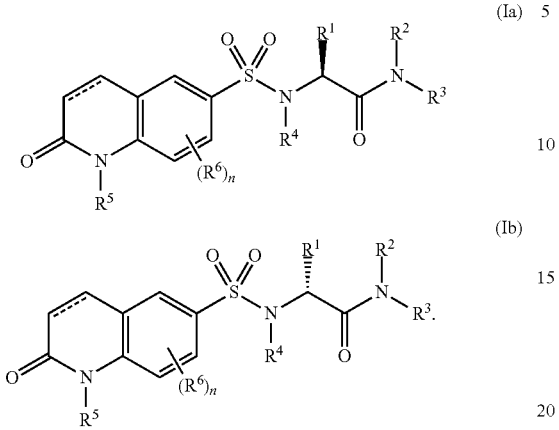

In certain embodiments, ---- is a double bond. In certain embodiments, ---- is a single bond. In other embodiments, ---- is a single bond, and $R^1$ is not phenyl or benzyl.

In some embodiments, $R^1$ is aliphatic. In other embodiments, $R^1$ is heteroaliphatic. In certain embodiments, $R^1$ is aryl. In certain other embodiments, $R^1$ is heteroaryl. In some embodiments, $R^1$ is arylalkyl or heteroarylalkyl. In certain embodiments, $R^1$ is phenyl. In yet other embodiments, $R^1$ is benzyl. In some embodiments, $R^1$ is of the (R) stereochemistry. In other embodiments, $R^1$ is of the (S) stereochemistry. In some embodiments, $R^1$ is an amino acid side chain. In certain embodiments, $R^1$ is isopropyl. In certain other embodiments, $R^1$ is isobutyl. In some embodiments, $R^1$ is sec-butyl. In some embodiments, $R^1$ is methyl. In other embodiments, $R^1$ is cyclohexyl. In certain embodiments, $R^1$ is thienyl. In certain other embodiments, $R^1$ is pyridyl, pyrimidyl, or pyridazyl. In yet other embodiments, $R^1$ is furanyl, pyrrolyl, imidazolyl, oxazolyl, thiazolyl, pyrazolyl, triazolyl, or isoxazolyl.

In some embodiments, $R^2$ is hydrogen. In some embodiments, $R^2$ is aliphatic. In other embodiments, $R^2$ is heteroaliphatic. In certain embodiments, $R^2$ is aryl. In certain other embodiments, $R^2$ is heteroaryl. In some embodiments, $R^2$ is arylalkyl. In certain embodiments, $R^2$ is heteroarylalkyl. In other embodiments, $R^2$ is substituted phenyl. In some embodiments, $R^2$ is pyridyl, pyrimidyl, or pyridazyl. In certain embodiments, $R^2$ is thienyl, furanyl, pyrrolyl, imidazolyl, oxazolyl, thiazolyl, pyrazolyl, triazolyl, or isoxazolyl. In yet other embodiments, $R^2$ is benzyl. In certain embodiments, $R^2$ is isopropyl. In other embodiments, $R^2$ is methyl. In some embodiments, $R^2$ is ethyl. In certain embodiments, $R^2$ is one of the following moieties:

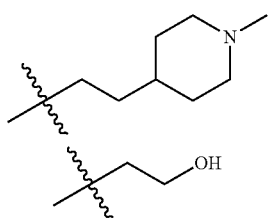

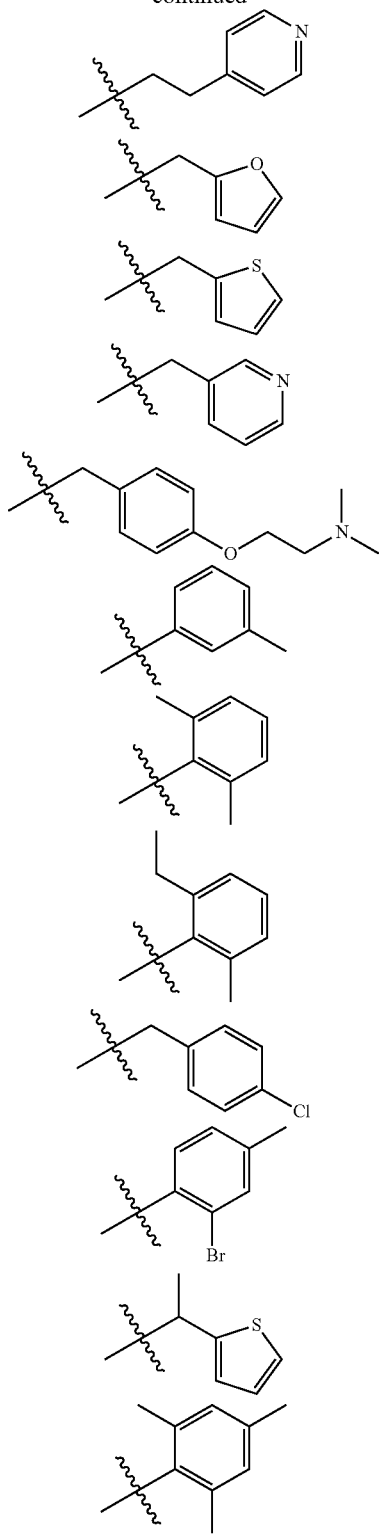

In some embodiments, $R^3$ is hydrogen. In some embodiments, $R^3$ is aliphatic. In other embodiments, $R^3$ is heteroaliphatic. In certain embodiments, $R^3$ is aryl. In certain other embodiments, $R^3$ is heteroaryl. In some embodiments, $R^3$ is arylalkyl. In certain embodiments, $R^3$ is heteroarylalkyl. In other embodiments, $R^3$ is substituted phenyl. In some embodiments, $R^3$ is pyridyl, pyrimidyl, or pyridazyl. In certain embodiments, R³ is thienyl, furanyl, pyrrolyl, imidazolyl, oxazolyl, thiazolyl, pyrazolyl, triazolyl, or isoxazolyl. In yet other embodiments, R³ is benzyl. In certain embodiments, R³ is isopropyl. In other embodiments, R³ is methyl. In some embodiments, R³ is ethyl. In certain embodiments, R³ is one of the following moieties:

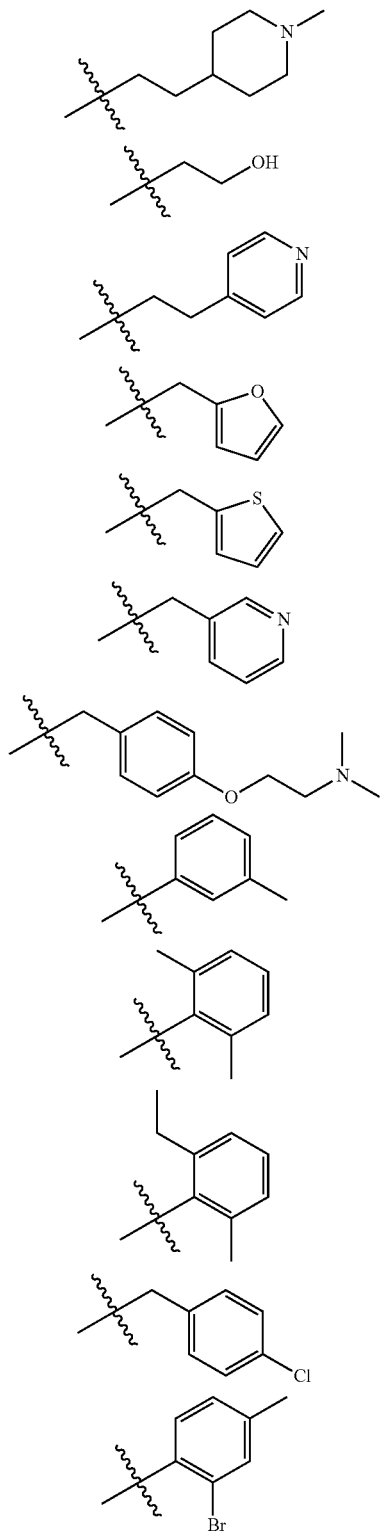

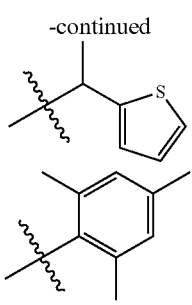

In some embodiments, one of R² and R³ is hydrogen. In some embodiments, neither of R² and R³ is hydrogen. In some embodiments, R² and R³ are both hydrogen. In other embodiments, each of R² and R³ is independently selected from $C_{1-6}$ alkyl, $C_{1-6}$ heteroalkyl, aryl, heteroaryl, arylalkyl, or heteroarylalkyl. In certain embodiments, at least one of R² and R³ is arylalkyl or heteroarylalkyl. In certain other embodiments, both of R² and R³ are arylalkyl or heteroarylalkyl. In yet other embodiments, both of R² and R³ are heteroarylalkyl.

In some embodiments, R² and R³ are taken together with the intervening nitrogen to form a heterocyclic moiety. In some embodiments, the ring formed by R² and R³ is saturated. In other embodiments, the ring formed by R² and R³ is unsaturated. In some embodiments, R² and R³ are taken together to form a 6-membered heterocyclic ring. In other embodiments, R² and R³ are taken together to form a substituted or unsubstituted pyrrolidine, piperidine, or homopiperidine ring. In certain embodiments, the ring formed by R² and R³ is a piperidine ring. In certain other embodiments, the ring formed by R² and R³ is a piperazine ring. In some embodiments, the ring formed by R² and R³ is substituted. In certain embodiments, the ring formed by R² and R³ is linked or fused to another moiety to form a bicyclic ring system. In certain embodiments, R² and R³ are taken together to form one of the following heterocyclic moieties:

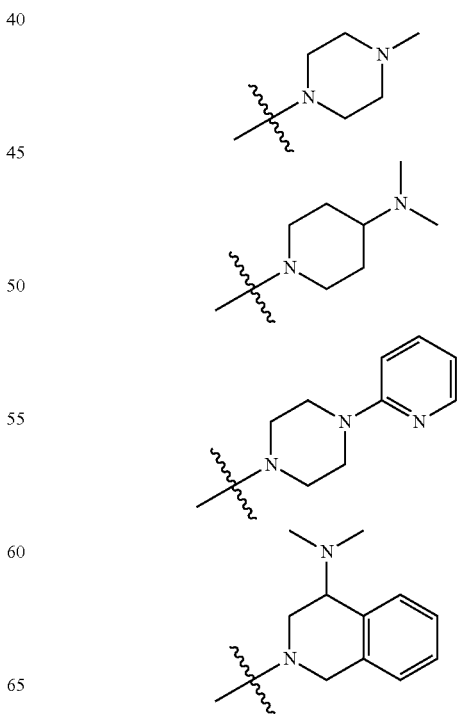

-continued

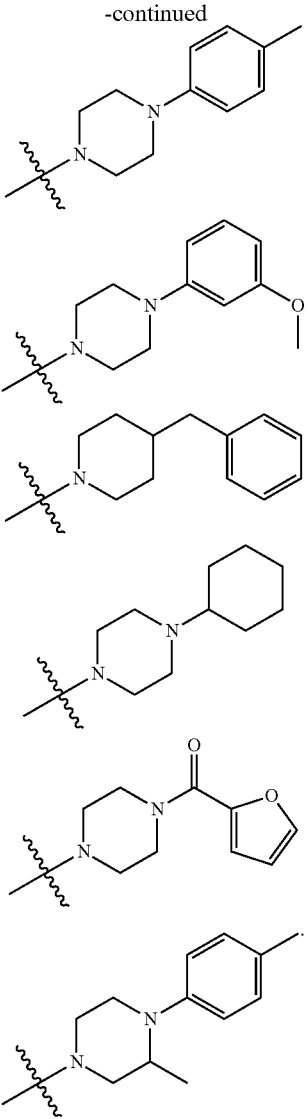

In certain embodiments, $R^4$ is hydrogen. In certain other embodiments, $R^4$ is $C_{1-6}$ aliphatic. In some embodiments, $R^4$ is $C_{1-6}$ alkyl. In some embodiments, $R^4$ is methyl. In other embodiments, $R^4$ is ethyl. In yet other embodiments, $R^4$ is propyl. In some embodiments, $R^4$ is a nitrogen protecting group.

In certain embodiments, $R^5$ is hydrogen. In certain other embodiments, $R^5$ is $C_{1-6}$ aliphatic. In some embodiments, $R^5$ is $C_{1-6}$ alkyl. In some embodiments, $R^5$ is methyl. In other embodiments, $R^5$ is ethyl. In yet other embodiments, $R^5$ is propyl. In some embodiments, $R^5$ is a nitrogen protecting group.

As defined generally above, $R^6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR^F$; —$C(=O)R^F$; —$CO_2R^F$; —$C(=O)N(R^F)_2$; —CN; —SCN; —$SR^F$; —$SOR^F$; —$SO_2R^F$; —$NO_2$; —$N(R^F)_2$; —NHC(O)$R^F$; or —$C(R^F)_3$; wherein each occurrence of $R^F$ is independently hydrogen; halogen; a protecting group; aliphatic; heteroaliphatic; acyl; aryl moiety; heteroaryl; alkoxy; aryloxy; alkylthioxy; arylthioxy; amino; alkylamino; dialkylamino; heteroaryloxy; or heteroarylthioxy. In certain embodiments, $R^6$ is hydrogen. In certain other embodiments, $R^6$ is halogen.

In certain embodiments, n is 0. In other embodiments, n is 1, 2, or 3.

In certain embodiments, $R^5$ and $R^6$ are hydrogen, and n is 0.

In certain embodiments, compounds of the invention are of the formula:

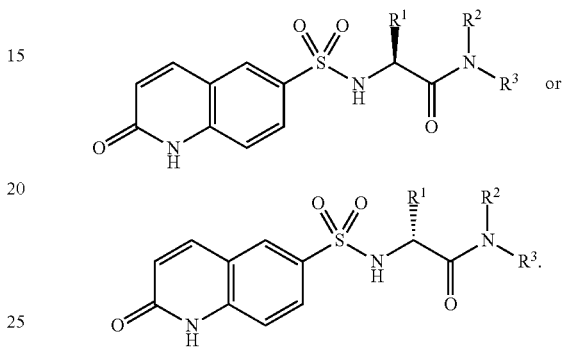

In certain embodiments, compounds of the invention are of the formula:

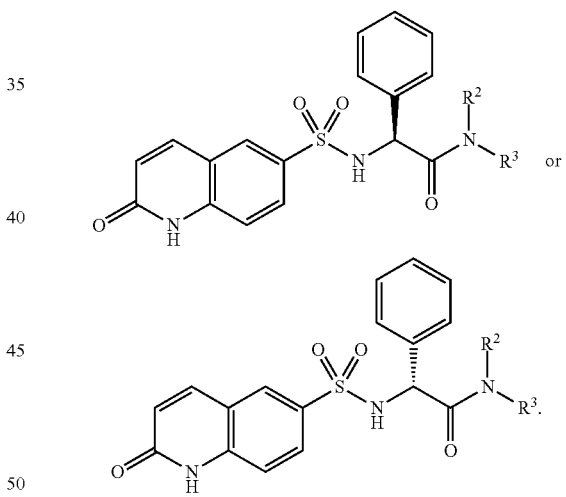

In certain embodiments, compounds of the invention are of the formula:

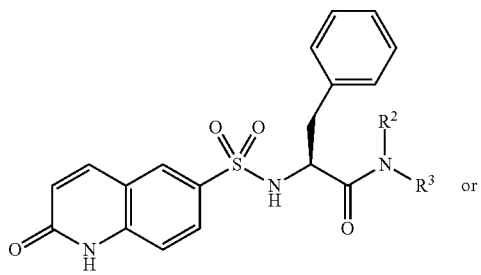

-continued

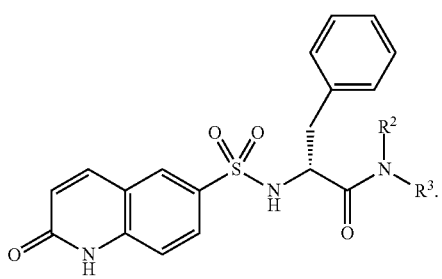

In certain embodiments, compounds of the invention are of the formula:

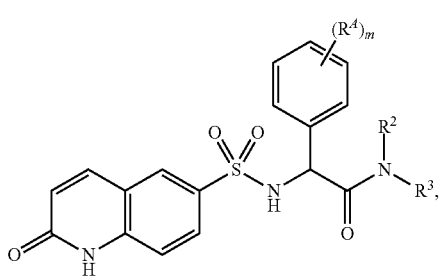

wherein $R^A$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR; —C(=O)R; —CO$_2$R; —C(=O)N(R)$_2$; —CN; —SCN; —SR; —SOR; —SO$_2$R; —NO$_2$; —N(R)$_2$; —NHC(O)R; or —C(R)$_3$; wherein each occurrence of R is independently hydrogen; halogen; a protecting group; aliphatic; heteroaliphatic; acyl; aryl moiety; heteroaryl; alkoxy; aryloxy; alkylthioxy; arylthioxy; amino; alkylamino; dialkylamino; heteroaryloxy; or heteroarylthioxy; and m is 0-5, inclusive.

In certain embodiments, compounds of the invention are of the formula:

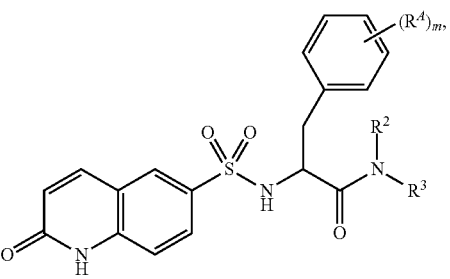

wherein $R^A$ and m are as defined above and described herein.

In certain embodiments, $R^A$ is hydrogen. In certain other embodiments, $R^A$ is halogen. In certain embodiments, $R^A$ is chloro. In certain embodiments, m is 1.

In certain embodiments, compounds of the invention are of the formula:

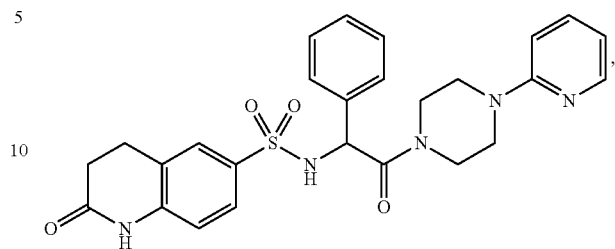

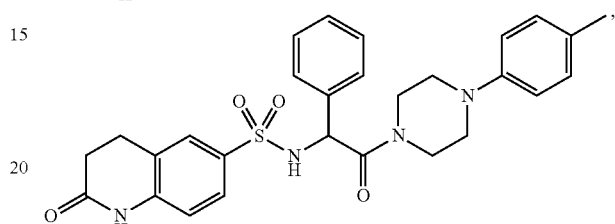

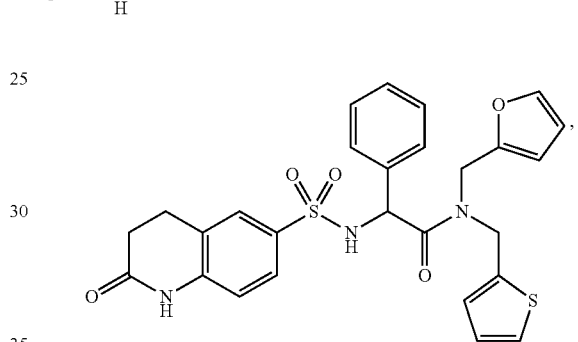

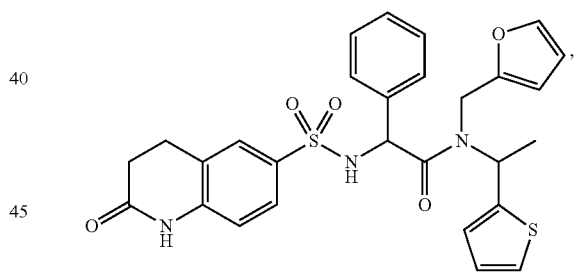

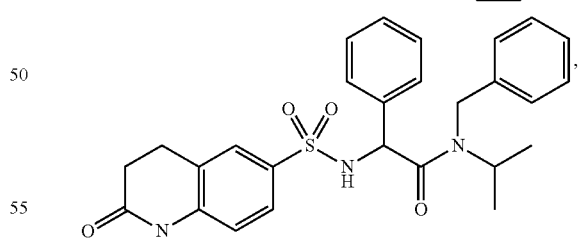

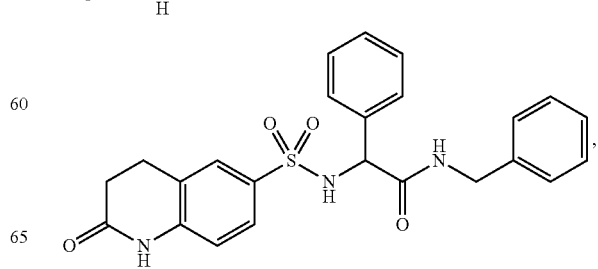

69
-continued
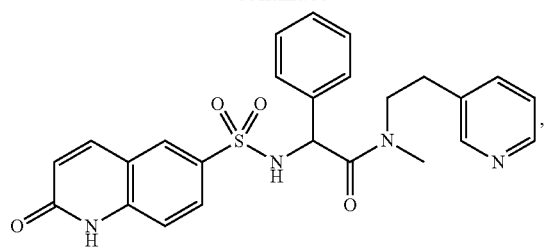
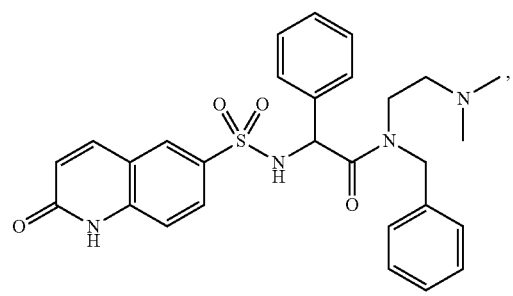
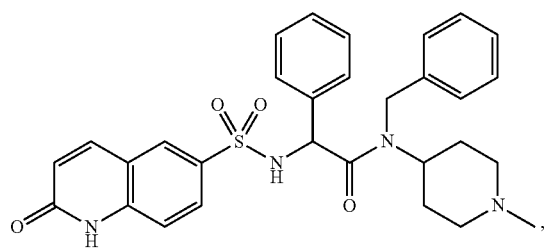
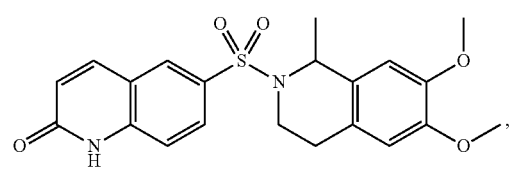
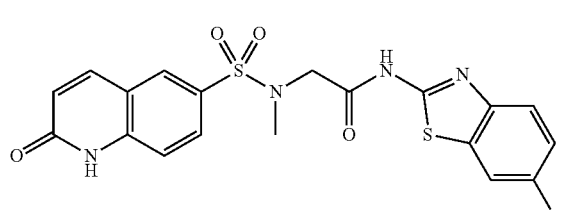
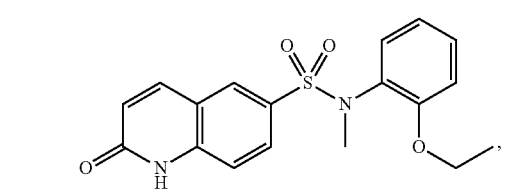
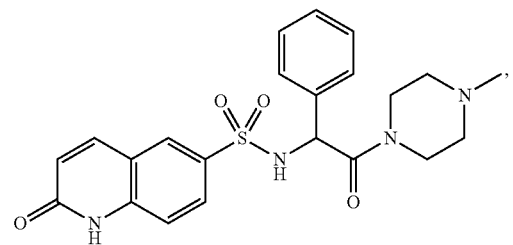
70
-continued
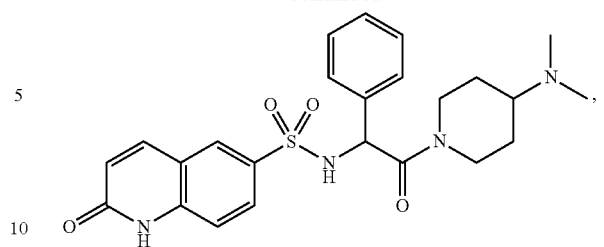
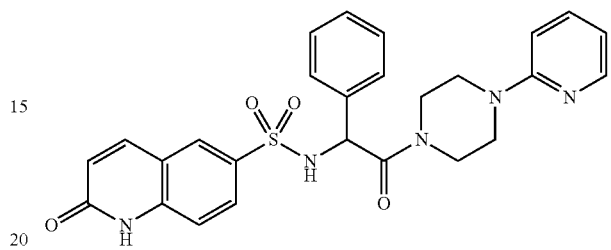
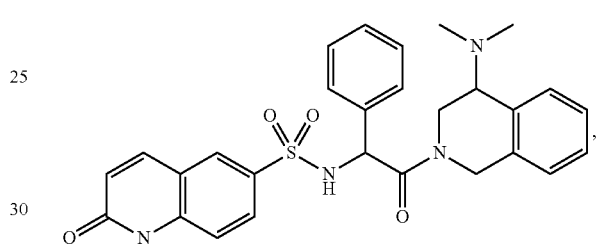
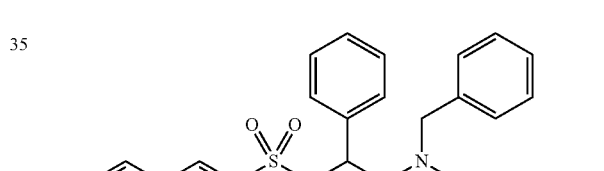
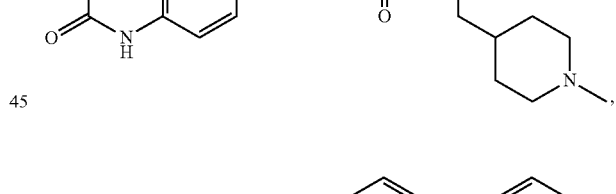
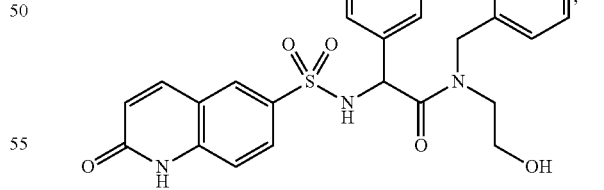
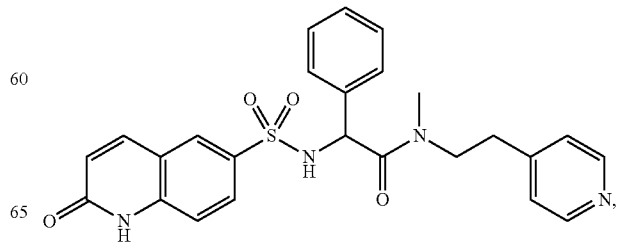

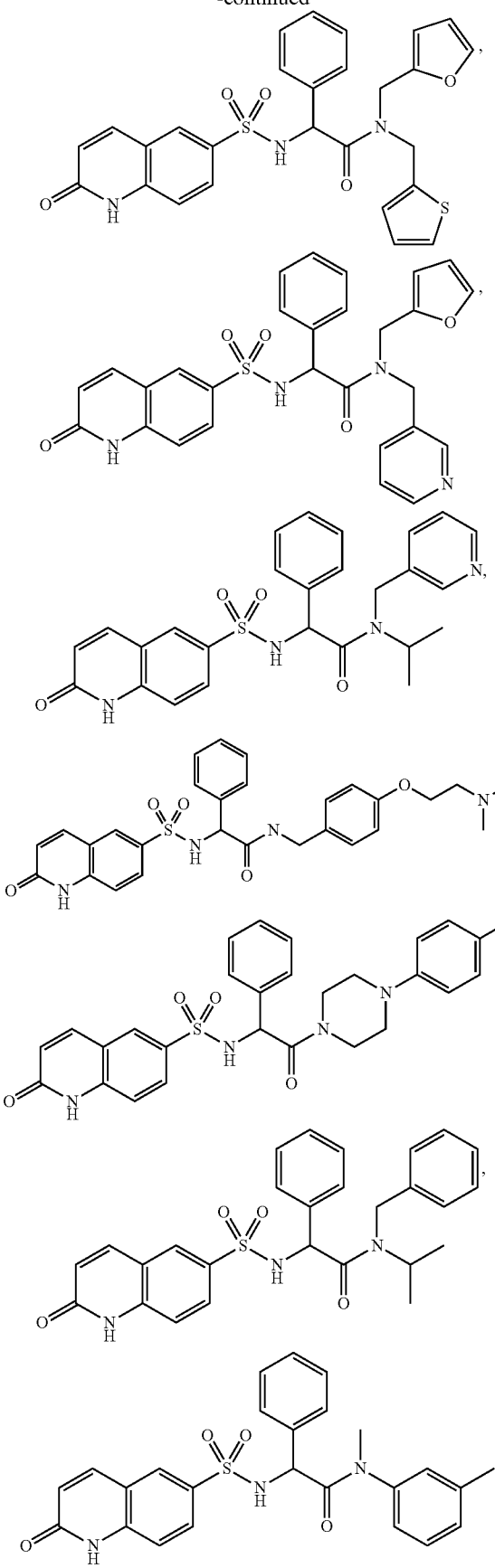
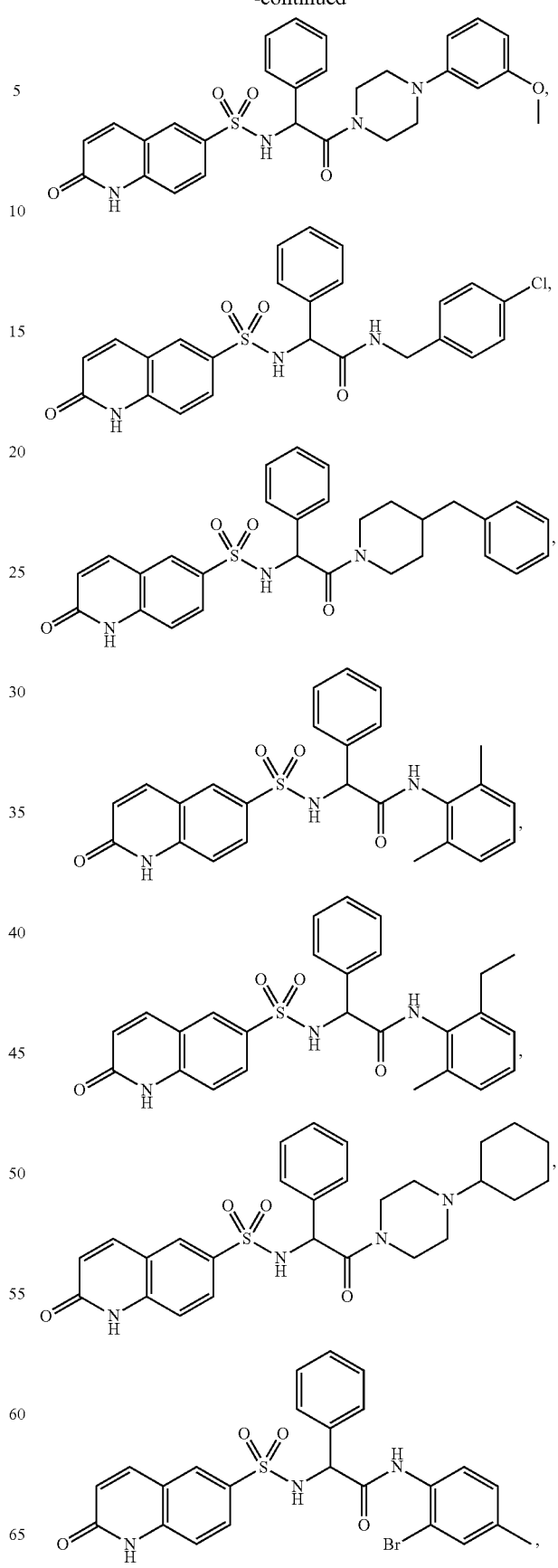

-continued

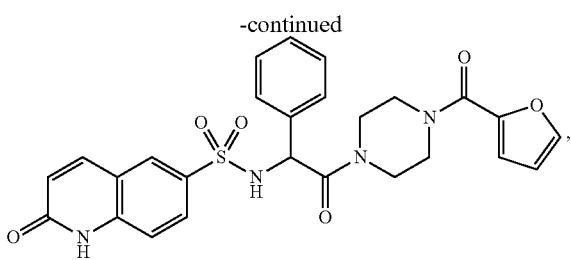,

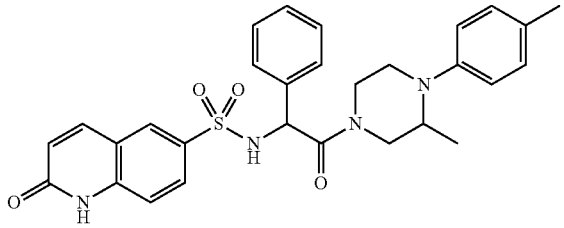,

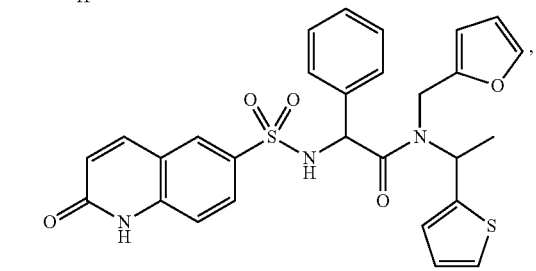,

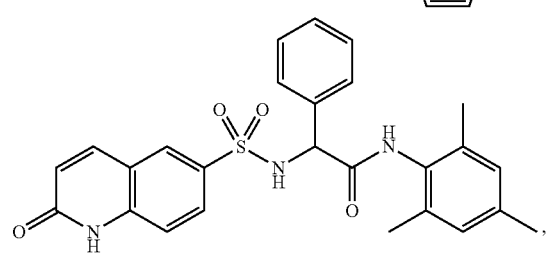,

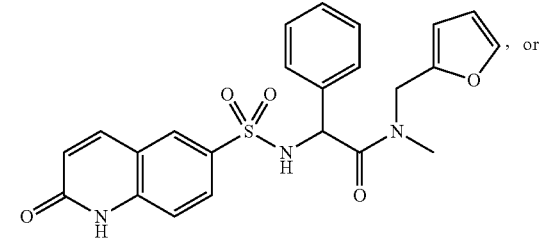, or

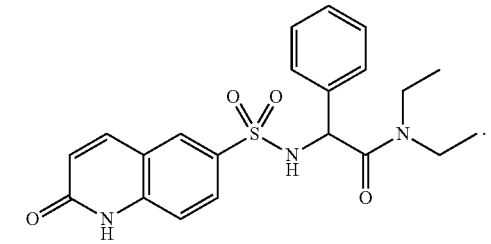.

Synthesis of OGT Inhibitors

In some embodiments, compounds of the invention may be synthesized according to Scheme 1. Quinolin-2(1H)-one may be chlorosulfonylated using methods known to those skilled in the art for chlorosulfonylation, such as neat chlorosulfonic acid with the addition of heat. The resulting chlorosulfonylquinolinone may be reacted with an amino acid, for example under aqueous basic conditions. A suitable aqueous base is, for example, aqueous sodium hydroxide. The amino acid may be a natural or unnatural amino acid. The resulting carboxylic acid may be further reacted with an amine under amide coupling conditions to furnish an amide. The amine may be a primary or secondary amine. Suitable coupling conditions are, for example, a coupling agent in the presence of base. A suitable coupling agent is, for example, HATU. A suitable base is, for example, Hunig's base.

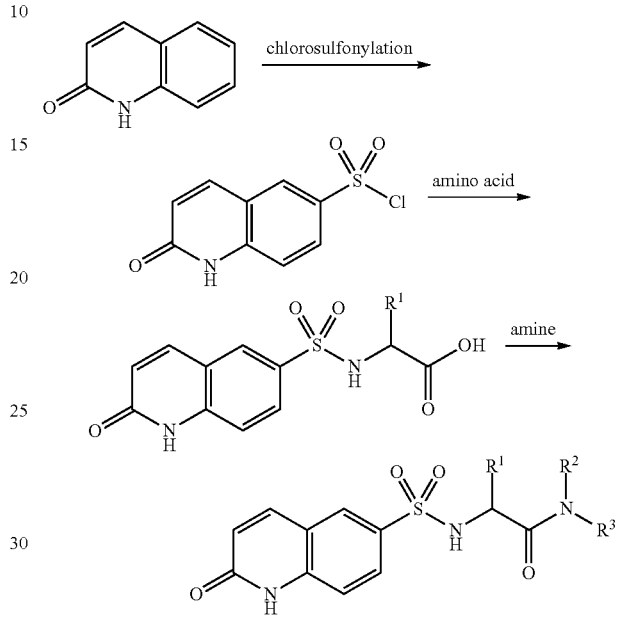

Uses of OGT Inhibitors and Pharmaceutical Compositions Thereof

The invention further provides methods of treating a disease using a compound of the invention. The inventive method involves the administration of a therapeutically effective amount of an inventive compound to a subject (including, but not limited to, a human or other animal) in need of it.

Compounds and compositions described herein are generally useful for the inhibition of the activity of O-GlcNAc transferase (OGT) or a mutant thereof. OGT has been implicated in diabetes and complications thereof, cancers, neurodegenerative diseases, autoimmune diseases, and inflammatory diseases (Golks, et al., *EMBO Reports* (2008) 9: 748-753; Liu, et al., *Proc. Natl. Acad. Sci. USA* (2004) 101: 10804-10809; Jones, *Circulation Research* (2005) 96: 925-926; Golks, et al., *EMBO J.* (2007) 26: 4369-4379; Ohn, et al., *Nature Cell Biol.* (2008) 10: 1224-1231), The compounds and pharmaceutical compositions of the invention may be used in treating or preventing any disease or condition including, but not limited to, diabetes and complications thereof, proliferative diseases (e.g., cancer, benign neoplasms, diabetic retinopathy), neurodegenerative diseases, autoimmune diseases (e.g., rheumatoid arthritis, lupus, multiple sclerosis) and inflammatory diseases and disorders. The inventive compounds and pharmaceutical compositions may be administered to animals, preferably mammals (e.g., domesticated animals, cats, dogs, mice, rats), and more preferably humans. Any method of administration may be used to deliver the inventive compound or pharmaceutical composition to the animal. In certain embodiments, the compound or pharmaceutical composition is administered orally. In other embodiments, the compound or pharmaceutical composition is administered parenterally.

In certain embodiments, the invention provides methods for treating or lessening the severity of diabetes and complications thereof including, but not limited to, diabetes mellitus Type 1, diabetes melittus Type 2, insulin resistance, vascular disease, skin ulcers, circulatory damage, cardiac dysfunction, diabetic nephropathy, diabetic retinopathy, microvascular disease, macrovascular disease, and diabetic neuropathy.

In some embodiments, the invention provides methods for treating tumorogenesis.

In certain embodiments, the inventive compounds are useful in treating a proliferative disease. In some embodiments, the invention provides methods for treating cancer. Examples of cancers treated with compounds according to the invention include, but are not limited to, tumors of the breast; biliary tract; bladder; bone; brain, including glioblastomas and medulloblastomas; central and peripheral nervous system; cervix; colon; connective tissue; endocrine glands (e.g., thyroid and adrenal cortex); esophagus; endometrium; germ cells; gastrointestinal tract; head and neck; kidney; liver; lung; larynx and hypopharynx; mesothelioma; muscle; ovary, including those arising from epithelial cells, stromal cells, germ cells and mesenchymal cells; pancreas; prostate; rectum; renal, including adenocarcinoma and Wilms tumor; small intestine; soft tissue; testis, including germinal tumors such as seminoma, non-seminoma (teratomas, choriocarcinomas), stromal tumors, and germ cell tumors; thyroid, including thyroid adenocarcinoma and medullar carcinoma; stomach; skin, including melanoma, Kaposi's sarcoma, basocellular cancer, and squamous cell cancer; ureter; vagina; and vulva; retinoblastoma; leukemia and lymphoma, namely non-Hodgkins disease, lymphocytic lymphomas, chronic and acute myeloid leukemia (CML/AML), acute lymphoblastic leukemia (ALL), chronic lymphocytic leukemia (CLL), Hodgkins disease, multiple myeloma, and T-cell lymphoma; myelodysplastic syndrome; plasma cell neoplasia; paraneoplastic syndromes; intraepithelial neoplasms including Bowen's disease and Paget's disease; neuroblastomas; oral cancer including squamous cell carcinoma; sarcomas including leiomyosarcoma, rhabdomyosarcoma, liposarcoma, fibrosarcoma, and osteosarcoma; cancers of unknown primary site; and AIDS-related malignancies. Other cancers will be known to one of ordinary skill in the art.

In certain embodiments, the invention provides methods for treating or lessening the severity of autoimmune diseases including, but not limited to, inflammatory bowel disease, arthritis, systemic lupus erythematosus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia.

In some embodiments, the invention provides a method for treating or lessening the severity of one or more diseases and conditions, wherein the disease or condition is selected from immune-related conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of an inflammatory disease including, but not limited to, asthma, appendicitis, Blau syndrome, blepharitis, bronchiolitis, bronchitis, bursitis, cervicitis, cholangitis, cholecystitis, chronic obstructive pulmonary disease (COPD), chronic recurrent multifocal osteomyelitis (CRMO), colitis, conjunctivitis, cryopyrin associated periodic syndrome (CAPS), cystitis, dacryoadenitis, dermatitis, dermatomyositis, dry eye syndrome, encephalitis, endocarditis, endometritis, enteritis, enterocolitis, epicondylitis, epididymitis, familial cold-induced autoinflammatory syndrome, familial Mediterranean fever (FMF), fasciitis, fibrositis, gastritis, gastroenteritis, hepatitis, hidradenitis suppurativa, laryngitis, mastitis, meningitis, mevalonate kinase deficiency (MKD), Muckle-Well syndrome, myelitis myocarditis, myositis, nephritis, oophoritis, orchitis, osteitis, inflammatory osteolysis, otitis, pancreatitis, parotitis, pericarditis, peritonitis, pharyngitis, pleuritis, phlebitis, pneumonitis, pneumonia, proctitis, prostatitis, pulmonary fibrosis, pyelonephritis, pyoderma gangrenosum and acne syndrome (PAPA), pyogenic sterile arthritis, rhinitis, salpingitis, sinusitis, stomatitis, synovitis, systemic juvenile rheumatoid arthritis, tendonitis, TNF receptor associated periodic syndrome (TRAPS), tonsillitis, undifferentiated spondyloarthropathy, undifferentiated arthropathy, uveitis, vaginitis, vasculitis, vulvitis, chronic inflammation resulting from chronic viral or bacteria infections, or psoriasis (e.g., plaque psoriasis, pustular psoriasis, erythrodermic psoriasis, guttate psoriasis or inverse psoriasis).

In certain embodiments, the present invention provides methods for treating or lessening the severity of arthropathies and osteopathological diseases including, but not limited to, rheumatoid arthritis, osteoarthrtis, gout, polyarthritis, and psoriatic arthritis.

In certain embodiments, the present invention provides methods for treating or lessening the severity of acute and chronic inflammatory diseases including, but not limited to, ulcerative colitis, inflammatory bowel disease, Crohn's disease, dry eye syndrome, allergic rhinitis, allergic dermatitis, cystic fibrosis, chronic obstructive bronchitis, and asthma.

In certain embodiments, the invention provides methods for treating or lessening the severity of hyperproliferative diseases including, but not limited to, psoriasis or smooth muscle cell proliferation including vascular proliferative disorders, atherosclerosis, and restenosis. In certain embodiments, the invention provides methods for treating or lessening the severity of endometriosis, uterine fibroids, endometrial hyperplasia, and benign prostate hyperplasia.

In certain embodiments, the invention provides methods for treating or lessening the severity of neurodegenerative disorders and/or tauopathies including, but not limited to, Alzheimer's disease, progressive supranuclear palsy, corticobasal degeneration, frontotemporal lobar degeneration, Pick's disease, Parkinson's disease, Lewy body disease, or amyotropic lateral sclerosis (ALS).

The invention further includes a method for the treatment of mammals, including humans, which are suffering from one of the above-mentioned conditions, illnesses, disorders, or diseases. The method comprises that a therapeutically effective amount of one or more of the compounds according to this invention or a composition thereof is administered to the subject in need of such treatment.

The invention further includes a method for inhibiting OGT in a cell or tissue using a compound of the invention.

The invention further relates to the use of the inventive compounds for the production of pharmaceutical compositions which are employed for the treatment and/or prophylaxis and/or amelioration of the diseases, disorders, illnesses, and/or conditions as mentioned herein.

The invention further relates to the use of the inventive compounds for the production of pharmaceutical compositions that inhibit OGT.

The invention further relates to the use of the inventive compounds for the production of pharmaceutical compositions which can be used for treating, preventing, or ameliorating diseases responsive to inhibiting OGT, such as diabetes and complications thereof, neurodegenerative diseases, cancers, autoimmune diseases, and inflammatory diseases, such as any of those diseases mentioned herein.

The exact amount required will vary from subject to subject, depending on the species, age, and general condition of the subject, the particular compound, its mode of administration, its mode of activity, and the like. The compounds of the invention are preferably formulated in dosage unit form for ease of administration and uniformity of dosage. It will be understood, however, that the total daily usage of the proteins and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific protein employed; the specific composition employed; the age, body weight, general health, sex, and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like. In certain embodiments, the compounds of the invention may be administered orally or parenterally at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such polyethoxylated castor oil, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as poly(lactide-co-glycolide). Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active protein may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions such as pectin-containing formulations can be used. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Additionally, the carrier for a topical formulation can be in the form of a hydroalcoholic system (e.g., liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

These and other aspects of the present invention will be further appreciated upon consideration of the following Examples, which are intended to illustrate certain particular embodiments of the invention but are not intended to limit its scope, as defined by the claims.

EXAMPLES

Example 1

General Procedure for Synthesizing Quinolinesulfonamides

Compounds of the invention are prepared according to the schemes, steps, and intermediates described below.

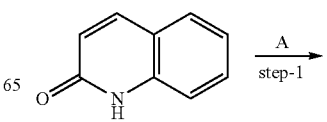

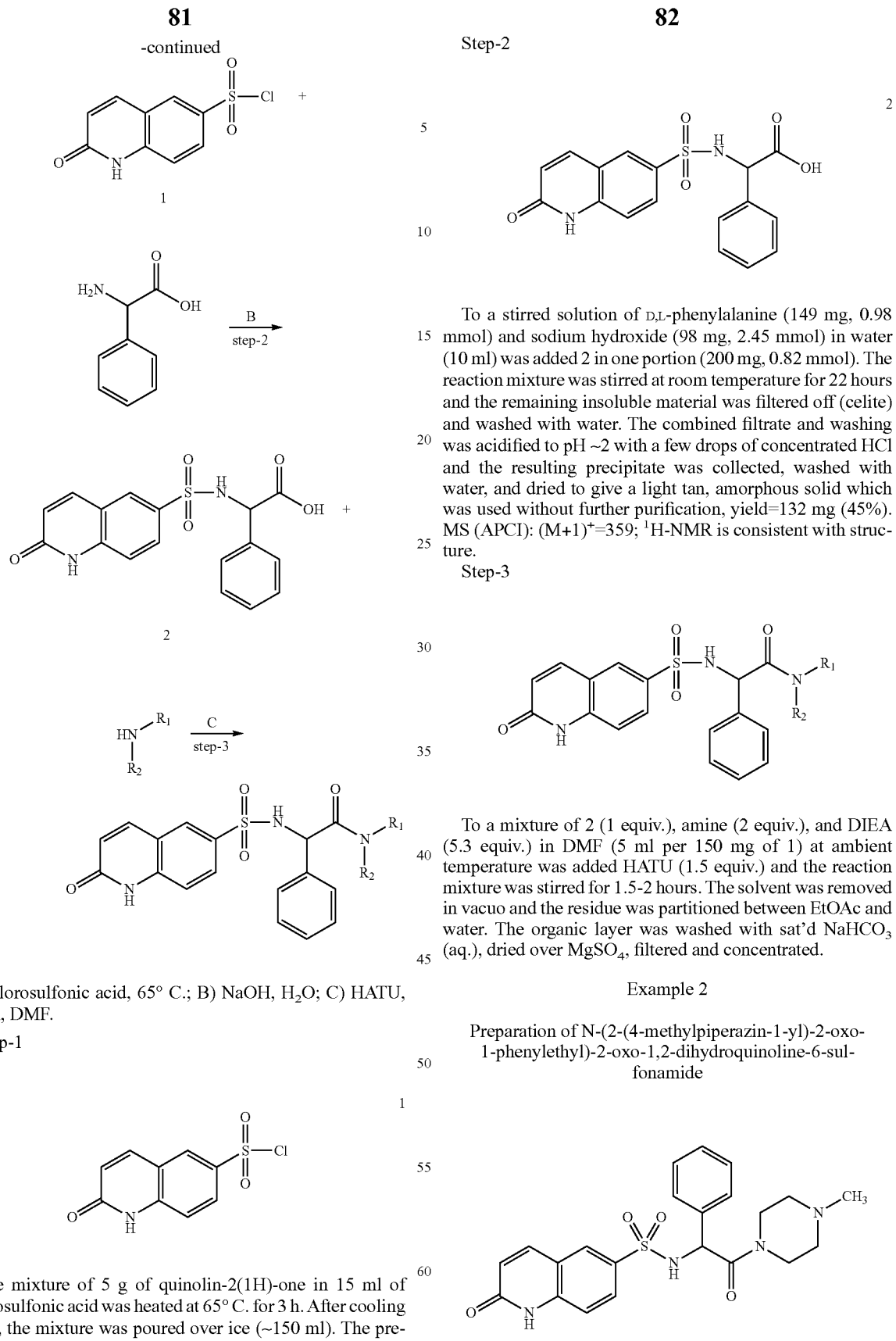

A) chlorosulfonic acid, 65° C.; B) NaOH, H₂O; C) HATU, DIEA, DMF.

Step-1

The mixture of 5 g of quinolin-2(1H)-one in 15 ml of chlorosulfonic acid was heated at 65° C. for 3 h. After cooling to RT, the mixture was poured over ice (~150 ml). The precipitate was filtered and the filter cake was washed with water. The product was dried under vacuum overnight to yield a light brown solid (5.1 g, 61%). MS and $^1$H-NMR are consistent with structure.

Step-2

To a stirred solution of D,L-phenylalanine (149 mg, 0.98 mmol) and sodium hydroxide (98 mg, 2.45 mmol) in water (10 ml) was added 2 in one portion (200 mg, 0.82 mmol). The reaction mixture was stirred at room temperature for 22 hours and the remaining insoluble material was filtered off (celite) and washed with water. The combined filtrate and washing was acidified to pH ~2 with a few drops of concentrated HCl and the resulting precipitate was collected, washed with water, and dried to give a light tan, amorphous solid which was used without further purification, yield=132 mg (45%). MS (APCI): (M+1)$^+$=359; $^1$H-NMR is consistent with structure.

Step-3

To a mixture of 2 (1 equiv.), amine (2 equiv.), and DIEA (5.3 equiv.) in DMF (5 ml per 150 mg of 1) at ambient temperature was added HATU (1.5 equiv.) and the reaction mixture was stirred for 1.5-2 hours. The solvent was removed in vacuo and the residue was partitioned between EtOAc and water. The organic layer was washed with sat'd NaHCO₃ (aq.), dried over MgSO₄, filtered and concentrated.

Example 2

Preparation of N-(2-(4-methylpiperazin-1-yl)-2-oxo-1-phenylethyl)-2-oxo-1,2-dihydroquinoline-6-sulfonamide The title compound was prepared according to the schemes, steps, and intermediates in Example 1, using 1-methylpiperazine as the amine. After removal of the reaction solvent, the crude product was washed with water and EtOAc (deviation from general workup) to give a gray, amorphous solid in 69% yield. MS (APCI): (M+1)$^+$=441; HPLC: 99% purity (C-18, RT=4.42 mins.); $^1$H-NMR is consistent with structure.

Example 3

Preparation of N-(furan-2-ylmethyl)-2-(2-oxo-1,2-dihydroquinoline-6-sulfonamido)-2-phenyl-N-(thiophen-2-ylmethyl)acetamide

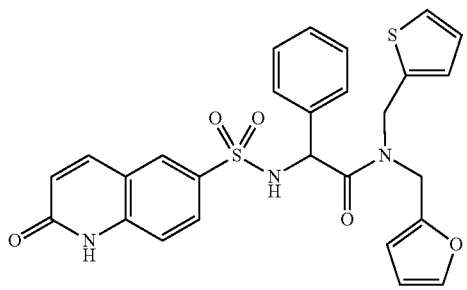 [SMILES: O=C(C(NS(=O)(=O)c1ccc2[nH]c(=O)ccc2c1)c1ccccc1)N(Cc1ccco1)Cc1cccs1]

The title compound was prepared according to the schemes, steps, and intermediates in Example 1, using furan-2-ylmethyl-thiophen-2-ylmethylamine as the amine. The product was purified by flash chromatography (silica gel 60, 230-400 mesh) using EtOAc as eluent. The purified product was isolated as an orange oil which solidified on standing. Trituration with cold EtOAc gave a light yellow solid in 13% yield. MS (APCI): (M+1)$^+$=534; HPLC: 97.4% purity (C-18, RT=5.00 mins.); $^1$H-NMR is consistent with structure.

Preparation of furan-2-ylmethyl-thiophen-2-ylmethylamine

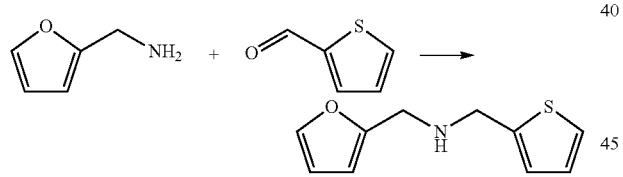

A mixture of furfurylamine (2.0 g, 0.0206 mol) and 2-thiophenecarboxaldehyde (2.31 g, 0.0206 mol) in dichloromethane (60 ml) was stirred at room temperature for 5 minutes before adding portionwise sodium triacetoxyborohydride (5.24 g, 0.0247 mol). After addition was complete (approx. 2 minutes), the reaction mixture was stirred at room temperature for 3 hours and washed with sat'd NaHCO$_3$ (aq.), dried (MgSO$_4$), filtered and concentrated. The product mixture was purified by flash chromatography (silica gel 60, 230-400 mesh, 4:1 hexanes:EtOAc to 1:1 hexanes:EtOAc) to obtain the amine as a light yellow oil, 1.65 g (41%). MS (APCI): (M+1)$^+$=194; $^1$H-NMR is consistent with structure.

Example 4

Screening of a Library of 1249 Quinolinesulfonamides for OGT Inhibition 384-well plates (Costar #3654) were filled using a liquid handling robot with 20 µL of a mixture of 50 nM of a fluorescein-linked UDP-GlcNAc analog (see Gross et al, 2003), 1-2 µM sOGT, and buffer (20 mM potassium phosphate, pH=7.4 with 500 µM tris(hydroxypropyl)phosphine). The 1249 compound library was serially diluted in DMSO from the 5 mg/ml plates fivefold 3 times, such that 4 different concentrations of compounds were prepared. Compound libraries of the 4 concentrations in duplicated were then transferred to the assay plates using a 100 nL pin array, resulting in a final compound concentration of 25 µg/mL or ~70 µM at the highest of the four concentrations, assuming an average compound MW of 350. Using a Perkin Elmer Envision® microplate reader, the sample was excited at 480 nm in the vertical plane, and simultaneous emission intensity (535 nm) of the vertical and horizontal polarization planes was measured. The polarization was calculated using the following equation: eq4: $mP=1000*(V-G*H)/(V+G*H)$ where: mP=millipolarization units, V=intensity of vertically polarized emission (RFU), H=intensity of horizontally polarized emission (RFU), and G=gain. Compounds were evaluated for their ability to affect the fluorescent polarization of the probe and rough $K_i$ values were determined based on the polarization results and the $K_d$ value of the probe.

TABLE 1

OGT Inhibition Data

| Compound | OGT Inhibition (µM) |
|---|---|
| | 7.4 |
| | 6.3 |
| | 6.6 |
| | 2 |

TABLE 1-continued
OGT Inhibition Data
| Compound | OGT Inhibition (μM) |
|---|---|
| 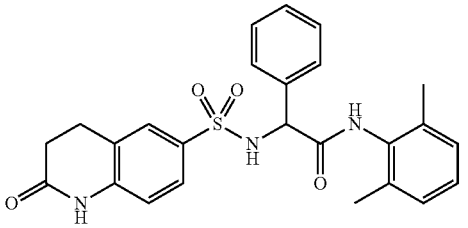 [SMILES: Cc1cccc(C)c1NC(=O)C(NS(=O)(=O)c1ccc2c(c1)CCC(=O)N2)c1ccccc1] | 37 |
| 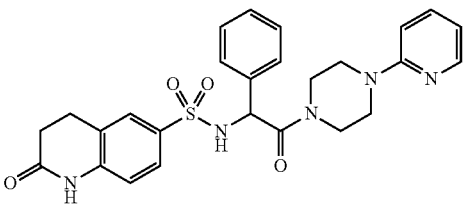 [SMILES: O=C1CCc2cc(S(=O)(=O)NC(C(=O)N3CCN(c4ccccn4)CC3)c3ccccc3)ccc2N1] | 4.2 |
| 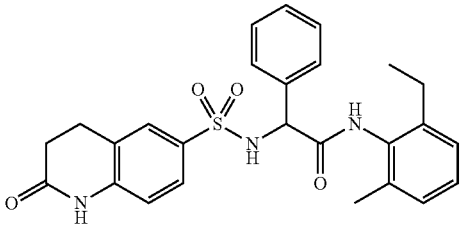 [SMILES: CCc1cccc(C)c1NC(=O)C(NS(=O)(=O)c1ccc2c(c1)CCC(=O)N2)c1ccccc1] | 97 |
| 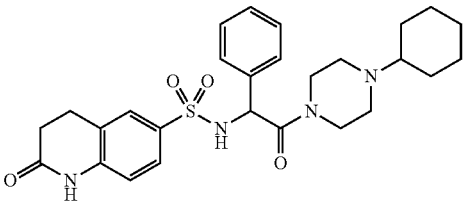 [SMILES: O=C1CCc2cc(S(=O)(=O)NC(C(=O)N3CCN(C4CCCCC4)CC3)c3ccccc3)ccc2N1] | 20 |
| 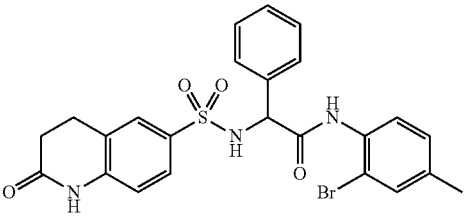 [SMILES: Cc1ccc(NC(=O)C(NS(=O)(=O)c2ccc3c(c2)CCC(=O)N3)c2ccccc2)c(Br)c1] | 52 |
| 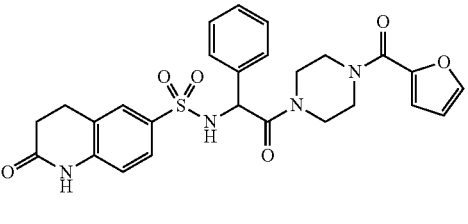 [SMILES: O=C1CCc2cc(S(=O)(=O)NC(C(=O)N3CCN(C(=O)c4ccco4)CC3)c3ccccc3)ccc2N1] | 11 |
TABLE 1-continued
OGT Inhibition Data
| Compound | OGT Inhibition (μM) |
|---|---|
| 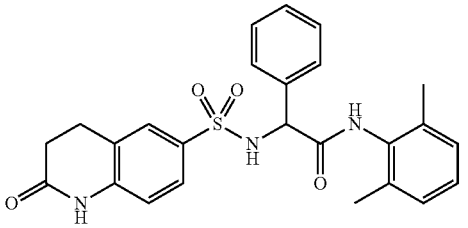 [SMILES: Cc1cccc(C)c1NC(=O)C(NS(=O)(=O)c1ccc2c(c1)CCC(=O)N2)c1ccccc1] | 3.2 |
| 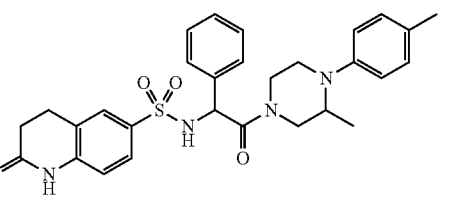 | 1.6 |
| 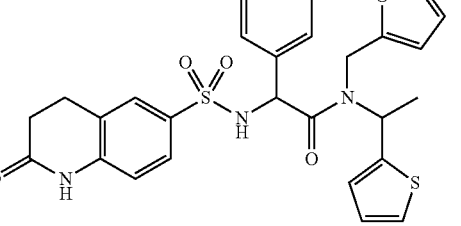 | 5.6 |
| 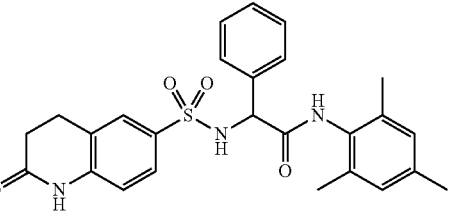 | 5.7 |
| 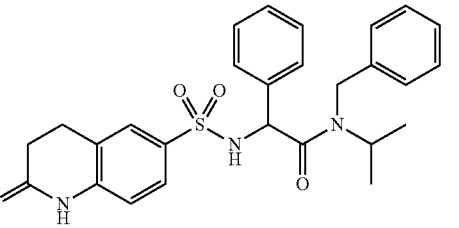 | 21 |
| 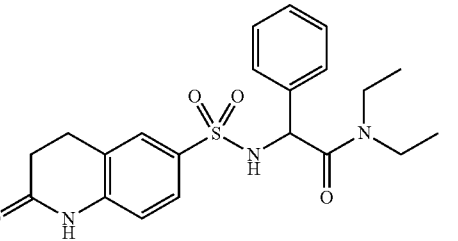 | 15 |

TABLE 1-continued

OGT Inhibition Data

| Compound | OGT Inhibition (μM) |
|---|---|
| (structure) | 13 |
| (structure) | 4.7 |
| (structure) | 50 |
| (structure) | 7.2 |
| (structure) | 4.1 |
| (structure) | 9 |
| (structure) | 60 |

TABLE 1-continued

OGT Inhibition Data

| Compound | OGT Inhibition (μM) |
|---|---|
| (structure) | 125 |
| (structure) | 50 |
| (structure) | 7 |
| (structure) | 4 |
| (structure) | 0.4 |

Example 5

Inhibition of OGT by Designed Quinolinesulfonamides

Hits were examined in a secondary assay involving the transfer of UDP-$^{14}$C-GlcNAc to a peptide derived from casein kinase II, which contains a known OGT glycosylation site, as described by Hart and co-workers (see manuscript, reference 4). Three lysines and a tyrosine were added to the N-terminus of this peptide substrate (KKKYPGGSTPVS-SANMM) to allow capture on phosphocellulose discs and UV detection, respectively. Compounds were twofold serially diluted in DMSO to a range of concentrations from 10 mM to 9.7 uM and then added 1:100 to a reaction mixture containing 500 μM peptide, 6.25 μM UDP-14C-GlcNAc, ~20-40 nM sOGT, and buffer (125 mM NaCl, 1 mM EDTA, 20 mM potassium phosphate, pH=7.4, and 500 μM tris(hydroxypropyl)phosphine). Reactions were spotted on Whatman P81 phosphocellulose discs, washed three times for five minutes in 1% phosphoric acid, and counted by liquid scintillation counting. IC50s curves were determined from the counts of the reactions and IC50s were determined.

N-(furan-2-ylmethyl)-2-(2-oxo-1,2-dihydroquinoline-6-sulfonamido)-2-phenyl-N-(thiophen-2-ylmethyl)acetamide (Example 3) inhibits OGT with an $IC_{50}$ of 390 nM.

Example 6

Glucosamine-Induced Cellular-Wide O-GlcNAcylation Changes in HEK Cells

The efficacy of the inhibitor in cell culture was evaluated by adding compound N08 to HEK293 cells. HEK293 cells were grown in 6 well plates using low glucose (5 mM) DMEM with 10% FBS as the media. When they were about 50-60% confluent a separate 6-well plate was prepared containing 2 ml of the media in each well, and added 0.5% DMSO to one well, 0.5% DMSO+4 mM glucosamine to another well in duplicate (as negative and positive controls for global GlcNAcylation changes) and to the rest N08 was added to a final concentration of 12.5 μM, in addition to glucosamine. After mixing the compounds the media was removed from the cultured cells and the inhibitor-media solutions was added to the cells. After cells were incubated with the inhibitors for 16 hours (overnight), the cells were rinsed with PBS, removed using cell scrapers, transferred to 1.5 ml microcentrifuge tubes, pelleted by centrifugation, and lysed by resuspending in 100 μl RIPA buffer with protease and phosphatase inhibitor cocktails (SIGMA). After incubating on ice the debris were pelleted down, and the supernatant was collected as whole cell lysate. Total protein concentration of each sample was determined by Bradford Assay in order to normalize levels of protein loaded onto a gel. Then 2×SDS-PAGE sample buffer was added to each sample, they were boiled for 10 minutes, and loaded onto a denaturing polyacrylamide gel (4-20% gradient), transferred to nitrocellulose membrane, blocked with 1% BSA for 1 hour, and probed with the monoclonal O-GlcNAc antibody, CTD110.6 (Covance), incubated at a 1:5000 dilution in 1% BSA overnight at 4° C., followed by addition of anti-mouse HRP secondary antibody. Pierce SuperSignal West Pico Chemiluminescent substrate was added to perform the western blot. FIG. 1 shows that N-(furan-2-ylmethyl)-2-(2-oxo-1,2-dihydroquinoline-6-sulfonamido)-2-phenyl-N-(thiophen-2-ylmethyl)acetamide (inhibitor N08) reduces glucosamine-induced cellular-wide O-GlcNAcylation changes to normal levels in HEK cells.

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A compound of formula (I):

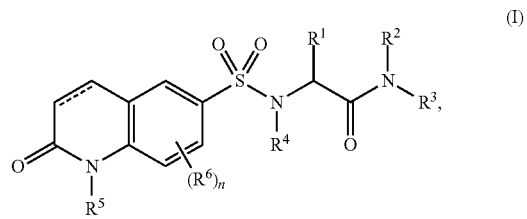

or a pharmaceutically acceptable salt thereof, wherein

---  denotes a single or double bond;

$R^1$ is cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; substituted or unsubstituted, branched or unbranched arylalkyl; or substituted or unsubstituted, branched or unbranched heteroarylalkyl;

$R^2$ and $R^3$ are independently cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; substituted or unsubstituted, branched or unbranched arylalkyl; substituted or unsubstituted, branched or unbranched heteroarylalkyl; —C(=O)$R^B$; —SO$R^B$; —SO$_2R^B$; or —C($R^B$)$_3$; wherein each occurrence of $R^B$ is independently hydrogen; halogen; a protecting group; aliphatic; heteroaliphatic; acyl; aryl; heteroaryl; hydroxyl; alkoxy; aryloxy; amino; alkylamino; dialkylamino; or heteroaryloxy; or $R^2$ and $R^3$ may optionally be taken together with the intervening nitrogen to form a saturated or unsaturated, substituted or unsubstituted heterocyclic moiety;

$R^4$ is hydrogen, $C_{1-6}$ aliphatic, or a protecting group;

$R^5$ is hydrogen, $C_{1-6}$ aliphatic, or a protecting group;

$R^6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R^F$; —C(=O)$R^F$; —CO$_2R^F$; —C(=O)N($R^F$)$_2$; —CN; —SCN; —S$R^F$; —SO$R^F$; —SO$_2R^F$; —NO$_2$; —N($R^F$)$_2$; —NHC(O)$R^F$; or —C($R^F$)$_3$; wherein each occurrence of $R^F$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy; and n is 0, 1, 2, or 3; wherein the compound of formula (I) is not one of the following:

91
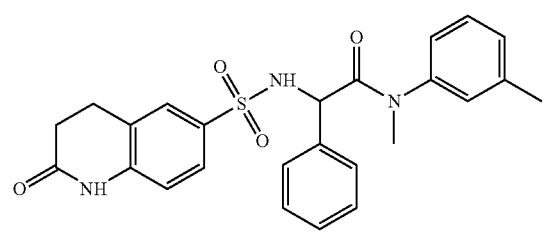
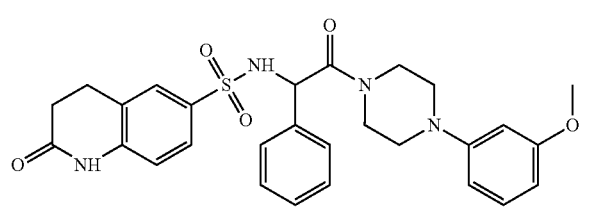
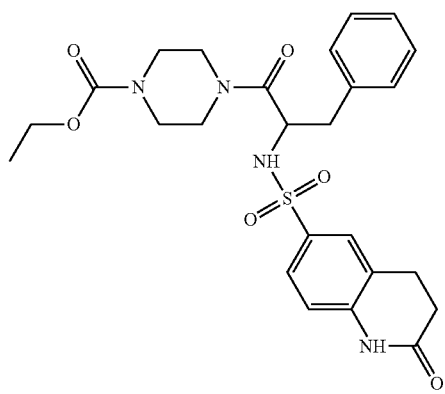
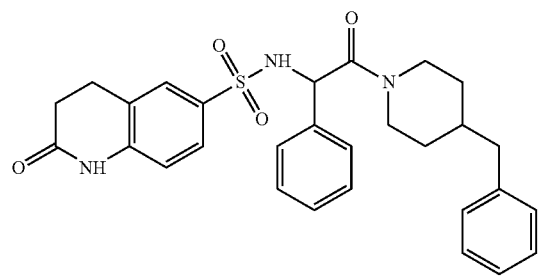
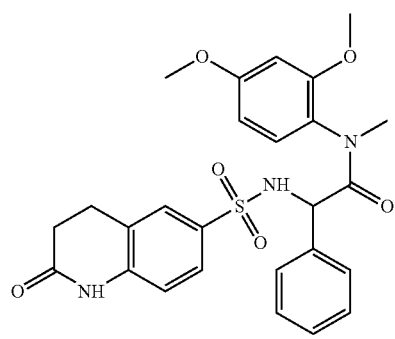
92
-continued
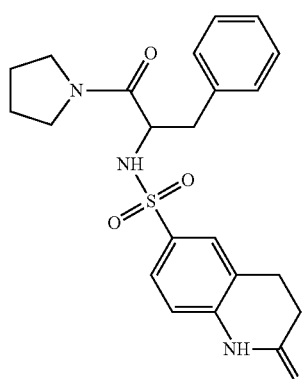
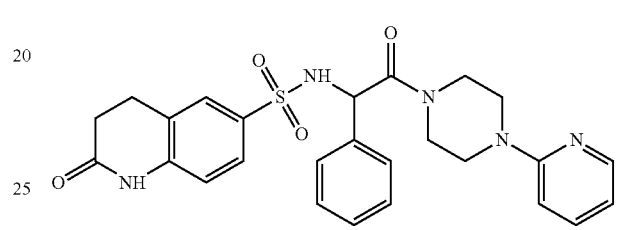
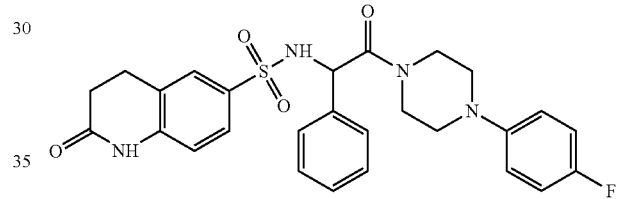
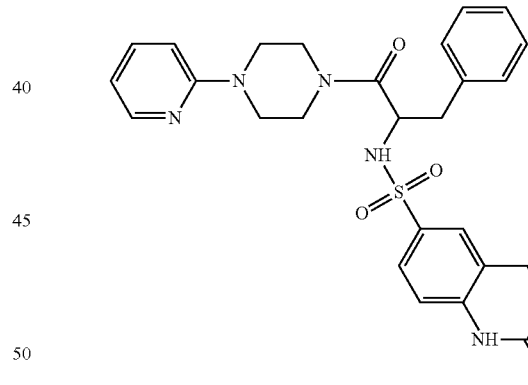
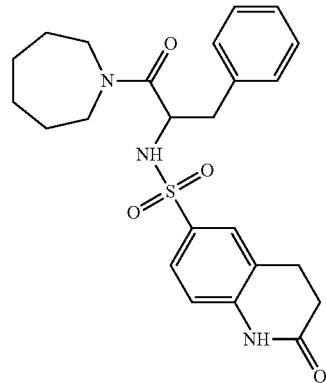

93
-continued
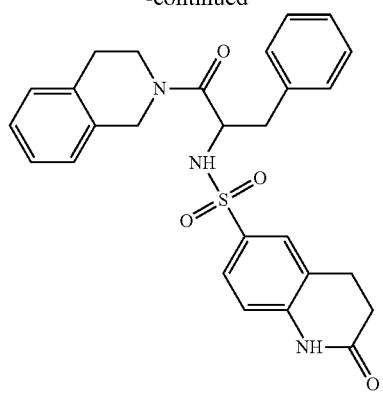
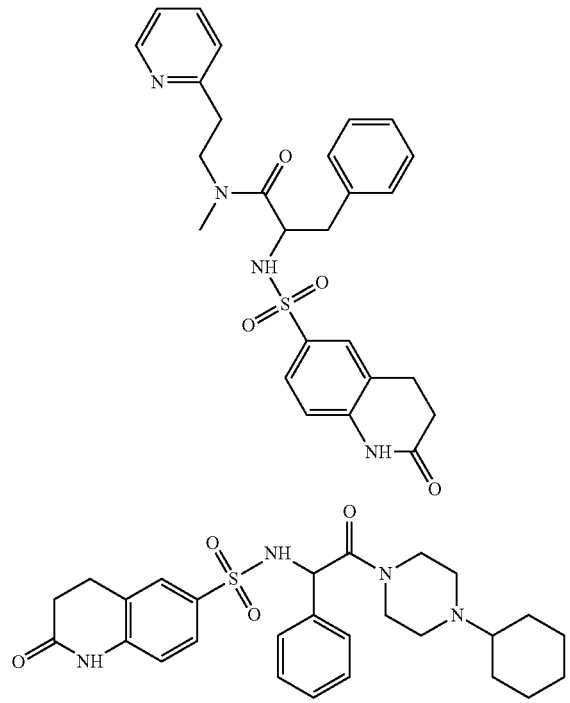
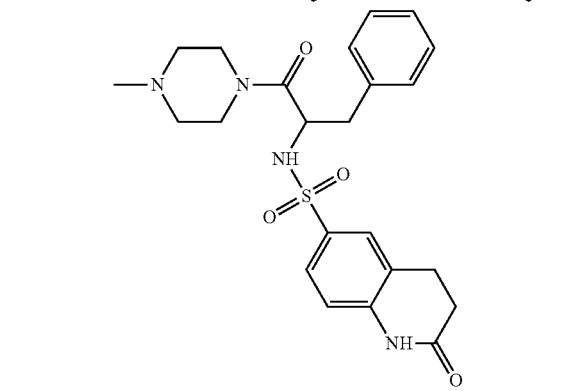
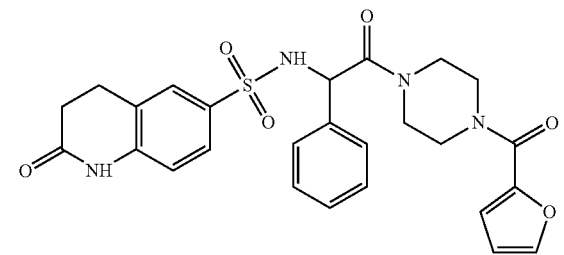
94
-continued
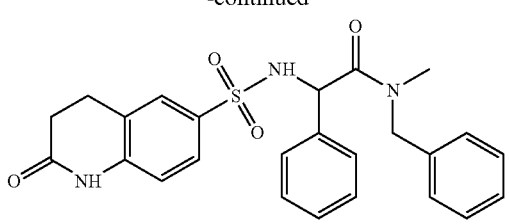
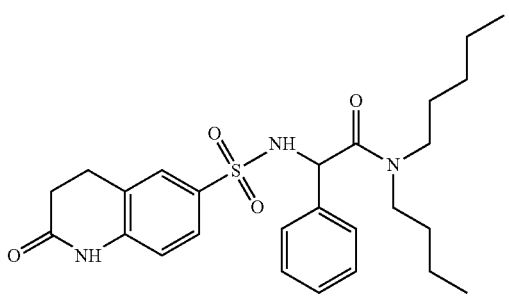
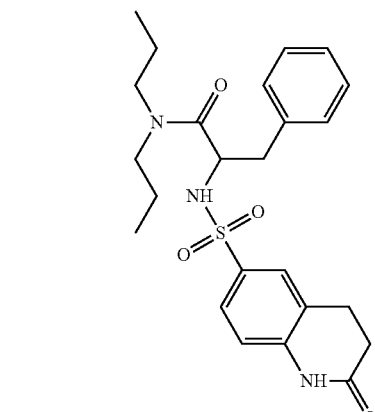
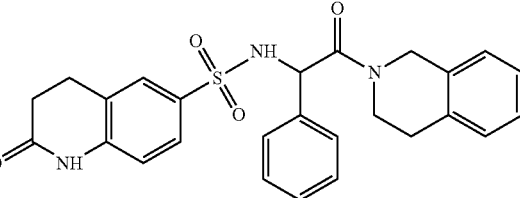
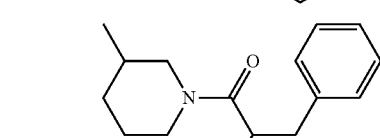
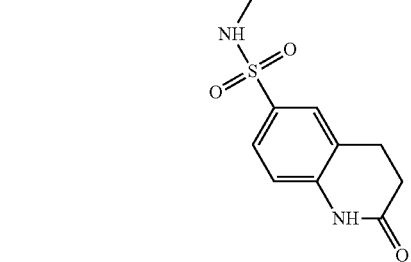

95
-continued
96
-continued
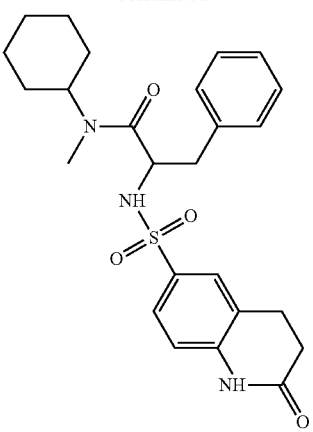
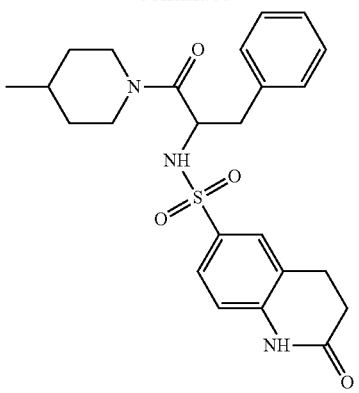
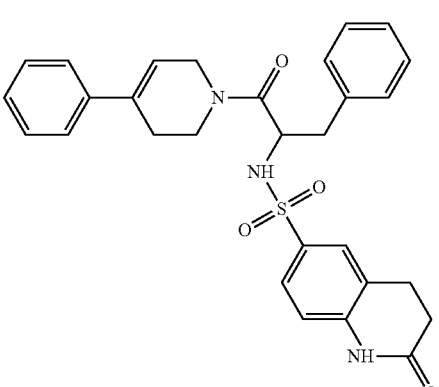
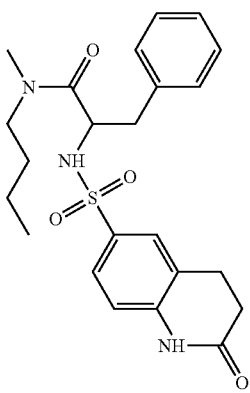
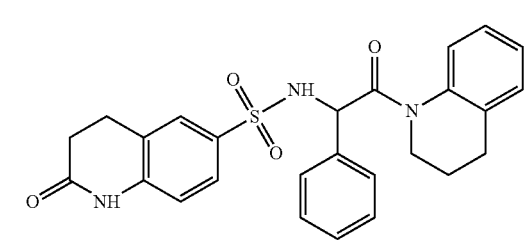
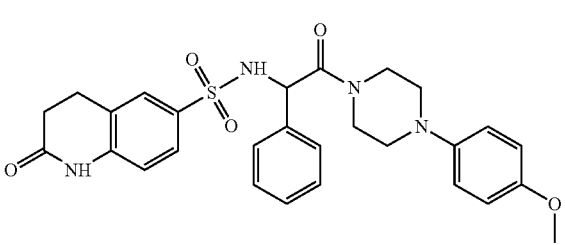

97
-continued
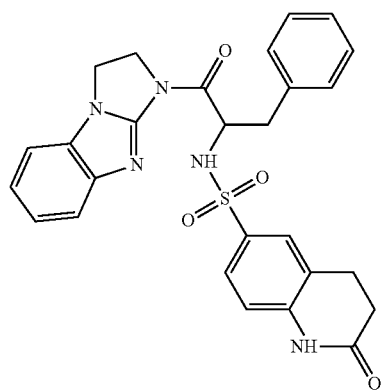
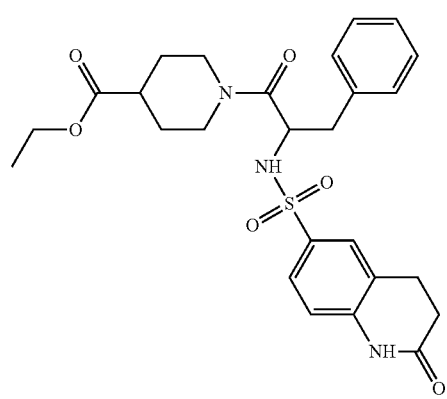
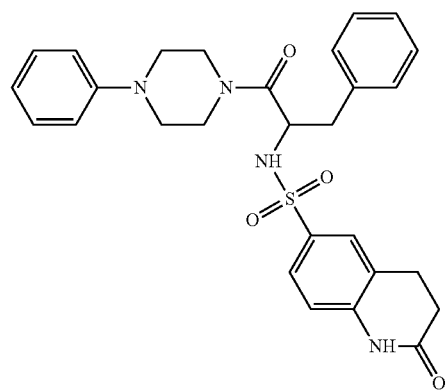
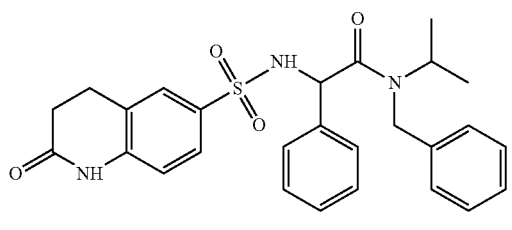
98
-continued
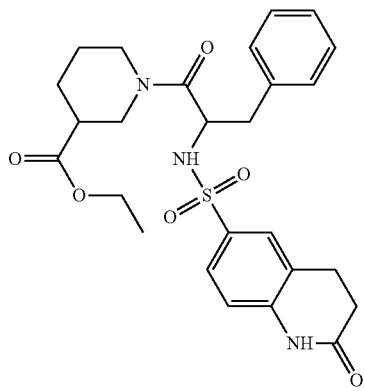
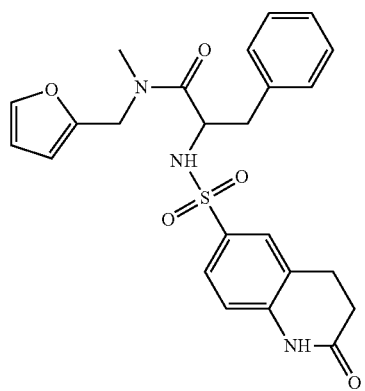
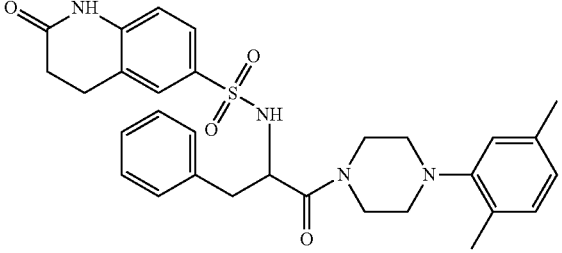
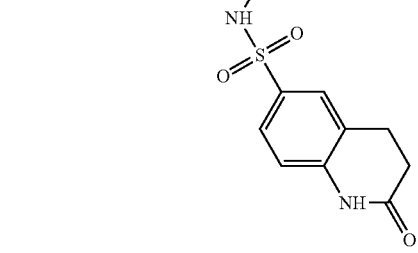

99
-continued
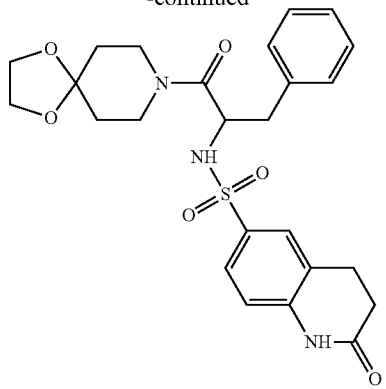
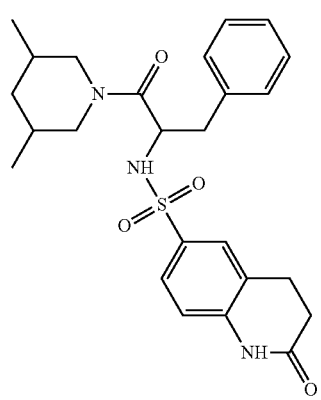
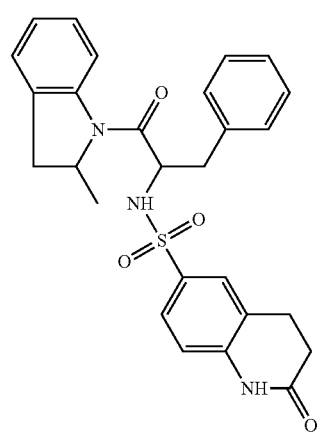
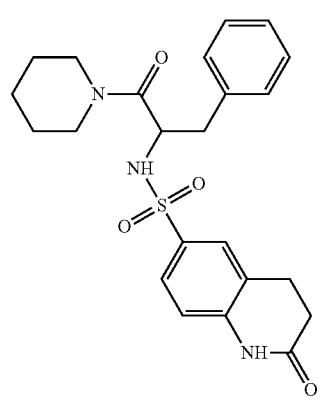
100
-continued
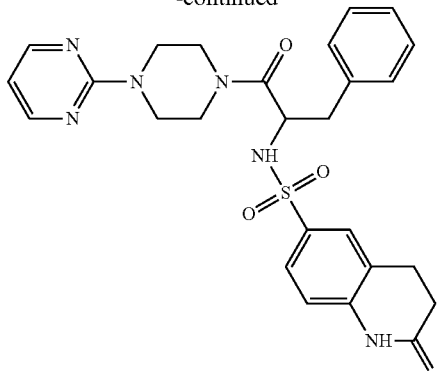
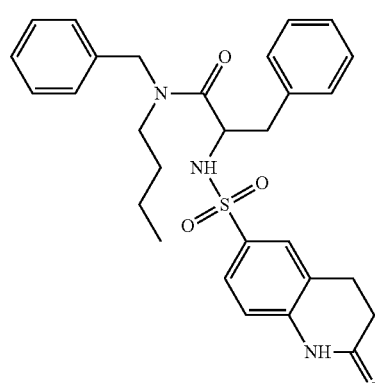
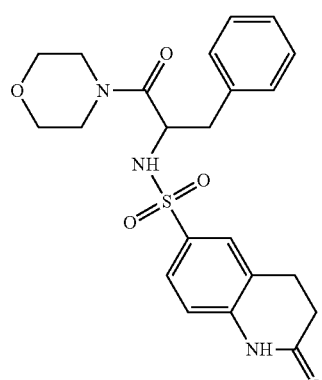
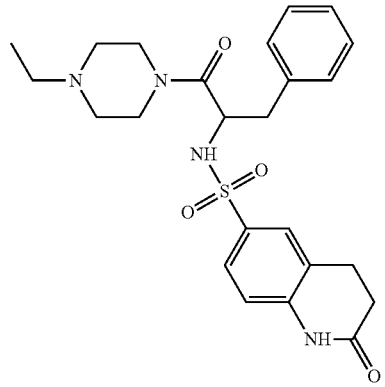

-continued
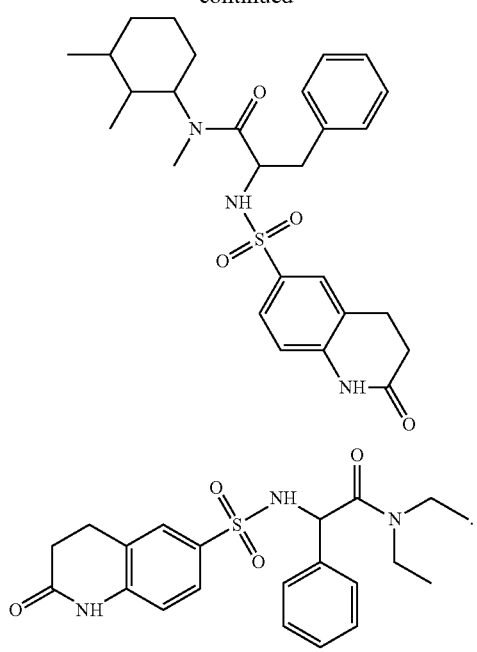
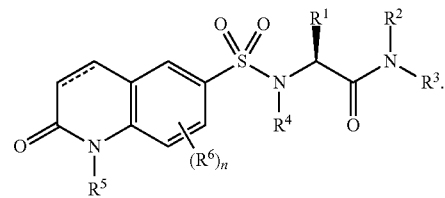
2. The compound of claim 1, wherein the compound has the stereochemistry of formula (Ia):
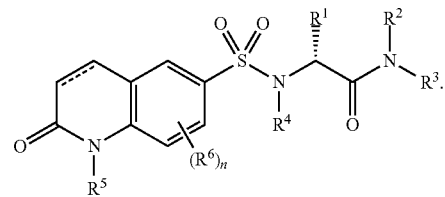
(Ia)
3. The compound of claim 1, wherein the compound has the stereochemistry of formula (Ib):
(Ib)
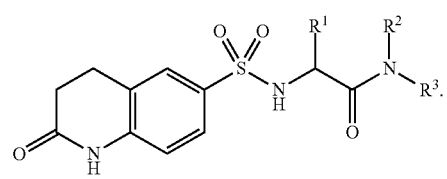
4. The compound of claim 1 of formula:
5. The compound of claim 1 of formula:
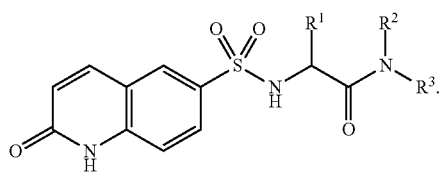
6. The compound of claim 1 of formula:
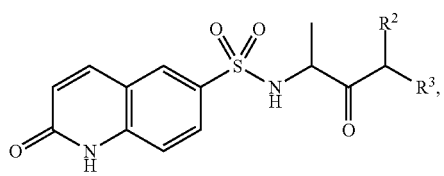
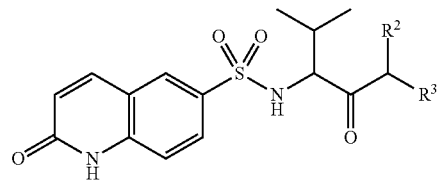
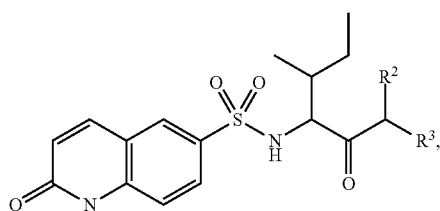
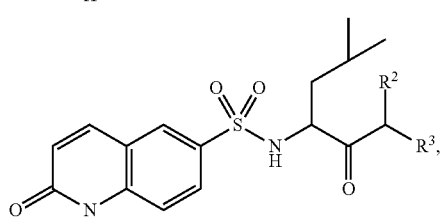
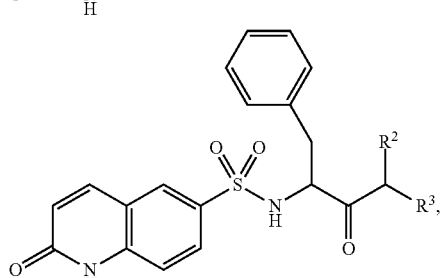
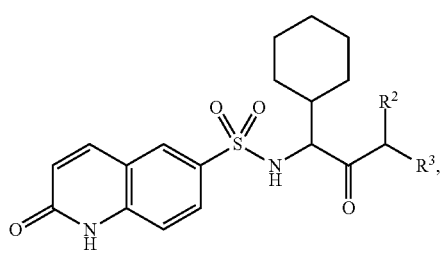

-continued

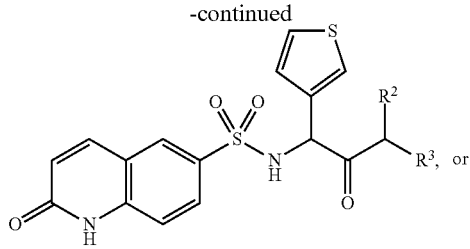

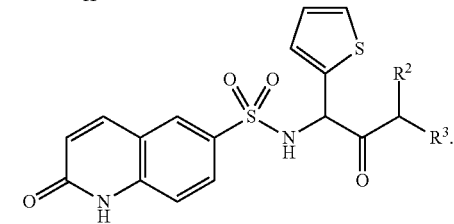

7. The compound of claim 1 of formula:

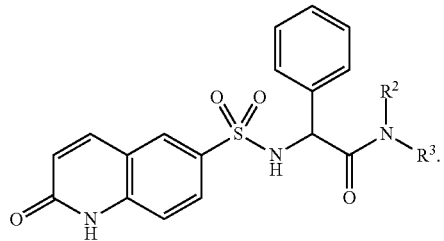

8. The compound of claim 1 of formula:

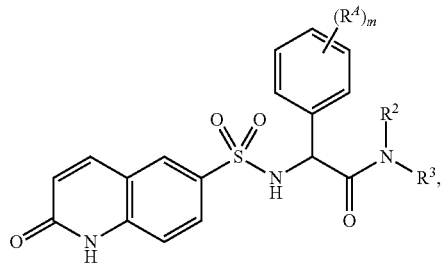

wherein
R$^A$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR; —C(=O)R; —CO$_2$R; —C(=O)N(R)$_2$; —CN; —SCN; —SR; —SOR; —SO$_2$R; —NO$_2$; —N(R)$_2$; —NHC(O)R; or —C(R)$_3$; wherein each occurrence of R is independently hydrogen; halogen; a protecting group; aliphatic; heteroaliphatic; acyl; aryl moiety; heteroaryl; alkoxy; aryloxy; alkylthioxy; arylthioxy; amino; alkylamino; dialkylamino; heteroaryloxy; or heteroarylthioxy; and
m is 0-5, inclusive.

9. The compound of claim 1, wherein R$^2$ and R$^3$ are taken together to form a heterocyclic ring.

10. The compound of claim 1, wherein each of R$^2$ and R$^3$ is C$_{1-6}$ alkyl, C$_{1-6}$ heteroalkyl, aryl, heteroaryl, arylalkyl, or heteroarylalkyl.

11. The compound of claim 1, wherein one of R$^2$ and R$^3$ is C$_{1-6}$ alkyl, C$_{1-6}$ heteroalkyl, aryl, heteroaryl, arylalkyl, or heteroarylalkyl.

12. A compound having the formula:

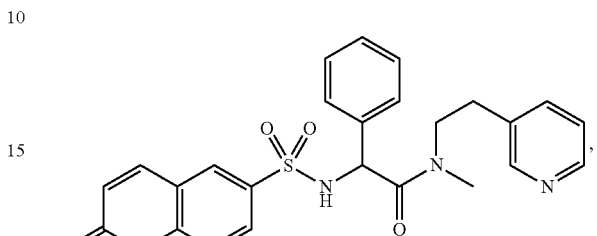

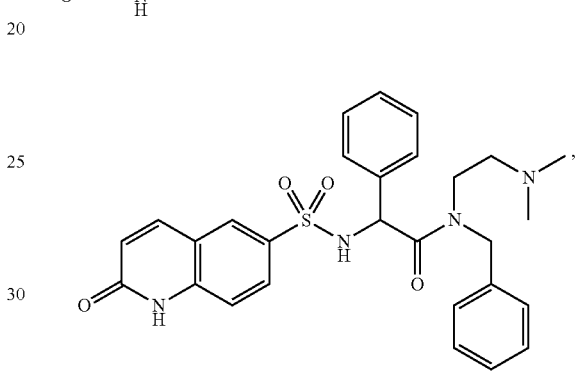

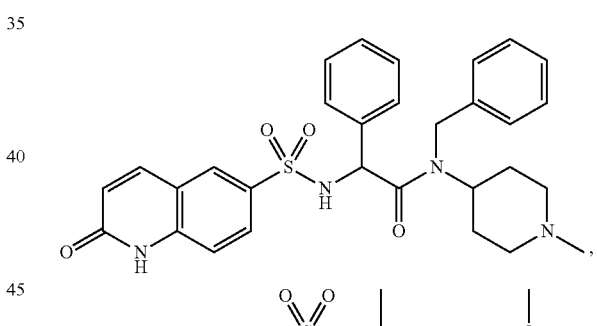

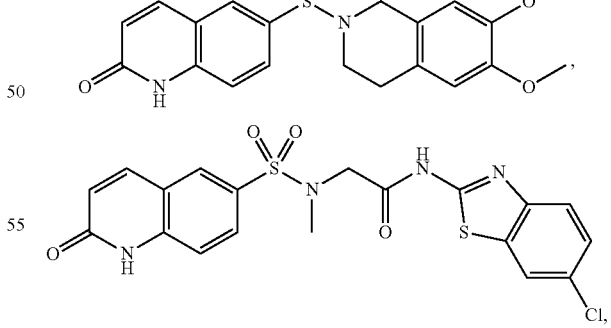

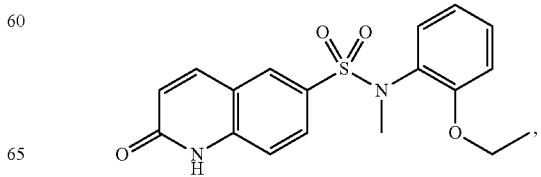

105
-continued
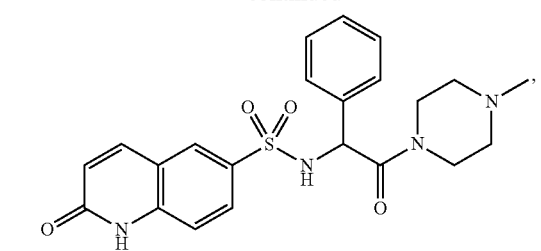
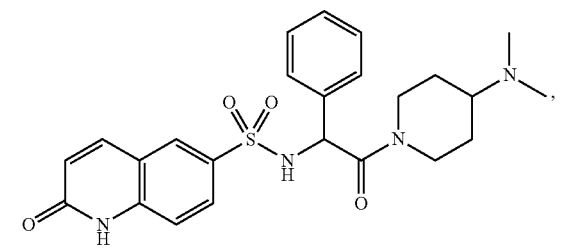
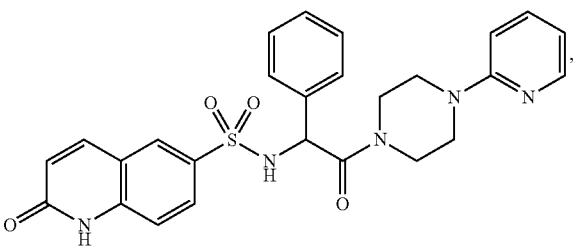
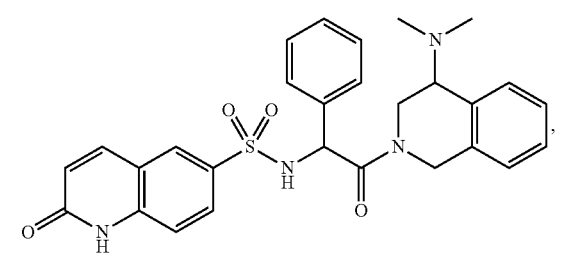
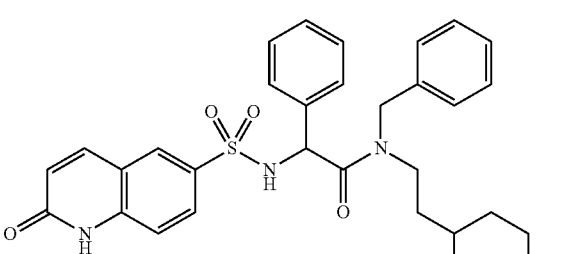
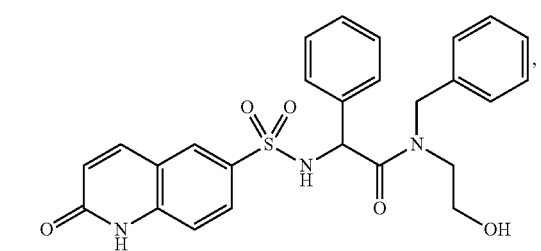
106
-continued
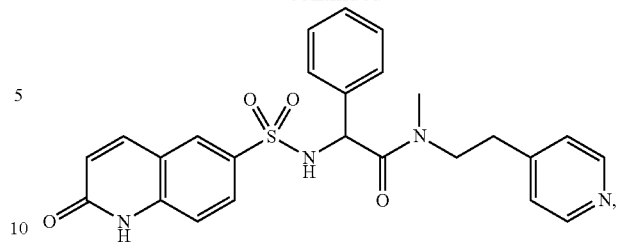
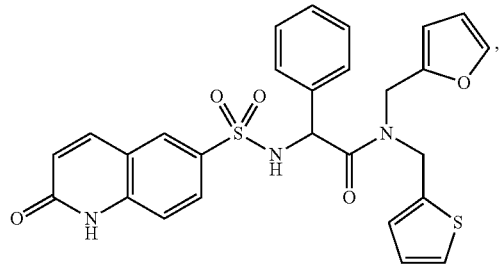
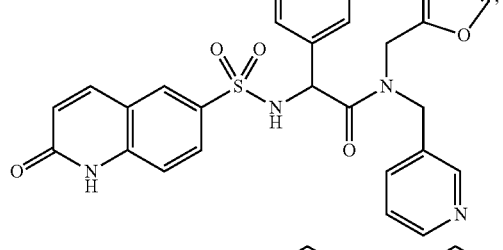
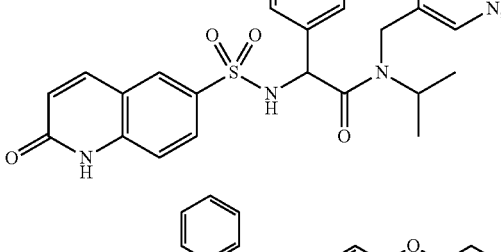
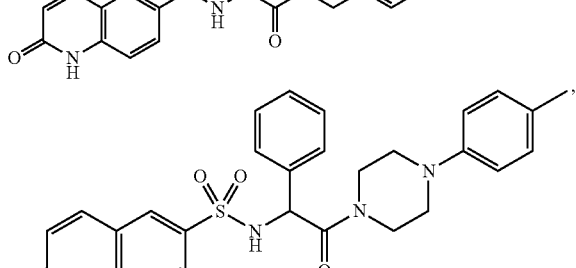
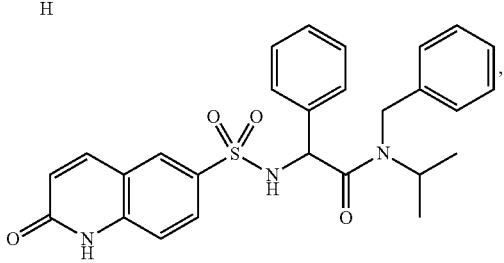

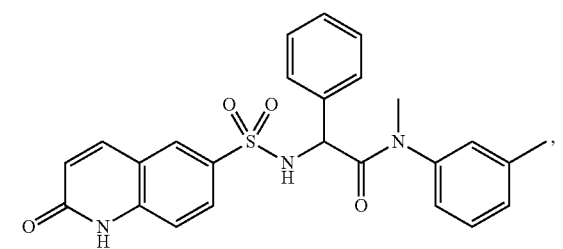
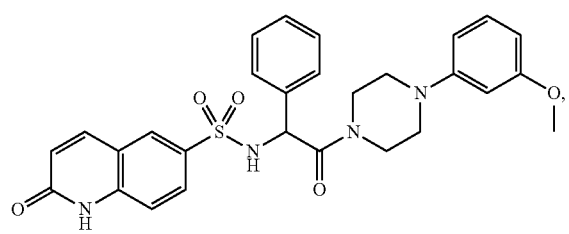
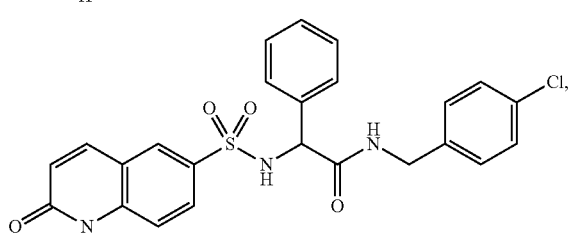
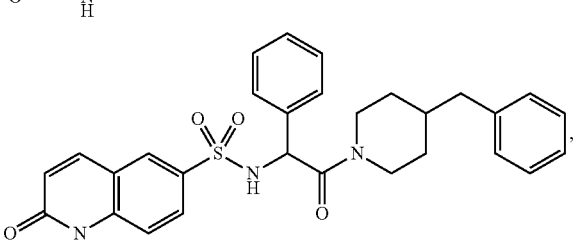
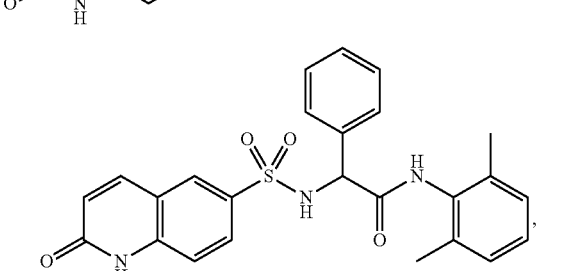
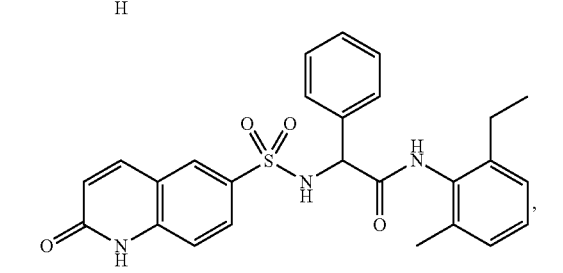
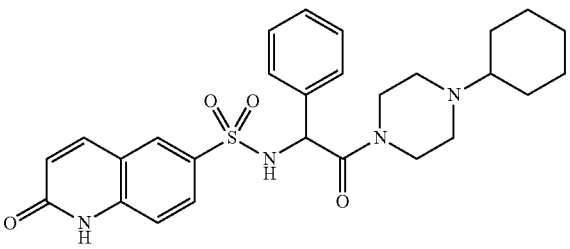
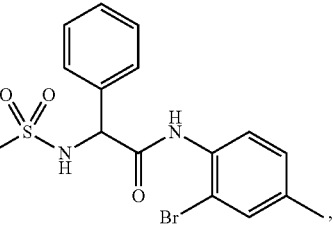
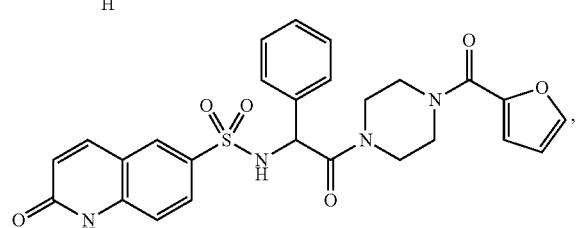
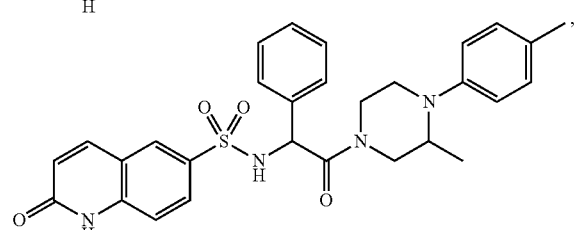
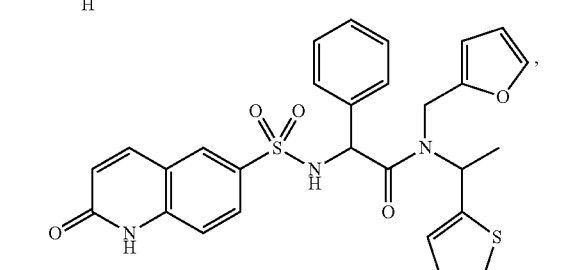
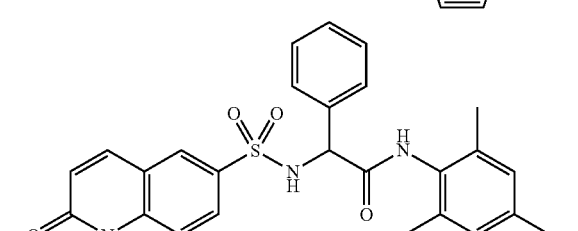
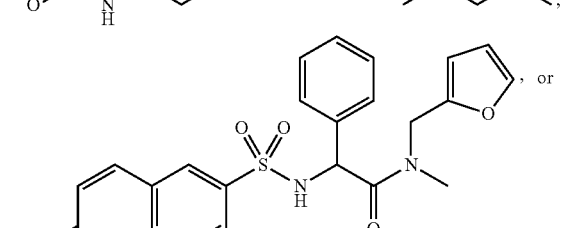
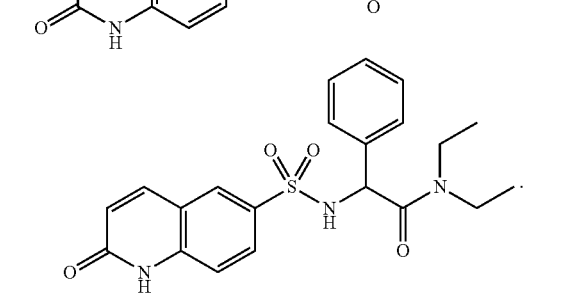

13. A pharmaceutical composition comprising a therapeutically effective amount of a compound of claim 1; and a pharmaceutically acceptable excipient.

14. A method for treating an OGT-associated disease or condition in a subject comprising administering to a subject in need of such treatment a therapeutically effective amount of a compound of claim 1.

15. The method of claim 14, wherein the subject is human.

16. The method of claim 14, wherein the OGT-associated disease or condition is cancer, diabetes mellitus type I, diabetes mellitus type II, insulin resistance, a complication of diabetes, or inflammatory disease.

17. The compound of claim 1, wherein ═══ is a single bond and $R^1$ is not phenyl or benzyl.

18. The compound of claim 1, wherein ═══ is a double bond.

19. The compound of claim 1 of formula:

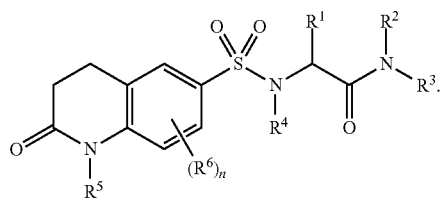

20. The compound of claim 1 of formula:

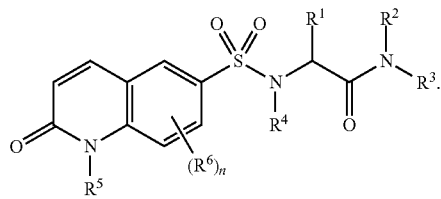

21. The compound of claim 20 of formula:

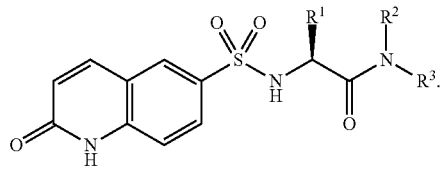

22. The compound of claim 20 of formula:

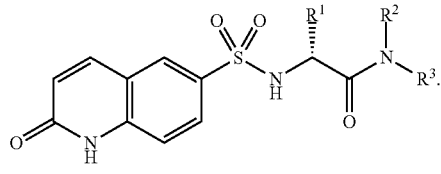

23. The compound of claim 7, wherein the compound has the stereochemistry of formula:

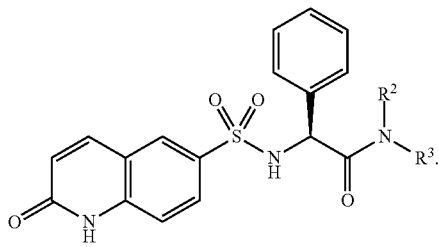

24. The compound of claim 7, wherein the compound has the stereochemistry of formula:

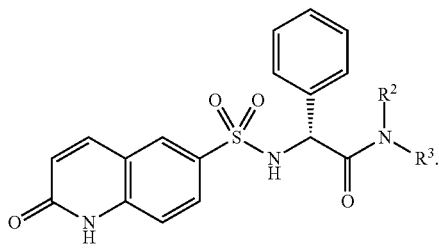

25. The compound of claim 8, wherein the compound has the stereochemistry of formula:

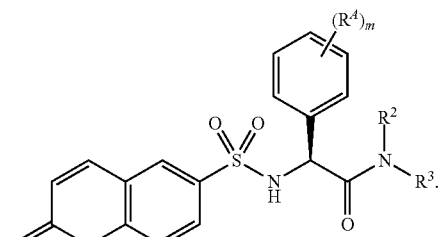

26. The compound of claim 8, wherein the compound has the stereochemistry of formula:

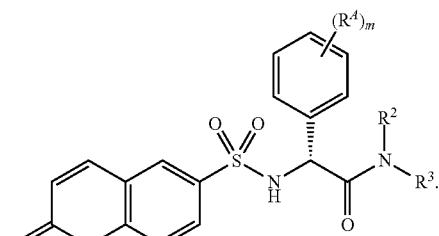

27. The compound of claim 8, wherein $R^A$ is halogen and m is 1.

28. The compound of claim 8, wherein $R^A$ is chloro or fluoro.

29. The compound of claim 9, wherein $R^2$ and $R^3$ are taken together to form a 6-membered heterocyclic ring.

30. The compound of claim 9, wherein $R^2$ and $R^3$ are taken together to form an optionally substituted pyrrolidine, piperidine, or homopiperidine ring.

31. The compound of claim 9, wherein $R^2$ and $R^3$ are taken together to form an optionally substituted piperazine ring.

32. The compound of claim 31, wherein the piperazine ring is substituted with an optionally substituted aryl or heteroaryl moiety.

33. The compound of claim 1, wherein at least one of $R^2$ and $R^3$ is aryl, arylalkyl, heteroaryl, or heteroarylalkyl.

34. The compound of claim 33, wherein each of $R^2$ and $R^3$ is arylalkyl or heteroarylalkyl.

35. The compound of claim 33, wherein each of $R^2$ and $R^3$ is heteroarylalkyl.

36. A pharmaceutical composition comprising a therapeutically effective amount of a compound of claim 12; and a pharmaceutically acceptable excipient.

37. The pharmaceutical composition of claim 13, administered in an amount sufficient to deliver about 0.001 mg/kg to about 100 mg/kg of subject body weight per day.

* * * * *